(12) United States Patent
Schmidt et al.

(10) Patent No.: US 8,877,903 B2
(45) Date of Patent: Nov. 4, 2014

(54) SEPARATION OF INSOLUBLE TARGET PROTEINS

(75) Inventors: Martin Schmidt, Fredersdorf (DE);
Axel Lelmer, Frankfurt am Main (DE);
Lin Römer, Ottobrunn (DE)

(73) Assignee: Amsilk GmbH, Planegg (DE)

( * ) Notice: Subject to any disclaimer, the term of this patent is extended or adjusted under 35 U.S.C. 154(b) by 0 days.

(21) Appl. No.: 13/638,494

(22) PCT Filed: Mar. 30, 2011

(86) PCT No.: PCT/EP2011/001605
§ 371 (c)(1),
(2), (4) Date: Jan. 9, 2013

(87) PCT Pub. No.: WO2011/120690
PCT Pub. Date: Oct. 6, 2011

(65) Prior Publication Data
US 2013/0338346 A1    Dec. 19, 2013

Related U.S. Application Data

(60) Provisional application No. 61/319,542, filed on Mar. 31, 2010.

(51) Int. Cl.
*C07K 1/14*    (2006.01)
(52) U.S. Cl.
CPC .. *C07K 1/145* (2013.01); *C07K 1/14* (2013.01)
USPC ............................ 530/414; 530/423; 530/350

(58) Field of Classification Search
None
See application file for complete search history.

(56) References Cited

U.S. PATENT DOCUMENTS

| 5,332,805 A | 7/1994 | Carey et al. |
|---|---|---|
| 2003/0166062 A1 | 9/2003 | Gonzalez-Villasenor |
| 2009/0123967 A1* | 5/2009 | Scheibel ...................... 435/69.1 |

FOREIGN PATENT DOCUMENTS

| CN | 1450169 A | 10/2003 |
|---|---|---|
| WO | 03/057720 A2 | 7/2003 |
| WO | 03/102013 A2 | 12/2003 |

OTHER PUBLICATIONS

EMBL—Protein Purification Extraction and Clarification (Accessed Dec. 23, 2013).*
International Search Report for International Application No. PCT/EP2011/001605, 5 pages, mailed Feb. 13, 2012.

* cited by examiner

*Primary Examiner* — James H Alstrum Acevedo
*Assistant Examiner* — Tara Martinez
(74) *Attorney, Agent, or Firm* — Kilpatrick Townsend & Stockton LLP

(57) ABSTRACT

The present invention relates to a method of isolating an insoluble target protein from a suspension of intact or disrupted host cells. The invention also relates to insoluble target proteins which are obtainable by said method, in particular to silk proteins.

19 Claims, 6 Drawing Sheets

SEQUENCE LISTING

```
<160> NUMBER OF SEQ ID NOS: 68

<210> SEQ ID NO 1
<211> LENGTH: 636
<212> TYPE: PRT
<213> ORGANISM: Araneus diadematus
<220> FEATURE:
<223> OTHER INFORMATION: dragline silk polypeptide ADF-3

<400> SEQUENCE: 1

Ala Arg Ala Gly Ser Gly Gln Gln Gly Pro Gly Gln Gln Gly Pro Gly
1               5                   10                  15

Gln Gln Gly Pro Gly Gln Gln Gly Pro Tyr Gly Pro Gly Ala Ser Ala
            20                  25                  30

Ala Ala Ala Ala Ala Gly Gly Tyr Gly Pro Gly Ser Gly Gln Gln Gly
        35                  40                  45

Pro Ser Gln Gln Gly Pro Gly Gln Gln Gly Pro Gly Gly Gln Gly Pro
    50                  55                  60

Tyr Gly Pro Gly Ala Ser Ala Ala Ala Ala Ala Ala Gly Gly Tyr Gly
65                  70                  75                  80

Pro Gly Ser Gly Gln Gln Gly Pro Gly Gln Gly Pro Tyr Gly Pro
                85                  90                  95

Gly Ser Ser Ala Ala Ala Ala Ala Ala Gly Gly Asn Gly Pro Gly Ser
            100                 105                 110

Gly Gln Gln Gly Ala Gly Gln Gln Gly Pro Gly Gln Gln Gly Pro Gly
```

```
                115                 120                 125
Ala Ser Ala Ala Ala Ala Ala Gly Gly Tyr Gly Pro Gly Ser Gly
        130                 135                 140
Gln Gln Gly Pro Gly Gln Gln Gly Pro Gly Gln Gly Pro Tyr Gly
145                 150                 155                 160
Pro Gly Ala Ser Ala Ala Ala Ala Ala Gly Gly Tyr Gly Pro Gly
                165                 170                 175
Ser Gly Gln Gly Pro Gly Gln Gln Gly Pro Gly Gln Gly Pro Tyr
                180                 185                 190
Gly Pro Gly Ala Ser Ala Ala Ala Ala Ala Gly Gly Tyr Gly Pro
            195                 200                 205
Gly Ser Gly Gln Gln Gly Pro Gly Gln Gln Gly Pro Gly Gln Gly
        210                 215                 220
Pro Gly Gly Gln Gly Pro Tyr Gly Pro Gly Ala Ser Ala Ala Ala
225                 230                 235                 240
Ala Ala Gly Gly Tyr Gly Pro Gly Tyr Gly Gln Gln Gly Pro Gly Gln
                245                 250                 255
Gln Gly Pro Gly Gly Gln Gly Pro Tyr Gly Pro Gly Ala Ser Ala Ala
            260                 265                 270
Ser Ala Ala Ser Gly Gly Tyr Gly Pro Gly Ser Gly Gln Gln Gly Pro
        275                 280                 285
Gly Gln Gln Gly Pro Gly Gly Gln Gly Pro Tyr Gly Pro Gly Ala Ser
    290                 295                 300
Ala Ala Ala Ala Ala Ala Gly Gly Tyr Gly Pro Gly Ser Gly Gln Gln
305                 310                 315                 320
Gly Pro Gly Gln Gln Gly Pro Gly Gln Gln Gly Pro Gly Gln Gln Gly
                325                 330                 335
Pro Gly Gly Gln Gly Pro Tyr Gly Pro Gly Ala Ser Ala Ala Ala Ala
                340                 345                 350
Ala Ala Gly Gly Tyr Gly Pro Gly Ser Gly Gln Gln Gly Pro Gly Gln
            355                 360                 365
Gln Gly Pro Gly Gln Gln Gly Pro Gly Gln Gln Gly Pro Gly Gln Gln
        370                 375                 380
Gly Pro Gly Gln Gln Gly Pro Gly Gln Gln Gly Pro Gly Gln Gln Gly
385                 390                 395                 400
Pro Gly Gln Gln Gly Pro Gly Gln Gly Ala Tyr Gly Pro Gly Ala
                405                 410                 415
Ser Ala Ala Ala Gly Ala Ala Gly Gly Tyr Gly Pro Gly Ser Gly Gln
            420                 425                 430
Gln Gly Pro Gly Gln Gln Gly Pro Gly Gln Gln Gly Pro Gly Gln Gln
        435                 440                 445
Gly Pro Gly Gln Gln Gly Pro Gly Gln Gln Gly Pro Gly Gln Gln Gly
    450                 455                 460
Pro Gly Gln Gln Gly Pro Tyr Gly Pro Gly Ala Ser Ala Ala Ala Ala
465                 470                 475                 480
Ala Ala Gly Gly Tyr Gly Pro Gly Ser Gly Gln Gln Gly Pro Gly Gln
                485                 490                 495
Gln Gly Pro Gly Gln Gln Gly Pro Gly Gly Gln Gly Pro Tyr Gly Pro
            500                 505                 510
Gly Ala Ala Ser Ala Ala Val Ser Val Gly Gly Tyr Gly Pro Gln Ser
        515                 520                 525
Ser Ser Val Pro Val Ala Ser Ala Val Ala Ser Arg Leu Ser Ser Pro
    530                 535                 540
```

```
Ala Ala Ser Ser Arg Val Ser Ser Ala Val Ser Ser Leu Val Ser Ser
545                 550                 555                 560

Gly Pro Thr Lys His Ala Ala Leu Ser Asn Thr Ile Ser Ser Val Val
                565                 570                 575

Ser Gln Val Ser Ala Ser Asn Pro Gly Leu Ser Gly Cys Asp Val Leu
                580                 585                 590

Val Gln Ala Leu Leu Glu Val Val Ser Ala Leu Val Ser Ile Leu Gly
                595                 600                 605

Ser Ser Ser Ile Gly Gln Ile Asn Tyr Gly Ala Ser Ala Gln Tyr Thr
610                 615                 620

Gln Met Val Gly Gln Ser Val Ala Gln Ala Leu Ala
625                 630                 635

<210> SEQ ID NO 2
<211> LENGTH: 410
<212> TYPE: PRT
<213> ORGANISM: Araneus diadematus
<220> FEATURE:
<223> OTHER INFORMATION: dragline silk polypeptide ADF-4

<400> SEQUENCE: 2

Ala Gly Ser Ser Ala Ala Ala Ala Ala Ala Ser Gly Ser Gly Gly
1               5                   10                  15

Tyr Gly Pro Glu Asn Gln Gly Pro Ser Gly Pro Val Ala Tyr Gly Pro
                20                  25                  30

Gly Gly Pro Val Ser Ala Ala Ala Ala Ala Ala Gly Ser Gly
                35                  40                  45

Pro Gly Gly Tyr Gly Pro Glu Asn Gln Gly Pro Ser Gly Pro Gly Gly
50                  55                  60

Tyr Gly Pro Gly Gly Ser Gly Ser Ser Ala Ala Ala Ala Ala Ala Ala
65                  70                  75                  80

Ala Ser Gly Pro Gly Gly Tyr Gly Pro Gly Ser Gln Gly Pro Ser Gly
                85                  90                  95

Pro Gly Gly Ser Gly Gly Tyr Gly Pro Gly Ser Gln Gly Ala Ser Gly
                100                 105                 110

Pro Gly Gly Pro Gly Ala Ser Ala Ala Ala Ala Ala Ala Ala Ala
                115                 120                 125

Ala Ser Gly Pro Gly Gly Tyr Gly Pro Gly Ser Gln Gly Pro Ser Gly
                130                 135                 140

Pro Gly Ala Tyr Gly Pro Gly Gly Pro Gly Ser Ser Ala Ala Ala Ala
145                 150                 155                 160

Ala Ala Ala Ala Ser Gly Pro Gly Gly Tyr Gly Pro Gly Ser Gln Gly
                165                 170                 175

Pro Ser Gly Pro Gly Val Tyr Gly Pro Gly Gly Pro Gly Ser Ser Ala
                180                 185                 190

Ala Ala Ala Ala Ala Gly Ser Gly Pro Gly Gly Tyr Gly Pro Glu
                195                 200                 205

Asn Gln Gly Pro Ser Gly Pro Gly Tyr Gly Pro Gly Gly Ser Gly
                210                 215                 220

Ser Ser Ala Ala Ala Ala Ala Ala Ala Ser Gly Pro Gly Gly Tyr
225                 230                 235                 240

Gly Pro Gly Ser Gln Gly Pro Ser Gly Pro Gly Gly Ser Gly Gly Tyr
                245                 250                 255

Gly Pro Gly Ser Gln Gly Gly Ser Gly Pro Gly Ala Ser Ala Ala Ala
                260                 265                 270
```

-continued

```
Ala Ala Ala Ala Ala Ser Gly Pro Gly Gly Tyr Gly Pro Gly Ser Gln
            275                 280                 285

Gly Pro Ser Gly Pro Gly Tyr Gln Gly Pro Ser Gly Pro Gly Ala Tyr
        290                 295                 300

Gly Pro Ser Pro Ser Ala Ser Ala Ser Val Ala Ala Ser Val Tyr Leu
305                 310                 315                 320

Arg Leu Gln Pro Arg Leu Glu Val Ser Ser Ala Val Ser Ser Leu Val
                325                 330                 335

Ser Ser Gly Pro Thr Asn Gly Ala Ala Val Ser Gly Ala Leu Asn Ser
            340                 345                 350

Leu Val Ser Gln Ile Ser Ala Ser Asn Pro Gly Leu Ser Gly Cys Asp
        355                 360                 365

Ala Leu Val Gln Ala Leu Leu Glu Leu Val Ser Ala Leu Val Ala Ile
    370                 375                 380

Leu Ser Ser Ala Ser Ile Gly Gln Val Asn Val Ser Ser Val Ser Gln
385                 390                 395                 400

Ser Thr Gln Met Ile Ser Gln Ala Leu Ser
                405                 410

<210> SEQ ID NO 3
<211> LENGTH: 5
<212> TYPE: PRT
<213> ORGANISM: Artificial Sequence
<220> FEATURE:
<223> OTHER INFORMATION: synthetic silk protein repetitive unit
      consensus sequence, glycine rich peptide motif
<220> FEATURE:
<221> NAME/KEY: VARIANT
<222> LOCATION: (4)...(5)
<223> OTHER INFORMATION: Xaa = any amino acid, preferably Ala, Ser, Gly,
      Tyr, Pro or Gln

<400> SEQUENCE: 3

Gly Pro Gly Xaa Xaa
 1               5

<210> SEQ ID NO 4
<211> LENGTH: 5
<212> TYPE: PRT
<213> ORGANISM: Artificial Sequence
<220> FEATURE:
<223> OTHER INFORMATION: synthetic silk protein repetitive unit

<400> SEQUENCE: 4

Gly Pro Gly Gln Gln
 1               5

<210> SEQ ID NO 5
<211> LENGTH: 5
<212> TYPE: PRT
<213> ORGANISM: Artificial Sequence
<220> FEATURE:
<223> OTHER INFORMATION: synthetic silk protein repetitive unit (ADF-3)

<400> SEQUENCE: 5

Gly Pro Gly Ala Ser
 1               5

<210> SEQ ID NO 6
<211> LENGTH: 5
<212> TYPE: PRT
<213> ORGANISM: Artificial Sequence
<220> FEATURE:
```

```
<223> OTHER INFORMATION: synthetic silk protein repetitive unit (ADF-3)

<400> SEQUENCE: 6

Gly Pro Gly Ser Gly
 1               5

<210> SEQ ID NO 7
<211> LENGTH: 5
<212> TYPE: PRT
<213> ORGANISM: Artificial Sequence
<220> FEATURE:
<223> OTHER INFORMATION: synthetic silk protein repetitive unit (ADF-4)

<400> SEQUENCE: 7

Gly Pro Gly Gly Tyr
 1               5

<210> SEQ ID NO 8
<211> LENGTH: 5
<212> TYPE: PRT
<213> ORGANISM: Artificial Sequence
<220> FEATURE:
<223> OTHER INFORMATION: synthetic silk protein repetitive unit (ADF-4)

<400> SEQUENCE: 8

Gly Pro Gly Gly Pro
 1               5

<210> SEQ ID NO 9
<211> LENGTH: 5
<212> TYPE: PRT
<213> ORGANISM: Artificial Sequence
<220> FEATURE:
<223> OTHER INFORMATION: synthetic silk protein repetitive unit
      (flagelliform protein FLAG)

<400> SEQUENCE: 9

Gly Pro Gly Gly Ala
 1               5

<210> SEQ ID NO 10
<211> LENGTH: 5
<212> TYPE: PRT
<213> ORGANISM: Artificial Sequence
<220> FEATURE:
<223> OTHER INFORMATION: synthetic silk protein repetitive unit
      (elastomeric protein resilin)

<400> SEQUENCE: 10

Gly Pro Gly Gly Gly
 1               5

<210> SEQ ID NO 11
<211> LENGTH: 5
<212> TYPE: PRT
<213> ORGANISM: Artificial Sequence
<220> FEATURE:
<223> OTHER INFORMATION: synthetic silk protein repetitive unit
      (flagelliform protein FLAG)

<400> SEQUENCE: 11

Gly Pro Gly Gly Ser
 1               5

<210> SEQ ID NO 12
<211> LENGTH: 5
<212> TYPE: PRT
```

<213> ORGANISM: Artificial Sequence
<220> FEATURE:
<223> OTHER INFORMATION: synthetic silk protein repetitive unit, Ax
      peptide motif

<400> SEQUENCE: 12

Ala Ala Ala Ala Ala
 1               5

<210> SEQ ID NO 13
<211> LENGTH: 6
<212> TYPE: PRT
<213> ORGANISM: Artificial Sequence
<220> FEATURE:
<223> OTHER INFORMATION: synthetic silk protein repetitive unit, Ax
      peptide motif (ADF-3)

<400> SEQUENCE: 13

Ala Ala Ala Ala Ala Ala
 1               5

<210> SEQ ID NO 14
<211> LENGTH: 7
<212> TYPE: PRT
<213> ORGANISM: Artificial Sequence
<220> FEATURE:
<223> OTHER INFORMATION: synthetic silk protein repetitive unit, Ax
      peptide motif (ADF-4)

<400> SEQUENCE: 14

Ala Ala Ala Ala Ala Ala Ala
 1               5

<210> SEQ ID NO 15
<211> LENGTH: 8
<212> TYPE: PRT
<213> ORGANISM: Artificial Sequence
<220> FEATURE:
<223> OTHER INFORMATION: synthetic silk protein repetitive unit, Ax
      peptide motif (ADF-4)

<400> SEQUENCE: 15

Ala Ala Ala Ala Ala Ala Ala Ala
 1               5

<210> SEQ ID NO 16
<211> LENGTH: 9
<212> TYPE: PRT
<213> ORGANISM: Artificial Sequence
<220> FEATURE:
<223> OTHER INFORMATION: synthetic silk protein repetitive unit, Ax
      peptide motif

<400> SEQUENCE: 16

Ala Ala Ala Ala Ala Ala Ala Ala Ala
 1               5

<210> SEQ ID NO 17
<211> LENGTH: 10
<212> TYPE: PRT
<213> ORGANISM: Artificial Sequence
<220> FEATURE:
<223> OTHER INFORMATION: synthetic silk protein repetitive unit, Ax
      peptide motif (ADF-4)

<400> SEQUENCE: 17

Ala Ala Ala Ala Ala Ala Ala Ala Ala Ala
 1               5                  10

```
<210> SEQ ID NO 18
<211> LENGTH: 9
<212> TYPE: PRT
<213> ORGANISM: Artificial Sequence
<220> FEATURE:
<223> OTHER INFORMATION: synthetic silk protein repetitive unit,
      elastomeric protein resilin peptide motif

<400> SEQUENCE: 18

Gly Gly Arg Pro Ser Asp Thr Tyr Gly
 1               5

<210> SEQ ID NO 19
<211> LENGTH: 9
<212> TYPE: PRT
<213> ORGANISM: Artificial Sequence
<220> FEATURE:
<223> OTHER INFORMATION: synthetic silk protein repetitive unit,
      elastomeric protein resilin peptide motif

<400> SEQUENCE: 19

Gly Gly Arg Pro Ser Ser Ser Tyr Gly
 1               5

<210> SEQ ID NO 20
<211> LENGTH: 24
<212> TYPE: PRT
<213> ORGANISM: Artificial Sequence
<220> FEATURE:
<223> OTHER INFORMATION: synthetic silk protein repetitive unit module A
      based on ADF-3

<400> SEQUENCE: 20

Gly Pro Tyr Gly Pro Gly Ala Ser Ala Ala Ala Ala Ala Ala Gly Gly
 1               5                  10                  15

Tyr Gly Pro Gly Ser Gly Gln Gln
            20

<210> SEQ ID NO 21
<211> LENGTH: 35
<212> TYPE: PRT
<213> ORGANISM: Artificial Sequence
<220> FEATURE:
<223> OTHER INFORMATION: synthetic silk protein repetitive unit module C
      based on ADF-4

<400> SEQUENCE: 21

Gly Ser Ser Ala Ala Ala Ala Ala Ala Ala Ser Gly Pro Gly Gly
 1               5                  10                  15

Tyr Gly Pro Glu Asn Gln Gly Pro Ser Gly Pro Gly Gly Tyr Gly Pro
            20                  25                  30

Gly Gly Pro
        35

<210> SEQ ID NO 22
<211> LENGTH: 20
<212> TYPE: PRT
<213> ORGANISM: Artificial Sequence
<220> FEATURE:
<223> OTHER INFORMATION: synthetic silk protein repetitive unit module Q
      based on ADF-3

<400> SEQUENCE: 22

Gly Pro Gly Gln Gln Gly Pro Gly Gln Gln Gly Pro Gly Gln Gln Gly
 1               5                  10                  15
```

Pro Gly Gln Gln
        20

<210> SEQ ID NO 23
<211> LENGTH: 27
<212> TYPE: PRT
<213> ORGANISM: Artificial Sequence
<220> FEATURE:
<223> OTHER INFORMATION: synthetic silk protein repetitive unit module K
      based on flagelliform protein FLAG of the spider
      Nephila clavipes

<400> SEQUENCE: 23

Gly Pro Gly Gly Ala Gly Gly Pro Tyr Gly Pro Gly Gly Ala Gly Gly
1               5                   10                  15

Pro Tyr Gly Pro Gly Gly Ala Gly Gly Pro Tyr
            20                  25

<210> SEQ ID NO 24
<211> LENGTH: 28
<212> TYPE: PRT
<213> ORGANISM: Artificial Sequence
<220> FEATURE:
<223> OTHER INFORMATION: synthetic silk protein repetitive unit module
      sp based on flagelliform protein FLAG of the spider
      Nephila clavipes

<400> SEQUENCE: 24

Gly Gly Thr Thr Ile Ile Glu Asp Leu Asp Ile Thr Ile Asp Gly Ala
1               5                   10                  15

Asp Gly Pro Ile Thr Ile Ser Glu Glu Leu Thr Ile
            20                  25

<210> SEQ ID NO 25
<211> LENGTH: 34
<212> TYPE: PRT
<213> ORGANISM: Artificial Sequence
<220> FEATURE:
<223> OTHER INFORMATION: synthetic silk protein repetitive unit module
      S based on arthropod elestomeric protein resilin

<400> SEQUENCE: 25

Pro Gly Ser Ser Ala Ala Ala Ala Ala Ala Ala Ser Gly Pro Gly
1               5                   10                  15

Gln Gly Gln Gly Gln Gly Gln Gly Gln Gly Gly Arg Pro Ser Asp Thr
            20                  25                  30

Tyr Gly

<210> SEQ ID NO 26
<211> LENGTH: 39
<212> TYPE: PRT
<213> ORGANISM: Artificial Sequence
<220> FEATURE:
<223> OTHER INFORMATION: synthetic silk protein repetitive unit module R
      based on arthropod elestomeric protein resilin

<400> SEQUENCE: 26

Ser Ala Ala Ala Ala Ala Ala Ala Ala Gly Pro Gly Gly Gly Asn Gly
1               5                   10                  15

Gly Arg Pro Ser Asp Thr Tyr Gly Ala Pro Gly Gly Gly Asn Gly Gly
            20                  25                  30

Arg Pro Ser Ser Ser Tyr Gly
            35

```
<210> SEQ ID NO 27
<211> LENGTH: 18
<212> TYPE: PRT
<213> ORGANISM: Artificial Sequence
<220> FEATURE:
<223> OTHER INFORMATION: synthetic silk protein repetitive unit module X
      based on flagelliform protein FLAG of the spider
      Nephila clavipes

<400> SEQUENCE: 27

Gly Gly Ala Gly Gly Ala Gly Gly Ala Gly Gly Ser Gly Gly Ala Gly
 1               5                  10                  15

Gly Ser

<210> SEQ ID NO 28
<211> LENGTH: 30
<212> TYPE: PRT
<213> ORGANISM: Artificial Sequence
<220> FEATURE:
<223> OTHER INFORMATION: synthetic silk protein repetitive unit module Y
      based on flagelliform protein FLAG of the spider
      Nephila clavipes

<400> SEQUENCE: 28

Gly Pro Gly Gly Ala Gly Pro Gly Gly Tyr Gly Pro Gly Gly Ser Gly
 1               5                  10                  15

Pro Gly Gly Tyr Gly Pro Gly Gly Ser Gly Pro Gly Gly Tyr
            20                  25                  30

<210> SEQ ID NO 29
<211> LENGTH: 24
<212> TYPE: PRT
<213> ORGANISM: Artificial Sequence
<220> FEATURE:
<223> OTHER INFORMATION: synthetic silk protein repetitive unit module
      C-A

<400> SEQUENCE: 29

Gly Pro Tyr Gly Pro Gly Ala Ser Ala Ala Ala Ala Ala Ala Gly Gly
 1               5                  10                  15

Tyr Gly Pro Gly Cys Gly Gln Gln
            20

<210> SEQ ID NO 30
<211> LENGTH: 24
<212> TYPE: PRT
<213> ORGANISM: Artificial Sequence
<220> FEATURE:
<223> OTHER INFORMATION: synthetic silk protein repetitive unit module
      K-A

<400> SEQUENCE: 30

Gly Pro Tyr Gly Pro Gly Ala Ser Ala Ala Ala Ala Ala Ala Gly Gly
 1               5                  10                  15

Tyr Gly Pro Gly Lys Gly Gln Gln
            20

<210> SEQ ID NO 31
<211> LENGTH: 35
<212> TYPE: PRT
<213> ORGANISM: Artificial Sequence
<220> FEATURE:
<223> OTHER INFORMATION: synthetic silk protein repetitive unit module
      C-C

<400> SEQUENCE: 31
```

-continued

```
Gly Ser Ser Ala Ala Ala Ala Ala Ala Ala Ser Gly Pro Gly Gly
1               5                   10                  15

Tyr Gly Pro Glu Asn Gln Gly Pro Cys Gly Pro Gly Tyr Gly Pro
            20                  25                  30

Gly Gly Pro
        35

<210> SEQ ID NO 32
<211> LENGTH: 35
<212> TYPE: PRT
<213> ORGANISM: Artificial Sequence
<220> FEATURE:
<223> OTHER INFORMATION: synthetic silk protein repetitive unit module
      K1-C

<400> SEQUENCE: 32

Gly Ser Ser Ala Ala Ala Ala Ala Ala Ala Ser Gly Pro Gly Gly
1               5                   10                  15

Tyr Gly Pro Glu Asn Gln Gly Pro Lys Gly Pro Gly Tyr Gly Pro
            20                  25                  30

Gly Gly Pro
        35

<210> SEQ ID NO 33
<211> LENGTH: 35
<212> TYPE: PRT
<213> ORGANISM: Artificial Sequence
<220> FEATURE:
<223> OTHER INFORMATION: synthetic silk protein repetitive unit module
      K2-C

<400> SEQUENCE: 33

Gly Ser Ser Ala Ala Ala Ala Ala Ala Ala Ser Gly Pro Gly Gly
1               5                   10                  15

Tyr Gly Pro Lys Asn Gln Gly Pro Ser Gly Pro Gly Tyr Gly Pro
            20                  25                  30

Gly Gly Pro
        35

<210> SEQ ID NO 34
<211> LENGTH: 35
<212> TYPE: PRT
<213> ORGANISM: Artificial Sequence
<220> FEATURE:
<223> OTHER INFORMATION: synthetic silk protein repetitive unit module
      KC-C

<400> SEQUENCE: 34

Gly Ser Ser Ala Ala Ala Ala Ala Ala Ala Ser Gly Pro Gly Gly
1               5                   10                  15

Tyr Gly Pro Lys Asn Gln Gly Pro Cys Gly Pro Gly Tyr Gly Pro
            20                  25                  30

Gly Gly Pro
        35

<210> SEQ ID NO 35
<211> LENGTH: 13
<212> TYPE: PRT
<213> ORGANISM: Artificial Sequence
<220> FEATURE:
<223> OTHER INFORMATION: synthetic amino terminal and/or carboxy
      terminal CYS1-TAG
```

```
<400> SEQUENCE: 35

Gly Cys Gly Gly Gly Gly Gly Ser Gly Gly Gly Gly
1               5                   10

<210> SEQ ID NO 36
<211> LENGTH: 8
<212> TYPE: PRT
<213> ORGANISM: Artificial Sequence
<220> FEATURE:
<223> OTHER INFORMATION: synthetic amino terminal and/or carboxy
      terminal CYS2-TAG

<400> SEQUENCE: 36

Gly Cys Gly Gly Gly Gly Gly Gly
1               5

<210> SEQ ID NO 37
<211> LENGTH: 14
<212> TYPE: PRT
<213> ORGANISM: Artificial Sequence
<220> FEATURE:
<223> OTHER INFORMATION: synthetic amino terminal and/or carboxy
      terminal CYS3-TAG

<400> SEQUENCE: 37

Gly Cys Gly Gly Ser Gly Gly Gly Gly Ser Gly Gly Gly Gly
1               5                   10

<210> SEQ ID NO 38
<211> LENGTH: 13
<212> TYPE: PRT
<213> ORGANISM: Artificial Sequence
<220> FEATURE:
<223> OTHER INFORMATION: synthetic amino terminal and/or carboxy
      terminal LYS1-TAG

<400> SEQUENCE: 38

Gly Lys Gly Gly Gly Gly Gly Gly Ser Gly Gly Gly Gly
1               5                   10

<210> SEQ ID NO 39
<211> LENGTH: 8
<212> TYPE: PRT
<213> ORGANISM: Artificial Sequence
<220> FEATURE:
<223> OTHER INFORMATION: synthetic amino terminal and/or carboxy
      terminal LYS2-TAG

<400> SEQUENCE: 39

Gly Lys Gly Gly Gly Gly Gly Gly
1               5

<210> SEQ ID NO 40
<211> LENGTH: 5
<212> TYPE: PRT
<213> ORGANISM: Artificial Sequence
<220> FEATURE:
<223> OTHER INFORMATION: synthetic silk protein repetitive unit
      (elastomeric protein resilin)

<400> SEQUENCE: 40

Gly Pro Gly Gln Gly
1               5

<210> SEQ ID NO 41
<211> LENGTH: 124
<212> TYPE: PRT
```

-continued

<213> ORGANISM: Artificial Sequence
<220> FEATURE:
<223> OTHER INFORMATION: synthetic silk protein non-repetitive (NR) unit
      NR3 based on ADF-3

<400> SEQUENCE: 41

Gly Ala Ala Ser Ala Ala Val Ser Val Gly Gly Tyr Gly Pro Gln Ser
1               5                   10                  15

Ser Ser Ala Pro Val Ala Ser Ala Ala Ala Ser Arg Leu Ser Ser Pro
            20                  25                  30

Ala Ala Ser Ser Arg Val Ser Ser Ala Val Ser Ser Leu Val Ser Ser
        35                  40                  45

Gly Pro Thr Asn Gln Ala Ala Leu Ser Asn Thr Ile Ser Ser Val Val
    50                  55                  60

Ser Gln Val Ser Ala Ser Asn Pro Gly Leu Ser Gly Cys Asp Val Leu
65                  70                  75                  80

Val Gln Ala Leu Leu Glu Val Val Ser Ala Leu Val Ser Ile Leu Gly
                85                  90                  95

Ser Ser Ser Ile Gly Gln Ile Asn Tyr Gly Ala Ser Ala Gln Tyr Thr
            100                 105                 110

Gln Met Val Gly Gln Ser Val Ala Gln Ala Leu Ala
        115                 120

<210> SEQ ID NO 42
<211> LENGTH: 109
<212> TYPE: PRT
<213> ORGANISM: Artificial Sequence
<220> FEATURE:
<223> OTHER INFORMATION: synthetic silk protein non-repetitive (NR) unit
      NR4 based on ADF-4

<400> SEQUENCE: 42

Gly Ala Tyr Gly Pro Ser Pro Ser Ala Ser Ala Ser Val Ala Ala Ser
1               5                   10                  15

Arg Leu Ser Ser Pro Ala Ala Ser Ser Arg Val Ser Ser Ala Val Ser
            20                  25                  30

Ser Leu Val Ser Ser Gly Pro Thr Asn Gly Ala Ala Val Ser Gly Ala
        35                  40                  45

Leu Asn Ser Leu Val Ser Gln Ile Ser Ala Ser Asn Pro Gly Leu Ser
    50                  55                  60

Gly Cys Asp Ala Leu Val Gln Ala Leu Leu Glu Leu Val Ser Ala Leu
65                  70                  75                  80

Val Ala Ile Leu Ser Ser Ala Ser Ile Gly Gln Val Asn Val Ser Ser
                85                  90                  95

Val Ser Gln Ser Thr Gln Met Ile Ser Gln Ala Leu Ser
            100                 105

<210> SEQ ID NO 43
<211> LENGTH: 747
<212> TYPE: PRT
<213> ORGANISM: Araneus diadematus
<220> FEATURE:
<223> OTHER INFORMATION: silk protein MaSp I

<400> SEQUENCE: 43

Gln Gly Ala Gly Ala Ala Ala Ala Ala Ala Gly Gly Ala Gly Gln Gly
1               5                   10                  15

Gly Tyr Gly Gly Leu Gly Gly Gln Gly Ala Gly Gln Gly Gly Tyr Gly
            20                  25                  30

```
Gly Leu Gly Gly Gln Gly Ala Gly Gln Gly Ala Gly Ala Ala Ala
         35                  40                  45

Ala Ala Ala Gly Gly Ala Gly Gln Gly Gly Tyr Gly Gly Leu Gly Ser
 50                  55                  60

Gln Gly Ala Gly Arg Gly Gly Gln Gly Ala Gly Ala Ala Ala Ala Ala
 65                  70                  75                  80

Ala Gly Gly Ala Gly Gln Gly Gly Tyr Gly Gly Leu Gly Ser Gln Gly
             85                  90                  95

Ala Gly Arg Gly Gly Leu Gly Gly Gln Gly Ala Gly Ala Ala Ala Ala
             100                 105                 110

Ala Ala Ala Gly Gly Ala Gly Gln Gly Gly Tyr Gly Gly Leu Gly Asn
             115                 120                 125

Gln Gly Ala Gly Arg Gly Gly Gln Gly Ala Ala Ala Ala Ala Ala Gly
 130                 135                 140

Gly Ala Gly Gln Gly Gly Tyr Gly Gly Leu Gly Ser Gln Gly Ala Gly
 145                 150                 155                 160

Arg Gly Gly Leu Gly Gly Gln Gly Ala Gly Ala Ala Ala Ala Ala Ala
             165                 170                 175

Gly Gly Ala Gly Gln Gly Gly Tyr Gly Gly Leu Gly Gly Gln Gly Ala
             180                 185                 190

Gly Gln Gly Gly Tyr Gly Gly Leu Gly Ser Gln Gly Ala Gly Arg Gly
             195                 200                 205

Gly Leu Gly Gly Gln Gly Ala Gly Ala Ala Ala Ala Ala Ala Ala Gly
             210                 215                 220

Gly Ala Gly Gln Gly Gly Leu Gly Gly Gln Gly Ala Gly Gln Gly Ala
 225                 230                 235                 240

Gly Ala Ser Ala Ala Ala Ala Gly Gly Ala Gly Gln Gly Gly Tyr Gly
             245                 250                 255

Gly Leu Gly Ser Gln Gly Ala Gly Arg Gly Gly Glu Gly Ala Gly Ala
             260                 265                 270

Ala Ala Ala Ala Ala Gly Gly Ala Gly Gln Gly Gly Tyr Gly Gly Leu
             275                 280                 285

Gly Gly Gln Gly Ala Gly Gln Gly Gly Tyr Gly Gly Leu Gly Ser Gln
 290                 295                 300

Gly Ala Gly Arg Gly Gly Leu Gly Gly Gln Gly Ala Gly Ala Ala Ala
 305                 310                 315                 320

Ala Gly Gly Ala Gly Gln Gly Gly Leu Gly Gly Gln Gly Ala Gly Gln
             325                 330                 335

Gly Ala Gly Ala Ala Ala Ala Ala Gly Gly Ala Gly Gln Gly Gly
             340                 345                 350

Tyr Gly Gly Leu Gly Ser Gln Gly Ala Gly Arg Gly Gly Leu Gly Gly
             355                 360                 365

Gln Gly Ala Gly Ala Val Ala Ala Ala Ala Gly Gly Ala Gly Gln
 370                 375                 380

Gly Gly Tyr Gly Gly Leu Gly Ser Gln Gly Ala Gly Arg Gly Gly Gln
 385                 390                 395                 400

Gly Ala Gly Ala Ala Ala Ala Ala Gly Gly Ala Gly Gln Arg Gly
             405                 410                 415

Tyr Gly Gly Leu Gly Asn Gln Gly Ala Gly Arg Gly Gly Leu Gly Gly
             420                 425                 430

Gln Gly Ala Gly Ala Ala Ala Ala Ala Ala Gly Gly Ala Gly Gln
 435                 440                 445

Gly Gly Tyr Gly Gly Leu Gly Asn Gln Gly Ala Gly Arg Gly Gly Gln
```

```
                450                 455                 460
Gly Ala Ala Ala Ala Gly Gly Ala Gly Gln Gly Gly Tyr Gly Gly
465                 470                 475                 480

Leu Gly Ser Gln Gly Ala Gly Arg Gly Gly Gln Gly Ala Gly Ala
                485                 490                 495

Ala Ala Ala Ala Val Gly Ala Gly Gln Glu Gly Ile Arg Gly Gln
                500                 505                 510

Ala Gly Gln Gly Gly Tyr Gly Gly Leu Gly Ser Gln Gly Ser Gly
                515                 520                 525

Gly Gly Leu Gly Gly Gln Gly Ala Gly Ala Ala Ala Ala Ala Gly
                530                 535                 540

Gly Ala Gly Gln Gly Gly Leu Gly Gly Gln Gly Ala Gly Gln Gly Ala
545                 550                 555                 560

Gly Ala Ala Ala Ala Ala Gly Gly Val Arg Gln Gly Gly Tyr Gly
                565                 570                 575

Gly Leu Gly Ser Gln Gly Ala Gly Arg Gly Gly Gln Gly Ala Gly Ala
                580                 585                 590

Ala Ala Ala Ala Gly Gly Ala Gly Gln Gly Gly Tyr Gly Gly Leu
                595                 600                 605

Gly Gly Gln Gly Val Gly Arg Gly Gly Leu Gly Gly Gln Gly Ala Gly
                610                 615                 620

Ala Ala Ala Ala Gly Gly Ala Gly Gln Gly Gly Tyr Gly Gly Val Gly
625                 630                 635                 640

Ser Gly Ala Ser Ala Ala Ser Ala Ala Ala Ser Arg Leu Ser Ser Pro
                645                 650                 655

Gln Ala Ser Ser Arg Val Ser Ser Ala Val Ser Asn Leu Val Ala Ser
                660                 665                 670

Gly Pro Thr Asn Ser Ala Ala Leu Ser Ser Thr Ile Ser Asn Val Val
                675                 680                 685

Ser Gln Ile Gly Ala Ser Asn Pro Gly Leu Ser Gly Cys Asp Val Leu
                690                 695                 700

Ile Gln Ala Leu Leu Glu Val Val Ser Ala Leu Ile Gln Ile Leu Gly
705                 710                 715                 720

Ser Ser Ser Ile Gly Gln Val Asn Tyr Gly Ser Ala Gly Gln Ala Thr
                725                 730                 735

Gln Ile Val Gly Gln Ser Val Tyr Gln Ala Leu
                740                 745

<210> SEQ ID NO 44
<211> LENGTH: 627
<212> TYPE: PRT
<213> ORGANISM: Araneus diadematus
<220> FEATURE:
<223> OTHER INFORMATION: silk protein MaSp II

<400> SEQUENCE: 44

Pro Gly Gly Tyr Gly Pro Gly Gln Gln Gly Pro Gly Gly Tyr Gly Pro
1               5                   10                  15

Gly Gln Gln Gly Pro Ser Gly Pro Gly Ser Ala Ala Ala Ala Ala Ala
                20                  25                  30

Ala Ala Ala Ala Gly Pro Gly Gly Tyr Gly Pro Gly Gln Gln Gly Pro
                35                  40                  45

Gly Gly Tyr Gly Pro Gly Gln Gln Gly Pro Gly Arg Tyr Gly Pro Gly
                50                  55                  60

Gln Gln Gly Pro Ser Gly Pro Gly Ser Ala Ala Ala Ala Ala Ala Gly
```

```
                65                  70                  75                  80
Ser Gly Gln Gln Gly Pro Gly Gly Tyr Gly Pro Arg Gln Gln Gly Pro
                        85                  90                  95
Gly Gly Tyr Gly Gln Gly Gln Gly Pro Ser Gly Pro Gly Ser Ala
                100                 105                 110
Ala Ala Ala Ser Ala Ala Ala Ser Ala Glu Ser Gly Gln Gln Gly Pro
                115                 120                 125
Gly Gly Tyr Gly Pro Gly Gln Gly Pro Gly Tyr Gly Pro Gly
            130                 135                 140
Gln Gln Gly Pro Gly Gly Tyr Gly Pro Gly Gln Gln Gly Pro Ser Gly
145                 150                 155                 160
Pro Gly Ser Ala Ala Ala Ala Ala Ala Ser Gly Pro Gly Gln
                165                 170                 175
Gln Gly Pro Gly Gly Tyr Gly Pro Gly Gln Gln Gly Pro Gly Gly Tyr
                180                 185                 190
Gly Pro Gly Gln Gln Gly Pro Ser Gly Pro Gly Ser Ala Ala Ala Ala
            195                 200                 205
Ala Ala Ala Ala Ser Gly Pro Gly Gln Gln Gly Pro Gly Gly Tyr Gly
210                 215                 220
Pro Gly Gln Gln Gly Pro Gly Gly Tyr Gly Pro Gly Gln Gln Gly Leu
225                 230                 235                 240
Ser Gly Pro Gly Ser Ala Ala Ala Ala Ala Ala Gly Pro Gly Gln
                245                 250                 255
Gln Gly Pro Gly Gly Tyr Gly Pro Gly Gln Gln Gly Pro Ser Gly Pro
                260                 265                 270
Gly Ser Ala Ala Ala Ala Ala Ala Ala Gly Pro Gly Gly Tyr
            275                 280                 285
Gly Pro Gly Gln Gln Gly Pro Gly Gly Tyr Gly Pro Gly Gln Gln Gly
            290                 295                 300
Pro Ser Gly Ala Gly Ser Ala Ala Ala Ala Ala Gly Pro Gly
305                 310                 315                 320
Gln Gln Gly Leu Gly Gly Tyr Gly Pro Gly Gln Gln Gly Pro Gly Gly
                325                 330                 335
Tyr Gly Pro Gly Gln Gln Gly Pro Gly Gly Tyr Gly Pro Gly Ser Ala
                340                 345                 350
Ser Ala Ala Ala Ala Ala Gly Pro Gly Gln Gln Gly Pro Gly Gly
            355                 360                 365
Tyr Gly Pro Gly Gln Gln Gly Pro Ser Gly Pro Gly Ser Ala Ser Ala
            370                 375                 380
Ala Ala Ala Ala Ala Ala Gly Pro Gly Gly Tyr Gly Pro Gly Gln
385                 390                 395                 400
Gln Gly Pro Gly Gly Tyr Ala Pro Gly Gln Gln Gly Pro Ser Gly Pro
                405                 410                 415
Gly Ser Ala Ser Ala Ala Ala Ala Ala Ala Gly Pro Gly Gly
            420                 425                 430
Tyr Gly Pro Gly Gln Gln Gly Pro Gly Gly Tyr Ala Pro Gly Gln Gln
            435                 440                 445
Gly Pro Ser Gly Pro Gly Ser Ala Ala Ala Ala Ala Ala Ala Ala
            450                 455                 460
Gly Pro Gly Gly Tyr Gly Pro Ala Gln Gln Gly Pro Ser Gly Pro Gly
465                 470                 475                 480
Ile Ala Ala Ser Ala Ala Ser Ala Gly Pro Gly Gly Tyr Gly Pro Ala
                485                 490                 495
```

```
Gln Gln Gly Pro Ala Gly Tyr Gly Pro Gly Ser Ala Val Ala Ala Ser
            500                 505                 510

Ala Gly Ala Gly Ser Ala Gly Tyr Gly Pro Gly Ser Gln Ala Ser Ala
        515                 520                 525

Ala Ala Ser Arg Leu Ala Ser Pro Asp Ser Gly Ala Arg Val Ala Ser
    530                 535                 540

Ala Val Ser Asn Leu Val Ser Ser Gly Pro Thr Ser Ser Ala Ala Leu
545                 550                 555                 560

Ser Ser Val Ile Ser Asn Ala Val Ser Gln Ile Gly Ala Ser Asn Pro
                565                 570                 575

Gly Leu Ser Gly Cys Asp Val Leu Ile Gln Ala Leu Leu Glu Ile Val
            580                 585                 590

Ser Ala Cys Val Thr Ile Leu Ser Ser Ser Ile Gly Gln Val Asn
        595                 600                 605

Tyr Gly Ala Ala Ser Gln Phe Ala Gln Val Gly Gln Ser Val Leu
    610                 615                 620

Ser Ala Phe
625

<210> SEQ ID NO 45
<211> LENGTH: 10
<212> TYPE: PRT
<213> ORGANISM: Artificial Sequence
<220> FEATURE:
<223> OTHER INFORMATION: synthetic silk protein repetitive unit
      consensus sequence
<220> FEATURE:
<221> NAME/KEY: VARIANT
<222> LOCATION: (6)...(10)
<223> OTHER INFORMATION: Ala may be present or absent

<400> SEQUENCE: 45

Ala Ala Ala Ala Ala Ala Ala Ala Ala Ala
1               5                   10

<210> SEQ ID NO 46
<211> LENGTH: 10
<212> TYPE: PRT
<213> ORGANISM: Artificial Sequence
<220> FEATURE:
<223> OTHER INFORMATION: synthetic silk protein repetitive unit
      (GPGXX)n, where n = 2
<220> FEATURE:
<221> NAME/KEY: VARIANT
<222> LOCATION: (4)...(10)
<223> OTHER INFORMATION: Xaa = any amino acid, preferably Ala, Ser, Gly,
      Tyr, Pro or Gln

<400> SEQUENCE: 46

Gly Pro Gly Xaa Xaa Gly Pro Gly Xaa Xaa
1               5                   10

<210> SEQ ID NO 47
<211> LENGTH: 15
<212> TYPE: PRT
<213> ORGANISM: Artificial Sequence
<220> FEATURE:
<223> OTHER INFORMATION: synthetic silk protein repetitive unit
      (GPGXX)n, where n = 3
<220> FEATURE:
<221> NAME/KEY: VARIANT
<222> LOCATION: (4)...(15)
<223> OTHER INFORMATION: Xaa = any amino acid, preferably Ala, Ser, Gly,
      Tyr, Pro or Gln
```

```
<400> SEQUENCE: 47

Gly Pro Gly Xaa Xaa Gly Pro Gly Xaa Xaa Gly Pro Gly Xaa Xaa
1               5                   10                  15

<210> SEQ ID NO 48
<211> LENGTH: 20
<212> TYPE: PRT
<213> ORGANISM: Artificial Sequence
<220> FEATURE:
<223> OTHER INFORMATION: synthetic silk protein repetitive unit
      (GPGXX)n, where n = 4
<220> FEATURE:
<221> NAME/KEY: VARIANT
<222> LOCATION: (4)...(20)
<223> OTHER INFORMATION: Xaa = any amino acid, preferably Ala, Ser, Gly,
      Tyr, Pro or Gln

<400> SEQUENCE: 48

Gly Pro Gly Xaa Xaa Gly Pro Gly Xaa Xaa Gly Pro Gly Xaa Xaa Gly
1               5                   10                  15

Pro Gly Xaa Xaa
            20

<210> SEQ ID NO 49
<211> LENGTH: 25
<212> TYPE: PRT
<213> ORGANISM: Artificial Sequence
<220> FEATURE:
<223> OTHER INFORMATION: synthetic silk protein repetitive unit
      (GPGXX)n, where n = 5
<220> FEATURE:
<221> NAME/KEY: VARIANT
<222> LOCATION: (4)...(25)
<223> OTHER INFORMATION: Xaa = any amino acid, preferably Ala, Ser, Gly,
      Tyr, Pro or Gln

<400> SEQUENCE: 49

Gly Pro Gly Xaa Xaa Gly Pro Gly Xaa Xaa Gly Pro Gly Xaa Xaa Gly
1               5                   10                  15

Pro Gly Xaa Xaa Gly Pro Gly Xaa Xaa
            20                  25

<210> SEQ ID NO 50
<211> LENGTH: 30
<212> TYPE: PRT
<213> ORGANISM: Artificial Sequence
<220> FEATURE:
<223> OTHER INFORMATION: synthetic silk protein repetitive unit
      (GPGXX)n, where n = 6
<220> FEATURE:
<221> NAME/KEY: VARIANT
<222> LOCATION: (4)...(30)
<223> OTHER INFORMATION: Xaa = any amino acid, preferably Ala, Ser, Gly,
      Tyr, Pro or Gln

<400> SEQUENCE: 50

Gly Pro Gly Xaa Xaa Gly Pro Gly Xaa Xaa Gly Pro Gly Xaa Xaa Gly
1               5                   10                  15

Pro Gly Xaa Xaa Gly Pro Gly Xaa Xaa Gly Pro Gly Xaa Xaa
            20                  25                  30

<210> SEQ ID NO 51
<211> LENGTH: 35
<212> TYPE: PRT
<213> ORGANISM: Artificial Sequence
<220> FEATURE:
<223> OTHER INFORMATION: synthetic silk protein repetitive unit
      (GPGXX)n, where n = 7
```

```
<220> FEATURE:
<221> NAME/KEY: VARIANT
<222> LOCATION: (4)...(35)
<223> OTHER INFORMATION: Xaa = any amino acid, preferably Ala, Ser, Gly,
      Tyr, Pro or Gln

<400> SEQUENCE: 51

Gly Pro Gly Xaa Xaa Gly Pro Gly Xaa Xaa Gly Pro Gly Xaa Xaa Gly
 1               5                  10                  15

Pro Gly Xaa Xaa Gly Pro Gly Xaa Xaa Gly Pro Gly Xaa Xaa Gly Pro
            20                  25                  30

Gly Xaa Xaa
        35

<210> SEQ ID NO 52
<211> LENGTH: 40
<212> TYPE: PRT
<213> ORGANISM: Artificial Sequence
<220> FEATURE:
<223> OTHER INFORMATION: synthetic silk protein repetitive unit
      (GPGXX)n, where n = 8
<220> FEATURE:
<221> NAME/KEY: VARIANT
<222> LOCATION: (4)...(40)
<223> OTHER INFORMATION: Xaa = any amino acid, preferably Ala, Ser, Gly,
      Tyr, Pro or Gln

<400> SEQUENCE: 52

Gly Pro Gly Xaa Xaa Gly Pro Gly Xaa Xaa Gly Pro Gly Xaa Xaa Gly
 1               5                  10                  15

Pro Gly Xaa Xaa Gly Pro Gly Xaa Xaa Gly Pro Gly Xaa Xaa Gly Pro
            20                  25                  30

Gly Xaa Xaa Gly Pro Gly Xaa Xaa
        35                  40

<210> SEQ ID NO 53
<211> LENGTH: 6
<212> TYPE: PRT
<213> ORGANISM: Artificial Sequence
<220> FEATURE:
<223> OTHER INFORMATION: synthetic silk protein repetitive unit (GGX)n,
      where n = 2
<220> FEATURE:
<221> NAME/KEY: VARIANT
<222> LOCATION: (3)...(6)
<223> OTHER INFORMATION: Xaa = any amino acid, preferably Tyr, Pro, Arg,
      Ser, Ala, Thr, Asn or Gln, more preferably Tyr,
      Pro or Gln

<400> SEQUENCE: 53

Gly Gly Xaa Gly Gly Xaa
 1               5

<210> SEQ ID NO 54
<211> LENGTH: 9
<212> TYPE: PRT
<213> ORGANISM: Artificial Sequence
<220> FEATURE:
<223> OTHER INFORMATION: synthetic silk protein repetitive unit (GGX)n,
      where n = 3
<220> FEATURE:
<221> NAME/KEY: VARIANT
<222> LOCATION: (3)...(9)
<223> OTHER INFORMATION: Xaa = any amino acid, preferably Tyr, Pro, Arg,
      Ser, Ala, Thr, Asn or Gln, more preferably Tyr,
      Pro or Gln

<400> SEQUENCE: 54
```

Gly Gly Xaa Gly Gly Xaa Gly Gly Xaa
1               5

<210> SEQ ID NO 55
<211> LENGTH: 12
<212> TYPE: PRT
<213> ORGANISM: Artificial Sequence
<220> FEATURE:
<223> OTHER INFORMATION: synthetic silk protein repetitive unit (GGX)n,
      where n = 4
<220> FEATURE:
<221> NAME/KEY: VARIANT
<222> LOCATION: (3)...(12)
<223> OTHER INFORMATION: Xaa = any amino acid, preferably Tyr, Pro, Arg,
      Ser, Ala, Thr, Asn or Gln, more preferably Tyr,
      Pro or Gln

<400> SEQUENCE: 55

Gly Gly Xaa Gly Gly Xaa Gly Gly Xaa Gly Gly Xaa
1               5                   10

<210> SEQ ID NO 56
<211> LENGTH: 15
<212> TYPE: PRT
<213> ORGANISM: Artificial Sequence
<220> FEATURE:
<223> OTHER INFORMATION: synthetic silk protein repetitive unit (GGX)n,
      where n = 5
<220> FEATURE:
<221> NAME/KEY: VARIANT
<222> LOCATION: (3)...(15)
<223> OTHER INFORMATION: Xaa = any amino acid, preferably Tyr, Pro, Arg,
      Ser, Ala, Thr, Asn or Gln, more preferably Tyr,
      Pro or Gln

<400> SEQUENCE: 56

Gly Gly Xaa Gly Gly Xaa Gly Gly Xaa Gly Gly Xaa Gly Gly Xaa
1               5                   10                  15

<210> SEQ ID NO 57
<211> LENGTH: 18
<212> TYPE: PRT
<213> ORGANISM: Artificial Sequence
<220> FEATURE:
<223> OTHER INFORMATION: synthetic silk protein repetitive unit (GGX)n,
      where n = 6
<220> FEATURE:
<221> NAME/KEY: VARIANT
<222> LOCATION: (3)...(18)
<223> OTHER INFORMATION: Xaa = any amino acid, preferably Tyr, Pro, Arg,
      Ser, Ala, Thr, Asn or Gln, more preferably Tyr,
      Pro or Gln

<400> SEQUENCE: 57

Gly Gly Xaa Gly Gly Xaa Gly Gly Xaa Gly Gly Xaa Gly Gly Xaa Gly
1               5                   10                  15

Gly Xaa

<210> SEQ ID NO 58
<211> LENGTH: 21
<212> TYPE: PRT
<213> ORGANISM: Artificial Sequence
<220> FEATURE:
<223> OTHER INFORMATION: synthetic silk protein repetitive unit (GGX)n,
      where n = 7
<220> FEATURE:
<221> NAME/KEY: VARIANT
<222> LOCATION: (3)...(21)
<223> OTHER INFORMATION: Xaa = any amino acid, preferably Tyr, Pro, Arg,
      Ser, Ala, Thr, Asn or Gln, more preferably Tyr,
      Pro or Gln

```
<400> SEQUENCE: 58

Gly Gly Xaa Gly Gly Xaa Gly Gly Xaa Gly Gly Xaa Gly Gly Xaa Gly
 1               5                   10                  15

Gly Xaa Gly Gly Xaa
            20

<210> SEQ ID NO 59
<211> LENGTH: 24
<212> TYPE: PRT
<213> ORGANISM: Artificial Sequence
<220> FEATURE:
<223> OTHER INFORMATION: synthetic silk protein repetitive unit (GGX)n,
      where n = 8
<220> FEATURE:
<221> NAME/KEY: VARIANT
<222> LOCATION: (3)...(24)
<223> OTHER INFORMATION: Xaa = any amino acid, preferably Tyr, Pro, Arg,
      Ser, Ala, Thr, Asn or Gln, more preferably Tyr,
      Pro or Gln

<400> SEQUENCE: 59

Gly Gly Xaa Gly Gly Xaa Gly Gly Xaa Gly Gly Xaa Gly Gly Xaa Gly
 1               5                   10                  15

Gly Xaa Gly Gly Xaa Gly Gly Xaa
            20

<210> SEQ ID NO 60
<211> LENGTH: 20
<212> TYPE: PRT
<213> ORGANISM: Artificial Sequence
<220> FEATURE:
<223> OTHER INFORMATION: synthetic silk protein repetitive unit (Ax)n,
      where x = 5-10 and n = 2
<220> FEATURE:
<221> NAME/KEY: VARIANT
<222> LOCATION: (6)...(10)
<223> OTHER INFORMATION: Ala may be present or absent
<220> FEATURE:
<221> NAME/KEY: VARIANT
<222> LOCATION: (16)...(20)
<223> OTHER INFORMATION: Ala may be present or absent

<400> SEQUENCE: 60

Ala Ala Ala Ala Ala Ala Ala Ala Ala Ala Ala Ala Ala Ala Ala Ala
 1               5                   10                  15

Ala Ala Ala Ala
            20

<210> SEQ ID NO 61
<211> LENGTH: 30
<212> TYPE: PRT
<213> ORGANISM: Artificial Sequence
<220> FEATURE:
<223> OTHER INFORMATION: synthetic silk protein repetitive unit (Ax)n,
      where x = 5-10 and n = 3
<220> FEATURE:
<221> NAME/KEY: VARIANT
<222> LOCATION: (6)...(10)
<223> OTHER INFORMATION: Ala may be present or absent
<220> FEATURE:
<221> NAME/KEY: VARIANT
<222> LOCATION: (16)...(20)
<223> OTHER INFORMATION: Ala may be present or absent
<220> FEATURE:
<221> NAME/KEY: VARIANT
<222> LOCATION: (26)...(30)
<223> OTHER INFORMATION: Ala may be present or absent

<400> SEQUENCE: 61
```

```
Ala Ala Ala Ala Ala Ala Ala Ala Ala Ala Ala Ala Ala Ala Ala
 1               5                   10                  15

Ala Ala Ala Ala Ala Ala Ala Ala Ala Ala Ala Ala Ala Ala Ala
                20                  25                  30

<210> SEQ ID NO 62
<211> LENGTH: 40
<212> TYPE: PRT
<213> ORGANISM: Artificial Sequence
<220> FEATURE:
<223> OTHER INFORMATION: synthetic silk protein repetitive unit (Ax)n,
      where x = 5-10 and n = 4
<220> FEATURE:
<221> NAME/KEY: VARIANT
<222> LOCATION: (6)...(10)
<223> OTHER INFORMATION: Ala may be present or absent
<220> FEATURE:
<221> NAME/KEY: VARIANT
<222> LOCATION: (16)...(20)
<223> OTHER INFORMATION: Ala may be present or absent
<220> FEATURE:
<221> NAME/KEY: VARIANT
<222> LOCATION: (26)...(30)
<223> OTHER INFORMATION: Ala may be present or absent
<220> FEATURE:
<221> NAME/KEY: VARIANT
<222> LOCATION: (36)...(40)
<223> OTHER INFORMATION: Ala may be present or absent

<400> SEQUENCE: 62

Ala Ala Ala Ala Ala Ala Ala Ala Ala Ala Ala Ala Ala Ala Ala
 1               5                   10                  15

Ala Ala Ala Ala Ala Ala Ala Ala Ala Ala Ala Ala Ala Ala Ala
                20                  25                  30

Ala Ala Ala Ala Ala Ala Ala Ala
        35                  40

<210> SEQ ID NO 63
<211> LENGTH: 50
<212> TYPE: PRT
<213> ORGANISM: Artificial Sequence
<220> FEATURE:
<223> OTHER INFORMATION: synthetic silk protein repetitive unit (Ax)n,
      where x = 5-10 and n = 5
<220> FEATURE:
<221> NAME/KEY: VARIANT
<222> LOCATION: (6)...(10)
<223> OTHER INFORMATION: Ala may be present or absent
<220> FEATURE:
<221> NAME/KEY: VARIANT
<222> LOCATION: (16)...(20)
<223> OTHER INFORMATION: Ala may be present or absent
<220> FEATURE:
<221> NAME/KEY: VARIANT
<222> LOCATION: (26)...(30)
<223> OTHER INFORMATION: Ala may be present or absent
<220> FEATURE:
<221> NAME/KEY: VARIANT
<222> LOCATION: (36)...(40)
<223> OTHER INFORMATION: Ala may be present or absent
<220> FEATURE:
<221> NAME/KEY: VARIANT
<222> LOCATION: (46)...(50)
<223> OTHER INFORMATION: Ala may be present or absent

<400> SEQUENCE: 63

Ala Ala Ala Ala Ala Ala Ala Ala Ala Ala Ala Ala Ala Ala Ala
 1               5                   10                  15

Ala Ala Ala Ala Ala Ala Ala Ala Ala Ala Ala Ala Ala Ala Ala
                20                  25                  30
```

```
Ala Ala Ala Ala Ala Ala Ala Ala Ala Ala Ala Ala Ala Ala
        35                  40                  45

Ala Ala
    50

<210> SEQ ID NO 64
<211> LENGTH: 60
<212> TYPE: PRT
<213> ORGANISM: Artificial Sequence
<220> FEATURE:
<223> OTHER INFORMATION: synthetic silk protein repetitive unit (Ax)n,
      where x = 5-10 and n = 6
<220> FEATURE:
<221> NAME/KEY: VARIANT
<222> LOCATION: (6)...(10)
<223> OTHER INFORMATION: Ala may be present or absent
<220> FEATURE:
<221> NAME/KEY: VARIANT
<222> LOCATION: (16)...(20)
<223> OTHER INFORMATION: Ala may be present or absent
<220> FEATURE:
<221> NAME/KEY: VARIANT
<222> LOCATION: (26)...(30)
<223> OTHER INFORMATION: Ala may be present or absent
<220> FEATURE:
<221> NAME/KEY: VARIANT
<222> LOCATION: (36)...(40)
<223> OTHER INFORMATION: Ala may be present or absent
<220> FEATURE:
<221> NAME/KEY: VARIANT
<222> LOCATION: (46)...(50)
<223> OTHER INFORMATION: Ala may be present or absent
<220> FEATURE:
<221> NAME/KEY: VARIANT
<222> LOCATION: (56)...(60)
<223> OTHER INFORMATION: Ala may be present or absent

<400> SEQUENCE: 64

Ala Ala Ala Ala Ala Ala Ala Ala Ala Ala Ala Ala Ala Ala Ala
 1               5                  10                  15

Ala Ala Ala Ala Ala Ala Ala Ala Ala Ala Ala Ala Ala Ala Ala
                20                  25                  30

Ala Ala Ala Ala Ala Ala Ala Ala Ala Ala Ala Ala Ala Ala Ala
        35                  40                  45

Ala Ala Ala Ala Ala Ala Ala Ala Ala Ala Ala Ala Ala Ala Ala
    50                  55                  60

<210> SEQ ID NO 65
<211> LENGTH: 70
<212> TYPE: PRT
<213> ORGANISM: Artificial Sequence
<220> FEATURE:
<223> OTHER INFORMATION: synthetic silk protein repetitive unit (Ax)n,
      where x = 5-10 and n = 7
<220> FEATURE:
<221> NAME/KEY: VARIANT
<222> LOCATION: (6)...(10)
<223> OTHER INFORMATION: Ala may be present or absent
<220> FEATURE:
<221> NAME/KEY: VARIANT
<222> LOCATION: (16)...(20)
<223> OTHER INFORMATION: Ala may be present or absent
<220> FEATURE:
<221> NAME/KEY: VARIANT
<222> LOCATION: (26)...(30)
<223> OTHER INFORMATION: Ala may be present or absent
<220> FEATURE:
<221> NAME/KEY: VARIANT
<222> LOCATION: (36)...(40)
<223> OTHER INFORMATION: Ala may be present or absent
<220> FEATURE:
```

```
<221> NAME/KEY: VARIANT
<222> LOCATION: (46)...(50)
<223> OTHER INFORMATION: Ala may be present or absent
<220> FEATURE:
<221> NAME/KEY: VARIANT
<222> LOCATION: (56)...(60)
<223> OTHER INFORMATION: Ala may be present or absent
<220> FEATURE:
<221> NAME/KEY: VARIANT
<222> LOCATION: (66)...(70)
<223> OTHER INFORMATION: Ala may be present or absent

<400> SEQUENCE: 65

Ala Ala Ala Ala Ala Ala Ala Ala Ala Ala Ala Ala Ala Ala Ala Ala
 1               5                  10                  15

Ala Ala Ala Ala Ala Ala Ala Ala Ala Ala Ala Ala Ala Ala Ala Ala
             20                  25                  30

Ala Ala Ala Ala Ala Ala Ala Ala Ala Ala Ala Ala Ala Ala Ala Ala
         35                  40                  45

Ala Ala Ala Ala Ala Ala Ala Ala Ala Ala Ala Ala Ala Ala Ala Ala
     50                  55                  60

Ala Ala Ala Ala Ala Ala
65                  70

<210> SEQ ID NO 66
<211> LENGTH: 80
<212> TYPE: PRT
<213> ORGANISM: Artificial Sequence
<220> FEATURE:
<223> OTHER INFORMATION: synthetic silk protein repetitive unit (Ax)n,
      where x = 5-10 and n = 8
<220> FEATURE:
<221> NAME/KEY: VARIANT
<222> LOCATION: (6)...(10)
<223> OTHER INFORMATION: Ala may be present or absent
<220> FEATURE:
<221> NAME/KEY: VARIANT
<222> LOCATION: (16)...(20)
<223> OTHER INFORMATION: Ala may be present or absent
<220> FEATURE:
<221> NAME/KEY: VARIANT
<222> LOCATION: (26)...(30)
<223> OTHER INFORMATION: Ala may be present or absent
<220> FEATURE:
<221> NAME/KEY: VARIANT
<222> LOCATION: (36)...(40)
<223> OTHER INFORMATION: Ala may be present or absent
<220> FEATURE:
<221> NAME/KEY: VARIANT
<222> LOCATION: (46)...(50)
<223> OTHER INFORMATION: Ala may be present or absent
<220> FEATURE:
<221> NAME/KEY: VARIANT
<222> LOCATION: (56)...(60)
<223> OTHER INFORMATION: Ala may be present or absent
<220> FEATURE:
<221> NAME/KEY: VARIANT
<222> LOCATION: (66)...(70)
<223> OTHER INFORMATION: Ala may be present or absent
<220> FEATURE:
<221> NAME/KEY: VARIANT
<222> LOCATION: (76)...(80)
<223> OTHER INFORMATION: Ala may be present or absent

<400> SEQUENCE: 66

Ala Ala Ala Ala Ala Ala Ala Ala Ala Ala Ala Ala Ala Ala Ala Ala
 1               5                  10                  15

Ala Ala Ala Ala Ala Ala Ala Ala Ala Ala Ala Ala Ala Ala Ala Ala
             20                  25                  30

Ala Ala Ala Ala Ala Ala Ala Ala Ala Ala Ala Ala Ala Ala Ala Ala
```

```
                35                  40                  45
Ala Ala Ala Ala Ala Ala Ala Ala Ala Ala Ala Ala Ala Ala Ala
        50                  55                  60
Ala Ala Ala Ala Ala Ala Ala Ala Ala Ala Ala Ala Ala Ala Ala
65                  70                  75                  80

<210> SEQ ID NO 67
<211> LENGTH: 90
<212> TYPE: PRT
<213> ORGANISM: Artificial Sequence
<220> FEATURE:
<223> OTHER INFORMATION: synthetic silk protein repetitive unit (Ax)n,
      where x = 5-10 and n = 9
<220> FEATURE:
<221> NAME/KEY: VARIANT
<222> LOCATION: (6)...(10)
<223> OTHER INFORMATION: Ala may be present or absent
<220> FEATURE:
<221> NAME/KEY: VARIANT
<222> LOCATION: (16)...(20)
<223> OTHER INFORMATION: Ala may be present or absent
<220> FEATURE:
<221> NAME/KEY: VARIANT
<222> LOCATION: (26)...(30)
<223> OTHER INFORMATION: Ala may be present or absent
<220> FEATURE:
<221> NAME/KEY: VARIANT
<222> LOCATION: (36)...(40)
<223> OTHER INFORMATION: Ala may be present or absent
<220> FEATURE:
<221> NAME/KEY: VARIANT
<222> LOCATION: (46)...(50)
<223> OTHER INFORMATION: Ala may be present or absent
<220> FEATURE:
<221> NAME/KEY: VARIANT
<222> LOCATION: (56)...(60)
<223> OTHER INFORMATION: Ala may be present or absent
<220> FEATURE:
<221> NAME/KEY: VARIANT
<222> LOCATION: (66)...(70)
<223> OTHER INFORMATION: Ala may be present or absent
<220> FEATURE:
<221> NAME/KEY: VARIANT
<222> LOCATION: (76)...(80)
<223> OTHER INFORMATION: Ala may be present or absent
<220> FEATURE:
<221> NAME/KEY: VARIANT
<222> LOCATION: (86)...(90)
<223> OTHER INFORMATION: Ala may be present or absent

<400> SEQUENCE: 67

Ala Ala Ala Ala Ala Ala Ala Ala Ala Ala Ala Ala Ala Ala Ala
1               5                  10                  15
Ala Ala Ala Ala Ala Ala Ala Ala Ala Ala Ala Ala Ala Ala Ala
            20                  25                  30
Ala Ala Ala Ala Ala Ala Ala Ala Ala Ala Ala Ala Ala Ala Ala
        35                  40                  45
Ala Ala Ala Ala Ala Ala Ala Ala Ala Ala Ala Ala Ala Ala Ala
    50                  55                  60
Ala Ala Ala Ala Ala Ala Ala Ala Ala Ala Ala Ala Ala Ala Ala
65                  70                  75                  80
Ala Ala Ala Ala Ala Ala Ala Ala Ala Ala
            85                  90

<210> SEQ ID NO 68
<211> LENGTH: 100
<212> TYPE: PRT
<213> ORGANISM: Artificial Sequence
<220> FEATURE:
```

```
<223> OTHER INFORMATION: synthetic silk protein repetitive unit (Ax)n,
      where x = 5-10 and n = 10
<220> FEATURE:
<221> NAME/KEY: VARIANT
<222> LOCATION: (6)...(10)
<223> OTHER INFORMATION: Ala may be present or absent
<220> FEATURE:
<221> NAME/KEY: VARIANT
<222> LOCATION: (16)...(20)
<223> OTHER INFORMATION: Ala may be present or absent
<220> FEATURE:
<221> NAME/KEY: VARIANT
<222> LOCATION: (26)...(30)
<223> OTHER INFORMATION: Ala may be present or absent
<220> FEATURE:
<221> NAME/KEY: VARIANT
<222> LOCATION: (36)...(40)
<223> OTHER INFORMATION: Ala may be present or absent
<220> FEATURE:
<221> NAME/KEY: VARIANT
<222> LOCATION: (46)...(50)
<223> OTHER INFORMATION: Ala may be present or absent
<220> FEATURE:
<221> NAME/KEY: VARIANT
<222> LOCATION: (56)...(60)
<223> OTHER INFORMATION: Ala may be present or absent
<220> FEATURE:
<221> NAME/KEY: VARIANT
<222> LOCATION: (66)...(70)
<223> OTHER INFORMATION: Ala may be present or absent
<220> FEATURE:
<221> NAME/KEY: VARIANT
<222> LOCATION: (76)...(80)
<223> OTHER INFORMATION: Ala may be present or absent
<220> FEATURE:
<221> NAME/KEY: VARIANT
<222> LOCATION: (86)...(90)
<223> OTHER INFORMATION: Ala may be present or absent
<220> FEATURE:
<221> NAME/KEY: VARIANT
<222> LOCATION: (96)...(100)
<223> OTHER INFORMATION: Ala may be present or absent

<400> SEQUENCE: 68

Ala Ala Ala Ala Ala Ala Ala Ala Ala Ala Ala Ala Ala Ala Ala Ala
 1               5                  10                  15

Ala Ala Ala Ala Ala Ala Ala Ala Ala Ala Ala Ala Ala Ala Ala Ala
            20                  25                  30

Ala Ala Ala Ala Ala Ala Ala Ala Ala Ala Ala Ala Ala Ala Ala Ala
        35                  40                  45

Ala Ala Ala Ala Ala Ala Ala Ala Ala Ala Ala Ala Ala Ala Ala Ala
    50                  55                  60

Ala Ala Ala Ala Ala Ala Ala Ala Ala Ala Ala Ala Ala Ala Ala Ala
65                  70                  75                  80

Ala Ala Ala Ala Ala Ala Ala Ala Ala Ala Ala Ala Ala Ala Ala Ala
            85                  90                  95

Ala Ala Ala Ala
            100
```

SEPARATION OF INSOLUBLE TARGET PROTEINS

Figure 1:
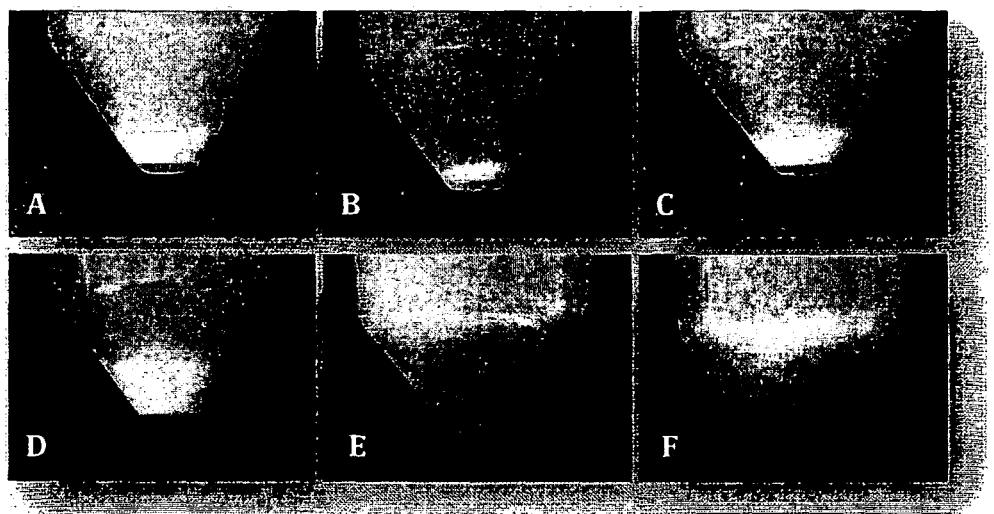

This application is a National Stage of International Application No. PCT/EP2011/001605, filed Mar. 30, 2011, and entitled SEPARATION OF INSOLUBLE TARGET PROTEINS, which is incorporated herein in its entirety.

The present invention relates to a method of isolating an insoluble target protein from a suspension of intact or disrupted host cells. The invention also relates to insoluble target proteins which are obtainable by said method.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 95697-877485.TXT, created on Jul. 23, 2013, 53,248 bytes, machine format IBM-PC, MS-Windows operating system, is hereby incorporated by reference in its entirety for all purposes.

BACKGROUND OF THE INVENTION

Systems for the isolation of target proteins from a suspension of host cells, e.g. microbial cells, and/or from other impurities have been developed earlier and, thus, represent prior art knowledge.

As an example, it is referred to standard protein purification procedures for the purification and isolation of soluble target proteins applying chromatographic techniques like ion-exchange or size-exclusion chromatography (Guide to Protein Purification, Academic Press Vol. 182, 1990). Other applied technologies today are liquid-liquid phase separation and ultra-filtration, among others (Guide to Protein Purification, Academic Press Vol. 182, 1990). With variations, these fundamental purification processes can be modified to purify most proteins required for scientific or industrial purposes, however, they are generally very cost intensive, complex and time consuming.

A special method to handle silk proteins in particular has been described in Huemmerich et al., Biochemistry 2004, 43, 13604-13612. In this publication a technique utilizing heat denaturation of host cell proteins following a target protein precipitation step, but lacking chromatographic purification methods, was applied successfully to purify recombinant spider silk proteins for technical applications. As silk proteins tend to self-aggregate, this method suffers from the loss of a significant fraction of the target protein, which is precipitated and, thus, unavailable for a soluble protein purification method.

Although the described methods work well for most soluble proteins, it is obvious that they bring forth severe disadvantages when handling aggregation prone proteins. Such aggregation prone proteins tend to precipitate in solution over a certain time period yielding stable, often insoluble protein aggregates. These protein aggregates can not be isolated with the described soluble protein fraction purification processes any more. Therefore, the fermentation time and/or the purification time are generally critical parameters to avoid unwanted precipitation. It is known that said protein aggregates can be solubilized using several detergents, however, it is also known that such a solubilization negatively affects the protein yield as well as the protein quality. In addition, a complete solubilization of protein aggregates over a prolonged time period is almost impossible.

Thus, there is a need to develop a purification/isolation method for aggregation prone target proteins and/or already aggregated target proteins which focuses on the separation of the aggregation prone target protein fraction and/or aggregated target protein fraction from the fraction which comprises insoluble host cell proteins and other remnants, without complete solubilization of said target proteins. Such a purification method should allow the isolation of insoluble target proteins from a suspension of host cells, e.g. microbial cells, and/or other cell remnants, in high yields and high quality. Such a purification method should also be cost effective, rapid, easy, and reproducible.

The inventors of the present invention have surprisingly found that the target proteins are insoluble and remain insoluble under certain conditions which are necessary to solubilize all or almost all other insoluble host cell proteins, host cell remnants and/or other potential fermentation-related impurities and that this allows the separation and purification of these target proteins in only a few purification steps without losing significant amounts of said target proteins due to unwanted solubilization of said target proteins or due to other cross-reactions.

Surprisingly, a purification of insoluble target proteins to preferably at least 80% purity can be achieved by separating the insoluble target proteins from the solubilized insoluble host cell parts according to the method of the present invention. Even if some insoluble host cell parts are not completely dissolved but remain in suspension, efficient separation can nevertheless be achieved as the specific density of these suspended host cell parts is lower than that of the insoluble target proteins, which allows efficient separation by centrifugation, sedimentation and/or filtration.

The method of the present invention offers several striking advantages compared to the known purification techniques. For example, the method of the present invention reduces the number of complex purification steps and is, therefore, a fast, reliable, and easy to perform purification method. In addition, said method allows the purification/isolation of the insoluble target proteins in high yield and quality. It allows a drastic cost reduction compared to conventional methods. In addition, said method is environmental friendly.

Although the method of the present invention comprises only a few method steps, it was hitherto completely unforeseeable that certain target proteins are and stay insoluble under the conditions applied. Especially when considered against the background that the applied base concentrations (~0.1 M NaOH) are commonly used to wash and clean bioreactors as well as reaction tanks which came in contact with proteins and cells. Thus it is hardly self-evident that these conditions can also be applied to purify insoluble target proteins in large scale.

SUMMARY OF THE INVENTION

In a first aspect, the present invention provides a method of isolating an insoluble target protein from a suspension of intact or disrupted host cells comprising the steps of:
a) providing a suspension of intact or disrupted host cells comprising an insoluble target protein and insoluble host cell parts,
b) adding an aqueous solution of at least one base to said suspension in an amount which is sufficient to disrupt said host cells and/or to solubilize said insoluble host cell parts, and
c) separating the insoluble target protein from the solubilized insoluble host cell parts, wherein in step b) the target protein remains insoluble, and wherein at least 80% of the insoluble host cell parts are solubilized.

In a second aspect, the present invention relates to an insoluble target protein obtainable by the method of the first aspect.

This summary of the invention does not necessarily describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise herein, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

As used in this specification and the appended claims, the singular forms "a", "an", and "the" include plural referents, unless the content clearly dictates otherwise.

Residues in two or more polypeptides are said to "correspond" to each other if the residues occupy an analogous position in the polypeptide structures. It is well known in the art that analogous positions in two or more polypeptides can be determined by aligning the polypeptide sequences based on amino acid sequence or structural similarities. Such alignment tools are well known to the person skilled in the art and can be, for example, obtained on the World Wide Web, e.g., ClustalW (www.ebi.ac.uk/clustalw) or Align (http://www.ebi.ac.uk/emboss/align/index.html) using standard settings, preferably for Align EMBOSS::needle, Matrix: Blosum62, Gap Open 10.0, Gap Extend 0.5.

In a first aspect, the invention provides a method of isolating an insoluble target protein from a suspension of intact or disrupted host cells comprising the steps of:
  a) providing a suspension of intact or disrupted host cells comprising an insoluble target protein and insoluble host cell parts,
  b) adding an aqueous solution of at least one base to said suspension in an amount which is sufficient to disrupt said host cells and/or to solubilize said insoluble host cell parts, and
  c) separating the insoluble target protein from the solubilized insoluble host cell parts,
wherein in step b) the target protein remains insoluble, and wherein at least 80%, preferably at least 85%, more preferably at least 90%, and most preferably at least 95%, or even 100%, of the insoluble host cell parts are solubilized.

For example, the invention provides a method of isolating an insoluble target protein from a suspension of disrupted host cells comprising the steps of:
  a) providing a suspension of disrupted host cells comprising an insoluble target protein and insoluble host cell parts,
  b) adding an aqueous solution of at least one base to said suspension in an amount which is sufficient to solubilize said insoluble host cell parts, and
  c) separating the insoluble target protein from the solubilized insoluble host cell parts,
wherein in step b) the target protein remains insoluble, and wherein at least 80%, preferably at least 85%, more preferably at least 90%, and most preferably at least 95%, or even 100%, of the insoluble host cell parts are solubilized.

Further, for example, the invention provides a method of isolating an insoluble target protein from a suspension of intact host cells comprising the steps of:
  a) providing a suspension of intact host cells comprising an insoluble target protein and insoluble host cell parts,
  b) adding an aqueous solution of at least one base to said suspension in an amount which is sufficient to disrupt said host cells and to solubilize said insoluble host cell parts, and
  c) separating the insoluble target protein from the solubilized insoluble host cell parts,
wherein in step b) the target protein remains insoluble, and wherein at least 80%, preferably at least 85%, more preferably at least 90%, and most preferably at least 95%, or even 100%, of the insoluble host cell parts are solubilized.

The inventors of the present invention have surprisingly found that insoluble target proteins, e.g. spider silk proteins, which are present in a suspension of intact or disrupted host cells, stay insoluble under certain conditions that are required to disrupt intact host cells and/or to solubilize all or almost all other insoluble host cell parts, e.g. insoluble host cell proteins, host cells walls, host cell remnants, or other potential fermentation-related impurities (e.g. fermentation remnants), and that, thus, said insoluble target proteins, e.g. spider silk proteins, can simply be separated and purified from said suspensions in only few purification steps without losing significant protein amounts.

In detail, the inventors of the present invention have unexpectedly found that the separation of insoluble target proteins from insoluble host cell parts can be achieved by adding an aqueous solution comprising at least one base (e.g. NaOH) in a low concentration (e.g. 0.05 M NaOH) to a suspension of intact or disrupted host cells. The inventors have discovered that the aqueous solution comprising at least one base disrupts the host cells and/or solubilizes insoluble host cell proteins and remaining cell debris without affecting the insoluble target protein.

The inventors have further ascertained that following this step, it is solely required to separate the solid phase comprising the insoluble target protein from the liquid phase comprising the solubilized insoluble host cells parts, e.g. by centrifugation and/or filtration, and to optionally wash the target protein precipitate in order to purify the insoluble target protein of interest. The resulting purified insoluble target protein can be directly used for scientific or industrial applications without further processing.

The inventors have surprisingly determined that with the method of the present invention an insoluble target protein having a purity of at least 80%, preferably of at least 85%, or 90%, more preferably of at least 95%, 98%, or 99%, and most preferably of at least 99.9%, or even of 100%, e.g. at least 80, 81, 82, 83, 84, 85, 86, 87, 88, 89, 90, 91, 92, 93, 94, 95, 96, 97, 98, 99, 99.9%, or 100%, may be isolated. The majority of the insoluble target proteins, isolated with the method of the present invention, do not require further purification steps. Accordingly, the method of the present invention represents a very cost-saving and an effective purification method.

The term "host cells", as used herein, refers to cells that comprise a target protein of interest, e.g. a silk protein such as a spider silk protein or a variant thereof. Said target protein, e.g. a silk protein such as a spider silk protein or a variant thereof, may be encoded by a polynucleotide, preferably by an isolated polynucleotide. Said polynucleotide may be found inside the host cells (i) freely dispersed as such, (ii) incorporated in a recombinant vector, or (iii) integrated into the host cells genome or mitochondrial DNA. The host cells may be used for amplification and expression of a polynucleotide that codes for a target protein of interest, e.g. a silk protein such as a spider silk protein or a variant thereof.

The term "isolated polynucleotide", as used herein, refers to a polynucleotide that was (i) isolated from its natural environment, (ii) amplified by polymerase chain reaction, and/or (iii) wholly or partially synthesized, and means a single or double-stranded polymer of deoxyribonucleotide or ribonucleotide bases and includes a DNA and RNA molecule, both sense and anti-sense strand. The term comprises cDNA, genomic DNA, mRNA and recombinant DNA. A polynucleotide may consist of an entire gene, or a portion thereof.

In a preferred embodiment of the present invention, the afore-mentioned polynucleotide is a recombinant polynucleotide encoding the target protein of interest. The term "recombinant polynucleotide" refers to a polynucleotide synthesized or otherwise manipulated in vitro. The target protein which is encoded by said recombinant polynucleotide may be designated as a recombinant target protein. A host cell comprising said recombinant polynucleotide and/or said recombinant target protein may be designated as a recombinant host cell.

The term "recombinant vectors", as used herein, includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, or plant) or in in vitro expression systems. Cloning vectors are generally used to engineer and amplify a certain desired DNA fragment and may lack functional sequences needed for expression of the desired DNA fragments.

In a preferred embodiment of the present invention, the polynucleotide encoding the target protein of interest is comprised in an expression vector and is operably linked to expression control sequences in order to regulate its expression in a host cell or is comprised in a cloning vector in order to allow its amplification in a host cell. The cloning vector or the expression vector comprising the polynucleotide encoding the target protein of interest is normally introduced in a host cell via transformation or transfection.

In a preferred embodiment of the present invention, the host cells are microbial host cells such as bacterial or yeast host cells, plant host cells or insect host cells.

In the context of the present invention, the term "microbial host cells", as used herein, refers to cells of microbial origin, for example, bacterial cells such as gram-negative or gram-positive bacterial cells, e.g. *Escherichia* (e.g. *Escherichia coli*), *Anabaena, Caulobacter, Gluconobacter, Rhodobacter, Pseudomonas, Para coccus, Bacillus* (e.g. *Bacillus subtilis*) *Brevibacterium, Corynebacterium, Rhizobium* (*Sinorhizobium*), *Flavobacterium, Klebsiella, Enterobacter, Lactobacillus, Lactococcus, Methylobacterium, Propionibacterium, Staphylococcus* or *Streptomyces* cells, or yeast cells such as ascosporogenous (Endomycetales) cells, basidiosporogenous cells, or cells belonging to the Fungi Imperfecti (Blastomycetes), e.g. *Candida, Hansenula, Kluyveromyces, Saccharomyces* (e.g. *Saccharomyces cerevisiae*), *Schizosaccharomyces, Pichia* (e.g. *Pichia pastoris*) or *Yarrowia* cells.

In the context of the present invention, the term "insect host cells" refers to cells of insect origin such as *Spodoptera frugiperda* or *Trichoplusia ni* cells. Preferably, the insect cells are SF9 cells, SF-21 cells or High-Five cells. SF-9 and SF-21 are ovarian cells from *Spodoptera frugiperda*. High-Five cells are egg cells from *Trichoplusia ni*.

In the context of the present invention, the term "plant host cells", as used herein, refers to cells of plant origin such as tobacco, potato or pea cells.

The term "a suspension of intact or disrupted host cells", as used herein, refers to a heterogeneous fluid containing intact or disrupted host cells. The fluid, wherein the intact or disrupted cells are suspended, may be a fermentation medium, a culture medium, an aqueous solution, e.g. a buffered aqueous solution, technical $H_2O$, or deionized $H_2O$. The buffered aqueous solution may be, for example, Tris/HCl. The pH of the buffered aqueous solution may be between pH 5.0 and pH 9.0, preferably between pH 6.0 and pH 8.0, and more preferably between pH 6.7 and pH 7.2, e.g. Tris/HCl, pH 7.0, pH 7.5 or pH 8.0. It is preferred that the buffered aqueous solution is a solution of between 10 and 100 mM Tris/HCl, more preferably of between 10 and 50 mM Tris/HCl, and most preferably of between 10 and 20 mM Tris/HCl, e.g. 10, 15, 20, 25, 30, 35, 40, 45, 50, 55, 60, 65, 70, 75, 80, 85, 90, 95, or 100 mM Tris/HCl, wherein said buffered aqueous solution has preferably a pH of between 5.0 and 9.0, more preferably a pH of between 6.0 and 8.0, and most preferably a pH of between 6.7 and 7.2, e.g. Tris/HCl, pH 7.0, pH 7.5 or pH 8.0. The culture medium may be a minimal medium, or a salt medium, (see, for example, Korz et al. Journal of Biotechnology 39, 1995, 59-65). The proportion of fluid to intact or disrupted host cells in the suspension may vary, e.g. between 5% and 95%. Thus, the term "suspension of intact or disrupted host cells" encompasses suspensions, wherein the proportion of fluid to intact or disrupted host cells may be 5 to 95%, 10 to 90%, 15 to 85%, 20 to 80%, 25% to 75%, 30 to 70%, 35 to 65%, 40 to 60%, 45 to 55%, 50 to 50%, 55 to 45%, 60 to 40%, 65 to 35%, 70 to 30%, 75 to 25%, 80 to 20%, 85 to 15%, 90 to 10%, or 95 to 5%.

In the context of the present invention, the term "a suspension of intact host cells" encompasses intact, generally non-lysed host cells, e.g. microbial host cells, plant host cells or insect host cells, suspended in a fluid, e.g. in an aqueous solution (e.g. a buffered aqueous solution), technical water, deionized water, culture medium or fermentation medium. The term "a suspension of disrupted host cells", as used herein, encompasses host cells, e.g. microbial host cells, plant host cells or insect host cells, that have disrupted cell walls or are lysed in a large part and which are suspended in a fluid, e.g. in an aqueous solution (e.g. a buffered aqueous solution), technical water, deionized water, culture medium or fermentation medium. The "suspension of disrupted host cells" may be prepared by (i) non-mechanical cell disruption (e.g. cell lysis with enzymes, cell treatment with chemical reagents in order to dissolve/partially dissolve or to open/partially open the cell walls and/or cell membranes, or cell breakage using osmotic pressure), (ii) mechanical cell disruption (e.g. mechanical grinding, or ball mill extraction), (iii) high-pressure homogenization, or (iv) sonification, and by combinations thereof.

In a preferred embodiment of the present invention, the intact host cells, e.g. microbial host cells such as bacterial host cells, which are provided in step a) are present in a suspension having a moisture content of between 5 and 20%, preferably of 5, 10, 15, or 20% (e.g. of 5, 6, 7, 8, 9, 10, 11, 12, 13, 14, 15, 16, 17, 18, 19, or 20%), i.e. in a cell sediment, preferably after separation of said cells from the culture medium, e.g. by centrifugation or filtration. In another preferred embodiment of the present invention, the disrupted host cells, e.g. microbial cells such as bacterial cells, are present in a suspension having a moisture content of between 5 and 20%, preferably of 5, 10, 15, or 20% (e.g. of 5, 6, 7, 8, 9, 10, 11, 12, 13, 14, 15, 16, 17, 18, 19, or 20%), i.e. in a cell sediment, preferably after separation of said disrupted, e.g. lysed or sonificated, cells from the culture medium, e.g. by centrifugation or filtration.

It should be noted that the amount of soluble host cell parts, e.g. organelles, soluble host cell proteins or soluble host cell remnants, and/or of other soluble ingredients, e.g. soluble fermentation-related impurities, soluble parts of the fermentation medium, or soluble parts of the culture medium, in the suspension of intact or disrupted host cells provided in step a) may vary. For example, the amount of soluble host cell parts and/or of other soluble ingredients is lower (i) in a cell sediment of intact or disrupted host cells having a moisture content of between 5 to 10%, produced by separating the intact or disrupted host cells from the culture medium or fermentation medium via centrifugation or filtration, or (ii) in an aqueous solution, wherein said cell sediment is resuspended, compared to the amount of soluble host cell parts and/or of other soluble ingredients (i) in a suspension of intact host cell in a culture medium or fermentation medium, or (ii) in a suspension of disrupted host cell in a culture medium or fermentation medium. It is also possible that no soluble host cell parts and/or other soluble ingredients are present in the suspension, e.g. aqueous solution, particularly in cases where a cell pellet of disrupted host cells is washed and resuspended in an aqueous solution which is subsequently provided in step a).

A "suspension of host cells", e.g. microbial, plant, or insect host cells, may be provided/produced by culturing host cells, e.g. microbial, plant or insect host cells, in a culture or fermentation. The production of target proteins may be performed in bioreactors in which the host cells, e.g. microbial, plant or insect host cells, may be cultivated efficiently. Three intersecting fermentation strategies may be applied: (i) continuous-fermentation, (ii) batch-fermentation or (iii) fed-batch-fermentation. These fermentation strategies may also be combined. In order to obtain the maximum yield, i.e. by providing a high biomass, of the desired target protein, it may be required to supply the host cells, e.g. microbial, plant or insect host cells, with sufficient nutrients and to combine this treatment with a continuous monitoring and adaption of relevant process parameters (e.g. dissolved oxygen, pH, and temperature). Target protein expression induction systems (e.g. Isopropyl-β-D-thiogalactopyranosid (IPTG) induction, induction with sugars or analogues thereof, temperature induction using temperature dependent promoters, induction using promoters controlled by osmotic stress, or induction commenced by metabolic changes within the cell) may be used. Many parameters can have an impact on target protein production and protein quality. To increase the yield of insoluble target protein in particular, a longer induction phase, altered incubation temperature, optimized nutrient supply and/or different types of cell stress can be applied. It may also be possible to influence the amount of target protein aggregate produced during the cell culture and purification process by carefully controlling the environment (e.g. media components, temperature during the fermentation process, duration of the fermentation process) and by implementing appropriate strategies to maximize the extent of aggregation.

A "suspension of host cells", e.g. microbial, plant, or insect host cells, may also be provided/produced by resuspending cultured host cells, e.g. microbial, plant or insect host cells, which have been separated from the culture medium, e.g. by centrifugation or filtration, in an aqueous solution, e.g. buffered aqueous solution, in technical water, or in deionized water. A suspension of plant cells may also be provided/produces by suspending plant cells which have been obtained from whole plants, e.g. by extracting said plant cells from said plants or by disrupting whole plants, in an aqueous solution, e.g. buffered solution, in technical water, or in deionized water.

In case that a suspension of intact host cells may be provided in step a) of the method of the present invention, one of the above described host cell suspensions can directly be used. In case that a suspension of disrupted host cells may be provided in step a) of the method of the present invention, the (intact) host cells comprised in one of the above described suspensions may be firstly disrupted, e.g. using non-mechanical cell disruption methods, or mechanical cell disruption methods (see above).

In the context of the present invention, the term "a suspension of disrupted host cells comprising an insoluble target protein and insoluble host cell parts" refers to a suspension, e.g. culture medium, buffered aqueous solution, technical water or deionized water, which directly comprises the insoluble target protein and the insoluble host cell parts (e.g. insoluble cell wall parts, or insoluble cell debris) from the disrupted host cells. In contrast thereto, the term "a suspension of intact host cells comprising an insoluble target protein and insoluble host cell parts", as used herein, refers to a suspension, e.g. culture medium, aqueous solution (e.g. buffered aqueous solution), technical water or deionized water, which comprises intact host cells, wherein the insoluble target protein and the insoluble host cell parts (e.g. insoluble cell wall, or insoluble host cell proteins) are comprised.

The term "insoluble host cell parts", as used herein, refers to insoluble host cell proteins, cell walls, cell membranes, cell wall parts, cell membrane parts, cytoskeleton parts, host cell debris, and/or insoluble cytoplasmic inclusions (e.g. crystals of calcium oxalate or silicon dioxide, granules of energy-storage materials such as starch, glycogen or polyhydroxy-butyrate), which are parts of the host cells, e.g. microbial, plant or insect host cells, or of the expression system used to express the target protein. This term does not encompass the insoluble target protein of the present invention. The term "insoluble host cell parts" further refers to host cell parts which are insoluble under the conditions that exist in step a) and which are solubilized under the conditions that exist in step b).

The term "soluble host cell parts", as used herein, refers to soluble host cell proteins, cell organelles, parts of cell organelles, and/or other soluble cell components, which are parts of the host cells, e.g. microbial, plant or insect host cells, or of the expression system used to express the target protein. The term "soluble host cell parts" further refers to host cell parts which are already soluble under the conditions that exist in step a) and which stay soluble under the conditions that exist in step b).

The term "target protein", as used in the context of the present invention, refers to the protein of interest, e.g. a silk protein such as a spider silk protein or insect silk protein, collagen, resilin, or keratin, which may be isolated from the suspension of host cells, e.g. microbial, plant, or insect host cells. In a preferred embodiment, said target protein is a recombinant target protein, more preferably a recombinant target protein encoded by a recombinant polynucleotide. In a further embodiment, the recombinant target protein is a hybrid protein of a spider silk protein and an insect silk protein, a spider silk protein and collagen, a spider silk protein and resilin or a spider silk protein and keratin. It is particularly preferred that said target protein is recombinantly produced in said host cells.

In a preferred embodiment, the target proteins are proteins comprising repeat units/domains that have the property to form target protein aggregates in a host cell, or in a suspension, e.g. in a culture medium, in an aqueous solution (e.g. a buffered aqueous solution), in technical water, or in deionized water.

In another preferred embodiment, the target proteins are present in form of target protein aggregates in a host cell, or in a suspension, e.g. in a cell culture medium, in an aqueous solution (e.g. buffered aqueous solution), in technical water, or in deionized water. Such target protein aggregates may be formed by the self-aggregation of target proteins in a host cell without the influence of the cellular scaffold or other intracellular mechanisms.

Particularly, the target protein aggregates may be formed by the self-aggregation of multiple copies/units of target proteins into a body or solid mass without the influence of the cellular scaffold or other intracellular mechanisms. The target protein aggregates may also be formed by self-aggregation of target proteins in a suspension, e.g. in a cell culture medium, in an aqueous solution (e.g. buffered aqueous solution), in technical water, or in deionized water. The target protein aggregates may be formed by several mechanisms which may include covalent or non-covalent interactions between the target protein molecules.

Preferably, the target protein aggregates comprise of at least 85%, more preferably of at least 90%, and most preferably of at least 95%, or of even 100%, e.g. at least 85, 86, 87, 88, 89, 90, 91, 92, 93, 94, 95, 96, 97, 98, 99%, or 100%, of the same target proteins, formed by aggregation of multiple copies of said target proteins. It was surprising that said target protein aggregates are not only a co-localization of target proteins within non-specific aggregates, but comprise of at least 85%, or of even 100% of the same target proteins showing a preference of the target proteins for self-aggregation.

The term "insoluble target protein" or the term "insoluble target protein aggregate", as used herein, refers to a target protein or to a target protein aggregate, which is not soluble in a suspension, e.g. cell culture medium, fermentation medium, aqueous solution (e.g. buffered aqueous solution such as Tris/HCl, pH 7.5), technical water, or deionized water, and which can, thus, be separated from the soluble host cell parts present in said suspension, e.g. by centrifugation and/or filtration. In addition, the term "insoluble target protein" or the term "insoluble target protein aggregate", as used herein, refers to a target protein or to a target protein aggregate, which is also not soluble in a suspension, e.g. cell culture medium, fermentation medium, aqueous solution (e.g. buffered aqueous solution such as Tris/HCl, pH 7.5), technical water, or deionized water, after addition of an aqueous solution comprising a base (e.g. 0.05 M NaOH) to said suspension, while other host cell parts that are insoluble in a suspension, e.g. cell culture medium, fermentation medium, aqueous solution (e.g. buffered aqueous solution such as Tris/HCl, pH 7.5), technical water, or deionized water, become soluble after addition of an aqueous solution comprising a base to said suspension and which can, thus, be further separated from the solubilized insoluble host cell parts present in said suspension, e.g. by centrifugation and/or filtration.

It is preferred that the insoluble target protein or insoluble target protein aggregate is insoluble in an buffered aqueous solution of between 10 and 100 mM Tris/HCl, more preferably of between 10 and 50 mM Tris/HCl, and most preferably of between 10 and 20 mM Tris/HCl, e.g. 10, 15, 20, 25, 30, 35, 40, 45, 50, 55, 60, 65, 70, 75, 80, 85, 90, 95, or 100 mM Tris/HCl, wherein said buffered aqueous solution has preferably a pH of between 5.0 and 9.0, more preferably a pH of between 6.0 and 8.0, and most preferably a pH of between 6.7 and 7.2, e.g. Tris/HCl, pH 7.0, pH 7.5 or pH 8.0.

If, for example, in step a) of the method of the present invention a suspension of intact host cells, e.g. microbial, plant, or insect host cells, is provided, an aqueous solution comprising at least one base is added in step b) in an amount which is sufficient/required to disrupt said host cells into insoluble host cell parts and to further solubilize said insoluble host cell parts to such an extend that at least 80%, preferably at least 90%, and more preferably at least 95%, or even 100%, e.g. at least 80, 81, 82, 83, 84, 85, 86, 87, 88, 89, 90, 91, 92, 93, 94, 95, 96, 97, 98, 99, 99.9%, or 100%, of said insoluble host cell parts are solubilized. Further, if, for example, in step a) of the method of the present invention a suspension of already disrupted host cells, e.g. microbial, plant, or insect host cells, is provided, i.e. a suspension comprising the insoluble host cell parts from the disrupted cells, an aqueous solution comprising at least one base is added in step b) in an amount which is sufficient/required to solubilize said insoluble host cell parts to such an extend that at least 80%, preferably at least 90%, and more preferably at least 95%, or even 100%, e.g. at least 80, 81, 82, 83, 84, 85, 86, 87, 88, 89, 90, 91, 92, 93, 94, 95, 96, 97, 98, 99, 99.9%, or 100%, of the insoluble host cell parts are solubilized.

The skilled person can easily access which amount of an aqueous solution comprising a base is sufficient/required to disrupt host cells, e.g. microbial, plant or insect host cells, and/or to solubilize insoluble host cell parts to such an extent that at least 80%, preferably at least 90%, and more preferably at least 95%, or even 100%, of said insoluble host cell parts are solubilized, for example, by (i) performing a dilution series of a selected base, e.g. NaOH, (ii) adding the selected base (e.g. NaOH) at several concentrations to a suspension of intact or disrupted host cells (e.g. NaOH in final concentrations of 0.01 M NaOH, 0.02 M NaOH, 0.03 M NaOH, 0.04 M NaOH, 0.05 M NaOH, 0.06 M NaOH, 0.07 M NaOH, 0.08 M NaOH, 0.09 M NaOH, 0.1 M NaOH, 0.2 M NaOH, 0.3 NaOH, 0.4 M NaOH, 0.5 M NaOH, 0.6 M NaOH, 0.7 M NaOH, 0.8 M NaOH, 0.9 M NaOH, or 1 M NaOH), (iii) separating the insoluble target protein from the completely or partially solubilized insoluble host cell parts, e.g. by centrifugation or filtration, (iv) evaluating the portion of insoluble host cell parts within the separated insoluble target protein portion, e.g. in the centrifugate or retentate, and (v) determining the amount of the base which is sufficient/required in order to solubilize at least 80%, preferably at least 90%, more preferably at least 95%, or even 100% of the insoluble host cell parts.

The term "the target protein remains insoluble", as used herein, refers to a target protein which is insoluble in a suspension, e.g. in an aqueous solution (e.g. buffered aqueous solution), in a culture medium, in a fermentation medium, in technical water, or in deionized water, and which stays insoluble, e.g. to at least 80%, preferably to at least 90%, and more preferably to at least 95%, or even to 100%, for example, to at least 80, 81, 82, 83, 84, 85, 86, 87, 88, 89, 90, 91, 92, 93, 94, 95, 96, 97, 98, 99, 99.9%, or 100%, in said suspension, e.g. in said aqueous solution (e.g. buffered aqueous solution), culture medium, fermentation medium, technical water, or deionized water, comprising a base, e.g. over a certain period of time and/or at a specific temperature, and, thus, allows the separation and isolation of said target protein, e.g. by filtration and/or centrifugation.

In a preferred embodiment of the present invention, the target protein is insoluble in a suspension, e.g. in an aqueous solution (e.g. buffered aqueous solution), in a culture medium, in a fermentation medium, in technical water, or in deionized water, and stays insoluble, e.g. to at least 80%, preferably to at least 90%, and more preferably to at least 95%, or even to 100%, for example, to at least 80, 81, 82, 83, 84, 85, 86, 87, 88, 89, 90, 91, 92, 93, 94, 95, 96, 97, 98, 99, 99.9%, or 100%, in said suspension, e.g. in said aqueous solution (e.g. buffered aqueous solution), culture medium, fermentation medium, technical water, or deionized water, comprising a base over a time period of at least 5 minutes, preferably of at least 10 minutes, more preferably of at least 90 minutes and most preferably of at least 180 minutes, e.g. over at least 5, 6, 7, 8, 9, 10, 15, 20, 25, 30, 35, 40, 45, 50, 55, 60, 65, 70, 75, 80, 85, 90, 100, 110, 120, 130, 140, 150, 160, 170, or 180 minutes.

In a further preferred embodiment of the present invention, the target protein is insoluble in a suspension, e.g. in an aqueous solution (e.g. buffered aqueous solution), in a culture medium, in a fermentation medium, in technical water, or in deionized water, and stays insoluble to at least 80%, preferably to at least 90%, and more preferably to at least 95%, or even to 100%, for example, to at least 80, 81, 82, 83, 84, 85, 86, 87, 88, 89, 90, 91, 92, 93, 94, 95, 96, 97, 98, 99, 99.9%, or 100%, in said suspension, e.g. in said aqueous solution (e.g. buffered aqueous solution), culture medium, fermentation medium, technical water, or deionized water, comprising a base over a time period of between 5 and 180 minutes, preferably of between 10 and 90 minutes, for example, over 5, 6, 7, 8, 9, 10, 15, 20, 25, 30, 35, 40, 45, 50, 55, 60, 65, 70, 75, 80, 85, 90, 100, 110, 120, 130, 140, 150, 160, 170, or 180 minutes, and/or at a temperature of between 4 and 60° C., for example, at 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, or 60° C.

In a more preferred embodiment of the present invention, the target protein is insoluble in a suspension, e.g. in an aqueous solution (e.g. buffered aqueous solution), in a culture medium, in a fermentation medium, in technical water or in deionized water, and stays insoluble to at least 90%, preferably to at least 95%, in said solution, e.g. in said aqueous solution, culture medium, fermentation medium, technical water, or deionized water, comprising a base over a time period of 10 minutes at a temperature of 15° C., 20° C., 25° C., 30° C., 35° C., or 40° C., over a period of 20 minutes at a temperature of 15° C., 20° C., 25° C., 30° C., 35° C., or 40° C., over a time period of 30 minutes at a temperature of 15° C., 20° C., 25° C., 30° C., 35° C., or 40° C., over a period of 40 minutes at a temperature of 15° C., 20° C., 25° C., 30° C., 35° C., or 40° C. in an aqueous solution, over a period of 50 minutes at a temperature of 15° C., 20° C., 25° C., 30° C., 35° C., or 40° C., over a period of 60 minutes at a temperature of 15° C., 20° C., 25° C., 30° C., 35° C., or 40° C., or over a period of 90 minutes at a temperature of 15° C., 20° C., 25° C., 30° C., 35° C., or 40° C.

In a most preferred embodiment of the present invention, the target protein is insoluble in a suspension, e.g. in an aqueous solution (e.g. buffered aqueous solution), in a culture medium, in a fermentation medium, in technical water, or in deionized water, and stays insoluble to at least 80%, preferably to at least 90%, and more preferably to at least 95%, or even to 100%, for example, to at least 80, 81, 82, 83, 84, 85, 86, 87, 88, 89, 90, 91, 92, 93, 94, 95, 96, 97, 98, 99, 99.9%, or 100%, in said suspension, e.g. in said aqueous solution (e.g. buffered aqueous solution), culture medium, fermentation medium, technical water, or deionized water, comprising a base, for example, a metal hydroxide and/or ammonia such as sodium hydroxide (NaOH), potassium hydroxide (KOH) and/or calcium hydroxide (CaOH), which final concentration ranges from 0.005 M to 1 M, preferably from 0.01 M to 0.6 M, more preferably from 0.02 M to 0.2 M, 0.05 M to 0.15 M or 0.04 M to 0.1 M, and most preferably from 0.04 M to 0.06 M, over a time period of between 5 and 180 minutes, preferably of between 10 and 90 minutes, for example, over 5, 6, 7, 8, 9, 10, 15, 20, 25, 30, 35, 40, 45, 50, 55, 60, 65, 70, 75, 80, 85, 90, 100, 110, 120, 130, 140, 150, 160, 170, or 180 minutes, and/or at a temperature of between 4 and 60° C., for example, at 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, or 60° C.

It is particularly preferred that the target protein remains insoluble to at least 90%, preferably to at least 95%, or even to 100%, e.g. to at least 90, 91, 92, 93, 94, 95, 96, 97, 98, 99, 99.9%, or 100%, after the addition of an aqueous solution comprising at least one base in step b) over a time period of between 10 and 40 min and at a temperature of between 15° C. and 25° C. It is particularly more preferred that the target protein remains insoluble to at least 90%, preferably to at least 95%, or even to 100%, e.g. to at least 90, 91, 92, 93, 94, 95, 96, 97, 98, 99, 99.9%, or 100%, after the addition of an aqueous solution comprising at least one base in step b) over a time period of between 20 and 30 min and at a temperature of between 20° C. and 25° C.

In a further preferred embodiment of the present invention, the target proteins, e.g. spider silk proteins, which remain insoluble, are separated/isolated from the solubilized insoluble host cell parts using a filter, e.g. a filter having a pore size of 0.1 µM or 0.22 µM and/or by centrifugation, e.g. at 3000 to 8000×g for 20 to 30 minutes.

In another preferred embodiment, the target proteins remain insoluble in form of target protein aggregates (e.g. silk protein aggregates such as spider silk protein aggregates).

Thus, the term "the target protein aggregate remains insoluble" refers to a target protein aggregate formation which is not reversible or which is not reversible to more than 0.1, 1, 2, 3, 4, 5, 6, 7, 8, 9, 10, 11, 12, 13, 14, 15, 16, 17, 18, 19 or 20% in a suspension, e.g. in an aqueous solution (e.g. buffered aqueous solution), in a culture medium, in a fermentation medium, in technical water, or in deionized water, comprising a base, e.g. over a certain period of time and/or at a specific temperature, and, thus, allows the separation and isolation of said target protein aggregates, e.g. by filtration and/or centrifugation.

The term "target protein aggregate remains insoluble" also refers to a target protein aggregate which stays insoluble, e.g. to at least 80%, preferably to at least 90%, and more preferably to at least 95%, or even to 100%, for example, to at least 80, 81, 82, 83, 84, 85, 86, 87, 88, 89, 90, 91, 92, 93, 94, 95, 96, 97, 98, 99, 99.9%, or 100%, in a suspension, e.g. in an aqueous solution (e.g. buffered aqueous solution), in a culture medium, in a fermentation medium, in technical water, or deionized water, comprising a base, e.g. over a certain period of time and/or at a specific temperature, and, thus, allows the separation and isolation of said target protein aggregates, e.g. by filtration and/or centrifugation.

In a more preferred embodiment of the present invention, the target protein aggregate formation is not reversible or is not reversible to more than 0.1, 1, 2, 3, 4, 5, 6, 7, 8, 9, 10, 11, 12, 13, 14, 15, 16, 17, 18, 19, or 20% in a suspension, e.g. in an aqueous solution (e.g. buffered aqueous solution), in a culture medium, in a fermentation medium, in technical water or in deionized water, comprising a base; e.g. a metal hydroxide and/or ammonia, over a time period of between 5 and 180 minutes, preferably of between 10 and 90 minutes, for example, over 5, 6, 7, 8, 9, 10, 15, 20, 25, 30, 35, 40, 45, 50, 55, 60, 65, 70, 75, 80, 85, 90, 100, 110, 120, 130, 140, 150, 160, 170, or 180 minutes, and/or at a temperature of between 4 and 60° C., for example, at 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, or 60° C.

In a another embodiment of the present invention, the target protein aggregate stays insoluble to at least 80%, preferably to at least 90%, and more preferably to at least 95%, or even to 100%, for example, to at least 80, 81, 82, 83, 84, 85, 86, 87, 88, 89, 90, 91, 92, 93, 94, 95, 96, 97, 98, 99, 99.9%, or 100%, in a suspension, e.g. in an aqueous solution (e.g. buffered aqueous solution), in a culture medium, in a fermentation medium, in technical water, or in deionized water, comprising a base, e.g. a metal hydroxide and/or ammonia, over a time period of between 5 and 180 minutes, preferably of between 10 and 90 minutes, for example, over 5, 6, 7, 8, 9, 10, 15, 20, 25, 30, 35, 40, 45, 50, 55, 60, 65, 70, 75, 80, 85, 90, 100, 110, 120, 130, 140, 150, 160, 170, or 180 minutes, and/or at a temperature of between 4 and 60° C., for example, at 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, or 60° C.

In a particular preferred embodiment of the present invention, the target protein aggregate formation is not reversible to more than 10% in a suspension, e.g. in an aqueous solution (e.g. buffered aqueous solution), in a culture medium, in a fermentation medium, in technical water or deionized water, comprising a base, e.g. a metal hydroxide and/or ammonia, over a time period of 10 minutes at a temperature of 15° C., 20° C., 25° C., 30° C., 35° C., or 40° C., over a period of 20 minutes at a temperature of 15° C., 20° C., 25° C., 30° C., 35° C., or 40° C., over a time period of 30 minutes at a temperature of 15° C., 20° C., 25° C., 30° C., 35° C., or 40° C., over a period of 40 minutes at a temperature of 15° C., 20° C., 25° C., 30° C., 35° C., or 40° C. in an aqueous solution, over a period of 50 minutes at a temperature of 15° C., 20° C., 25° C., 30° C., 35° C., or 40° C., over a period of 60 minutes at a temperature of 15° C., 20° C., 25° C., 30° C., 35° C., or 40° C., or over a period of 90 minutes at a temperature of 15° C., 20° C., 25° C., 30° C., 35° C., or 40° C.

In a another embodiment of the present invention, the target protein aggregate stays insoluble to at least 80%, preferably to at least 90%, and more preferably to at least 95%, or even to 100%, for example, to at least 80, 81, 82, 83, 84, 85, 86, 87, 88, 89, 90, 91, 92, 93, 94, 95, 96, 97, 98, 99, 99.9%, or 100%, in a suspension, e.g. in an aqueous solution (e.g. buffered aqueous solution), in a culture medium, in a fermentation medium, in technical water, or in deionized water, comprising a base, for example, a metal hydroxide and/or ammonia such as sodium hydroxide (NaOH), potassium hydroxide (KOH) and/or calcium hydroxide (CaOH), which final concentration ranges from 0.005 M to 1 M, preferably from 0.01 M to 0.6 M, more preferably from 0.02 M to 0.2 M, 0.05 M to 0.15 M or 0.04 M to 0.1 M, and most preferably from 0.04 M to 0.06 M, over a time period of between 5 and 180 minutes, preferably of between 10 and 90 minutes, for example, over 5, 6, 7, 8, 9, 10, 15, 20, 25, 30, 35, 40, 45, 50, 55, 60, 65, 70, 75, 80, 85, 90, 100, 110, 120, 130, 140, 150, 160, 170, or 180 minutes, and/or at a temperature of between 4 and 60° C., for example, at 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, or 60° C.

In a more preferred embodiment, the target protein is a target protein with repeat domains/repetitive units (e.g. a silk protein such as a spider silk protein) and has the property to form protein aggregates. Once the protein aggregates are formed, said protein aggregates are preferably insoluble in a suspension, e.g. in an aqueous solution (e.g. buffered aqueous solution), in a culture medium, in a fermentation medium, in technical water, or in deionized water, and stay insoluble to at least 80%, preferably to at least 90%, and more preferably to at least 95%, or even to 100%, for example, to at least 80, 81, 82, 83, 84, 85, 86, 87, 88, 89, 90, 91, 92, 93, 94, 95, 96, 97, 98, 99, 99.9%, or 100%, in said suspension, e.g. in said aqueous solution (e.g. buffered aqueous solution), culture medium, fermentation medium, technical water, or deionized water, comprising a base, e.g. a metal hydroxide and/or ammonia, over a time period of between 5 and 180 minutes, preferably of between 10 and 90 minutes, for example, over 5, 6, 7, 8, 9, 10, 15, 20, 25, 30, 35, 40, 45, 50, 55, 60, 65, 70, 75, 80, 85, 90, 100, 110, 120, 130, 140, 150, 160, 170, or 180 minutes, and/or at a temperature of between 4 and 60° C., for example, at 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, or 60° C.

The target protein aggregates, e.g. spider silk protein aggregates, which remain insoluble are either visible as discrete particles by using, for example, the unaided eye, an light microscope, or an electron microscope, and/or can be removed/separated from the solubilized insoluble host cell parts by a filter, e.g. a filter having a pore size of 0.1 μM or 0.22 μM.

Preferably, the insoluble target protein forms a protein aggregate, which comprises of at least 85%, more preferably of at least 90%, and most preferably of at least 98%, or even of 100%, e.g. at least 85, 86, 87, 88, 89, 90, 91, 92, 93, 94, 95, 96, 97, 98, 99, 99.9%, or 100%, of said target protein. The term "target protein aggregate that comprises of at least 85%, more preferably of at least 90%, and most preferably of at least 98%, or even of 100% of the same target protein", as used in the context of the present invention, means that the target protein aggregate is formed by aggregation of multiple copies/units of the same target protein and that this aggregate comprises of at least 85%, more preferably of at least 90%, and most preferably of at least 98%, or even of 100% of said target protein.

It is preferred that step b) of the method of the present invention is carried out over a time period during which the target protein remains insoluble.

It is more preferred that step b) of the method of the present invention is carried out over a time period of between 5 and 180 min, preferably of between 10 and 90 min, and most preferably of between 10 and 40 min, e.g. over 5, 6, 7, 8, 9, 10, 15, 20, 25, 30, 35, 40, 45, 50, 55, 60, 65, 70, 75, 80, 85, 90, 100, 110, 120, 130, 140, 150, 160, 170, or 180 minutes. For example, step b) of the method of the present invention is carried out over a time period of between 30 and 180 min in order to solubilize insoluble host cell parts from a culture medium of intact bacterial host cells, e.g. at a temperature of between 20° C. and 25° C.

Preferably, the insoluble target protein or insoluble target protein aggregate isolated/separated with the method of the present invention has a purity of at least 50% or 60%, more preferably of at least 70% or 80%, and most preferably of at least 90%, 95%, or even of 100%, e.g. of at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.9%, or 100%.

A purity of at least 50% or 60%, more preferably of at least 70% or 80%, and most preferably of at least 90%, 95%, or even of 100%, e.g. of at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.9%, or 100%, of the isolated insoluble target protein or target protein aggregate preferably means that it is to at least 50% or 60%, more preferably to at least 70% or 80%, and most preferably to at least 90%, 95%, or even to 100%, e.g. to at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.9%, or 100%, free of (i) insoluble host cell parts (e.g. insoluble host cell proteins, cell wall parts, cell membrane parts, cytoskeleton parts, host cell debris, and/or cytoplasmic inclusions) and/or soluble host cell parts (e.g. soluble host cell proteins, parts of cell organelles and/or cell components), and more preferably free of (i) insoluble host cell parts (e.g. insoluble host cell proteins, cell wall parts, cell membrane parts, cytoskeleton parts, host cell debris, and/or cytoplasmic inclusions) and/or soluble host cell parts (e.g. soluble host cell proteins, parts of cell organelles and/or cell components) and (ii) soluble and/or insoluble suspension remnants (e.g. fermentation/cultivation-related impurities such as minerals and/or trace elements).

Further, a purity of at least 50% or 60%, more preferably of at least 70% or 80%, and most preferably of at least 90%, 95%, or even of 100%, e.g. of at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.9%, or 100%, of the isolated insoluble target protein or target protein aggregate more preferably means that it is to at least 50% or 60%, more preferably to at least 70% or 80%, and most preferably to at least 90%, 95%, or even to 100%, e.g. to at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.9%, or 100%, free of (i) insoluble and/or soluble host cell proteins, most preferably free of (i) insoluble and/or soluble host cell proteins and (ii) insoluble cell wall parts, cell membrane parts, cytoskeleton parts, host cell debris, cytoplasmic inclusions, soluble parts of cell organelles and/or soluble cell components, and even most preferably free of (i) insoluble and/or soluble host cell proteins, (ii) insoluble cell wall parts, cell membrane parts, cytoskeleton parts, host cell debris, cytoplasmic inclusions, soluble parts of cell organelles and/or soluble cell components, and (iii) soluble and/or insoluble suspension remnants (e.g. fermentation/cultivation-related impurities such as minerals and/or trace elements).

Alternatively, a purity of at least 50% or 60%, more preferably of at least 70% or 80%, and most preferably of at least 90%, 95%, or even of 100%, e.g. of at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.9%, or 100%, of the isolated insoluble target protein or target protein aggregate preferably means that it comprises no more than 50% or 40%, more preferably no more than 30% or 20%, and most preferably no more than 10%, 5%, or 0%, e.g. 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1% or 0%, (i) insoluble host cell parts (e.g. insoluble host cell proteins, cell wall parts, cell membrane parts, cytoskeleton parts, host cell debris, and/or cytoplasmic inclusions) and/or soluble host cell parts (e.g. soluble host cell proteins, parts of cell organelles and/or cell components), and more preferably (i) insoluble host cell parts (e.g. insoluble host cell proteins, cell wall parts, cell membrane parts, cytoskeleton parts, host cell debris, and/or cytoplasmic inclusions) and/or soluble host cell parts (e.g. soluble host cell proteins, parts of cell organelles and/or cell components) and (ii) soluble and/or insoluble suspension remnants (e.g. fermentation/cultivation-related impurities such as minerals and/or trace elements).

Further, a purity of at least 50% or 60%, more preferably of at least 70% or 80%, and most preferably of at least 90%, 95%, or even of 100%, e.g. of at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.9%, or 100%, of the isolated insoluble target protein or target protein aggregate more preferably means that it comprises no more than 50% or 40%, more preferably no more than 30% or 20%, and most preferably no more than 10%, 5%, or 0%, e.g. 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1% or 0%, (i) insoluble and/or soluble host cell proteins, most preferably (i) insoluble and/or soluble host cell proteins and (ii) insoluble cell wall parts, cell membrane parts, cytoskeleton parts, host cell debris, cytoplasmic inclusions, soluble parts of cell organelles and/or soluble cell components, and even most preferably (i) insoluble and/or soluble host cell proteins, (ii) insoluble cell wall parts, cell membrane parts, cytoskeleton parts, host cell debris, cytoplasmic inclusions, soluble parts of cell organelles and/or soluble cell components, and (iii) soluble and/or insoluble suspension remnants (e.g. fermentation/cultivation-related impurities such as minerals and/or trace elements).

The skilled person is aware of techniques how to determine the purity of the insoluble target protein or target protein aggregate isolated with the method of the present invention.

The purity of the isolated insoluble target protein or target protein aggregate is preferably measured using (i) spectrometry, preferably mass spectrometry (MS), (ii) chromatography, preferably liquid chromatography (LC), more preferably high performance liquid chromatography (HPLC), (iii) gel electrophoresis, preferably SDS gel electrophoresis, (iv) Westernblot/Immunoblot, or (v) combinations thereof.

It is preferred that the chromatography, preferably liquid chromatography (LC), more preferably high performance liquid chromatography (HPLC), is combined with spectrometry, preferably mass spectrometry (MS). Accordingly, the purity of the isolated insoluble target protein or target protein aggregate is preferably measured using liquid chromatography-mass spectrometry (LC-MS) and is more preferably measured using high performance liquid chromatography-mass spectrometry (HPLC-MS).

Preferably, the purity of the insoluble target protein or target protein aggregate isolated with the method of the present invention is calculated on a dry weight basis, e.g. expressed as % on a dry weight (wt/wt) basis.

It is particularly preferred that the dry weight of the isolated insoluble target protein or target protein aggregate is calculated in relation to the dry weight of the (i) insoluble and/or soluble host cell parts, more preferably (i) insoluble and/or soluble host cell parts and (ii) soluble and/or insoluble suspension remnants (see above).

It is further particularly preferred that the dry weight of the isolated insoluble target protein or target protein aggregate is calculated in relation to the dry weight of the (i) insoluble and/or soluble host cell proteins, more preferably (i) insoluble and/or soluble host cell proteins and (ii) insoluble cell wall parts, cell membrane parts, cytoskeleton parts, host cell debris, cytoplasmic inclusions, soluble parts of cell organelles and/or soluble cell components, and most preferably (i) insoluble and/or soluble host cell proteins, (ii) insoluble cell wall parts, cell membrane parts, cytoskeleton parts, host cell debris, cytoplasmic inclusions, soluble parts of cell organelles and/or soluble cell components, and (iii) soluble and/or insoluble suspension remnants (e.g. fermentation/cultivation-related impurities such as minerals and/or trace elements).

It is preferred that the aqueous solution comprising a base in step b) has a pH of between 7 and 14, more preferably of between 9 and 13, and most preferably of between 10 and 12. For example, the aqueous solution comprising a base in step b) has a pH of 7, 7.5, 8, 8.5, 9, 9.5, 10, 10.5, 11, 11.5, 12, 12.5, 13, 13.5, or 14.

In a preferred embodiment of the present invention, the base is a metal hydroxide or ammonia. In another preferred embodiment of the present invention a metal hydroxide and ammonia are used. Preferably, the metal hydroxide is selected from the group consisting of sodium hydroxide (NaOH), potassium hydroxide (KOH), and calcium hydroxide (CaOH), or is a combination thereof. Most preferably, the base is sodium hydroxide (NaOH).

Preferably, the final concentration of the base in step b) ranges from 0.005 M to 1 M, preferably from 0.01 M to 0.6 M, more preferably from 0.02 M to 0.2 M, 0.05 M to 0.15 M, or 0.04 M to 0.1 M, and most preferably from 0.04 M to 0.06 M. For example the final concentration of the base in step b) of the method of the present invention is 0.005 M, 0.01 M, 0.015 M, 0.02 M, 0.025 M, 0.03 M, 0.035 M, 0.04 M, 0.045 M, 0.05 M, 0.055 M, 0.06 M, 0.065 M, 0.07 M, 0.075 M, 0.08 M, 0.085 M, 0.09 M, 0.095 M, 0.1 M, 0.15 M, 0.2 M, 0.25 M, 0.3 M, 0.35 M, 0.4 M, 0.45 M, 0.5 M, 0.55 M, 0.6 M, 0.65 M, 0.7 M, 0.75 M, 0.8 M, 0.85 M, 0.9 M, 0.95 M, or 1 M.

In preferred embodiments of the method of the present invention, the final concentration of sodium hydroxide (NaOH), potassium hydroxide (KOH) and/or calcium hydroxide (CaOH) in step b) ranges from 0.005 M to 1 M, preferably from 0.01 M to 0.6 M, more preferably from 0.02 M to 0.2 M, 0.05 M to 0.15 M, or 0.04 M to 0.1 M, and most preferably from 0.04 M to 0.06 M. For example the final concentration of sodium hydroxide (NaOH), potassium hydroxide (KOH), and/or calcium hydroxide (CaOH) in step b) of preferred embodiments of the method of the present invention is 0.005 M, 0.01 M, 0.015 M, 0.02 M, 0.025 M, 0.03 M, 0.035 M, 0.04 M, 0.045 M, 0.05 M, 0.055 M, 0.06 M, 0.065 M, 0.07 M, 0.075 M, 0.08 M, 0.085 M, 0.09 M, 0.095 M, 0.1 M, 0.15 M, 0.2 M, 0.25 M, 0.3 M, 0.35 M, 0.4 M, 0.45 M, 0.5 M, 0.55 M, 0.6 M, 0.65 M, 0.7 M, 0.75 M, 0.8 M, 0.85 M, 0.9 M, 0.95 M, or 1 M.

In more preferred embodiments of the method of the present invention, the base in step b) is sodium hydroxide (NaOH) and the final concentration of sodium hydroxide (NaOH) in step b) ranges from 0.005 M to 1 M, preferably from 0.01 M to 0.6 M, more preferably from 0.02 M to 0.2 M, 0.05 M to 0.15 M, or 0.04 M to 0.1 M, and most preferably from 0.04 M to 0.06 M. For example the final concentration of sodium hydroxide (NaOH) in step b) of preferred embodiments of the method of the present invention is 0.005 M, 0.01 M, 0.015 M, 0.02 M, 0.025 M, 0.03 M, 0.035 M, 0.04 M, 0.045 M, 0.05 M, 0.055 M, 0.06 M, 0.065 M, 0.07 M, 0.075 M, 0.08 M, 0.085 M, 0.09 M, 0.095 M, 0.1 M, 0.15 M, 0.2 M, 0.25 M, 0.3 M, 0.35 M, 0.4 M, 0.45 M, 0.5 M, 0.55 M, 0.6 M, 0.65 M, 0.7 M, 0.75 M, 0.8 M, 0.85 M, 0.9 M, 0.95 M, or 1 M.

Preferably, the proportion of a suspension of intact or disrupted host cells, e.g. a cell culture medium, a fermentation medium, an aqueous solution (e.g. buffered aqueous solution), or a suspension having a moisture content of between 5 to 20%, e.g. 5, 6, 7, 8, 9, 10, 11, 12, 13, 14, 15, 16, 17, 18, 19, or 20%, i.e. a cell sediment, to a aqueous solution comprising a base ranges between 3:1 and 1:20, more preferably between 1:1 and 1:10, and most preferably between 1:2 and 1:4, e.g. 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20.

It is particularly preferred that step b) of the present invention is carried out with an aqueous solution comprising sodium hydroxide (NaOH) as a base at a final concentration of between 0.05 M to 0.15 M, preferably at a final concentration of 0.05 M, over a time period of between 10 and 30 min, preferably over a time period of between 20 and 30 min and at a temperature of between 20 and 25° C., preferably at a temperature of 20° C.

It is preferred that, in order to improve the yield, purity and/or the further processability of the isolated insoluble target protein, the method further comprises the addition of at least one reagent (i) prior to step b), (ii) in step b) and/or (iii) subsequent to step b), e.g. prior to step b), in step b), subsequent to step b), prior to step b) and in step b), prior to step b) and subsequent to step b), in step b) and subsequent to step b), or prior to step b), in step b) and subsequent to step b).

Preferably, the reagent is selected from the group consisting of a denaturing agent, a kosmotropic agent, and a detergent, or is a combination thereof.

Accordingly, in a preferred embodiment of the present invention, a denaturing agent, a kosmotropic agent, and/or a detergent is added (i) prior to step b), (ii) in step b) and/or (iii) subsequent to step b).

The denaturing agent enhances the solubilization of the insoluble host cell parts, whereas the detergent helps to solubilize the cell walls and/or cell membranes of the host cells, e.g. microbial host cells, plant host cells or insect host cells. In addition, the kosmotropic agent helps to stabilize the target protein aggregates.

Thus, it is preferred to add to a suspension of intact host cells, e.g. bacterial or plant host cell, prior to step b), in step b) and/or subsequent to step b) a detergent which helps to solubilize the cell walls and/or cell membranes, preferably in combination with a denaturizing agent which further enhances the solubilization of the remaining insoluble host cell parts. Therefore, is also preferred to add to a suspension of already disrupted host cells, e.g. bacterial or plant host cell, prior to step b), in step b) and/or subsequent to step b) a denaturizing agent which enhances the solubilization of the remaining insoluble host cell parts, preferably in combination with an kosmotropic agent which stabilizes the insoluble target protein aggregates.

The inventors of the present invention have surprisingly found that the addition of a denaturing agent, a kosmotropic agent, and/or detergent prior to step b), in step b) and/or subsequent to step b) can enhance the purity of the isolated insoluble target protein about up to 5 to 20%, e.g. up to 5, 6, 7, 8, 9, 10, 11, 12, 13, 14, 15, 16, 17, 18, 19 or 20% and/or the yield of the isolated insoluble target protein about up to 5 to 20%, e.g. up to 5, 6, 7, 8, 9, 10, 11, 12, 13, 14, 15, 16, 17, 18, 19, or 20%. For example, an isolated insoluble target protein having after the separation step c) a purity of 80, 81, 82, 83, 84, 85, 86, 87, 88, 89, 90, 91, 92, 93, 94, or 95% without the addition of a denaturing agent, a kosmotropic agent and/or a detergent prior to step b), in step b) and/or subsequent to step b), may have a purity of 85, 86, 87, 88, 89, 90, 91, 92, 93, 94, 95, 96, 97, 98, 99, or 100% after the addition of a denaturing agent, a kosmotropic agent, and/or detergent prior to step b), in step b) and/or subsequent to step b).

Preferably, (i) the denaturing agent is urea ($CH_4N_2O$) or guanidinium hydrochloride ($CH_5N_3HCl$), (ii) the kosmotropic agent is a phosphate salt or a sulfate salt, or (iii) the detergent is Tween20, Tween 60, Tween 80, TritonX-15, Triton X-45, Triton X-100, Triton X-102, Triton X-114, Triton X-151, TritonX-165, Triton X-200, Triton X-207, Triton X-301, Triton X-305, Triton X-405, Triton X-705, SDS, or Brij. The person skilled in the art is able to select further suitable denaturing agents, kosmotropic agents or detergents.

Preferably, the phosphate salt is ammonium phosphate, potassium phosphate, or sodium phosphate. The phosphate salt may reduce the solubility of the target protein or target protein aggregates in a suspension of intact or disrupted host cells, e.g. in an aqueous solution, fermentation medium, culture medium, technical water or deionized water. Preferably, the sulfate salt is ammonium sulfate.

It is preferred that the final concentration of urea ranges from 0.1 M to 10 M, preferably from 1 M to 5 M, and more preferably from 4 to 5 M. For example, the final concentration of urea is 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 M. It is also preferred that the final concentration of guanidinium hydrochloride ranges from 0.01 M to 3 M, preferably from 0.1 M to 2 M. For example, the final concentration of guanidinium hydrochloride is 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3 M.

In a preferred embodiment of the present invention, the target protein or target protein aggregate remains insoluble to at least 85%, preferably to at least 90%, and more preferably to at least 95%, or even to 100% in an aqueous solution comprising sodium hydroxide (NaOH) (e.g. at a final concentration which ranges from 0.005 M to 0.5 M) and guanidinium hydrochloride ($CH_5N_3HCl$) (e.g. at a final concentration which ranges from 0.01 M to 3 M) or urea (e.g. at a final concentration of urea which ranges from 0.1 M to 10 M), over a time period of between 20 to 40 min and at a temperature of between 20° C. and 25° C.

In another preferred embodiment of the present invention, the target protein, e.g. the spider silk protein such as the spider silk protein $C_{16}$, or target protein aggregate remains insoluble to at least 85%, preferably to at least 90%, and more preferably to at least 95%, or even to 100% in aqueous medium including sodium hydroxide (NaOH) (e.g. at a final concentration which ranges from 0.005 M to 0.2 M) and guanidinium hydrochloride ($CH_5N_3HCl$) (e.g. at a final concentration which ranges from 0.1 M to 2 M) or urea (e.g. at a final concentration which ranges from 1 M to 5 M), over a time period of between 20 and 40 min and at a temperature of between 20° C. and 25° C.

In a further preferred embodiment of the present invention, the target protein, e.g. the spider silk protein such as the spider silk protein $C_{16}$, or the target protein aggregate remains insoluble to at least 85%, preferably to at least 90%, and more preferably to at least 95%, or even to 100% in an aqueous medium comprising sodium hydroxide (NaOH) at a final concentration of 0.5 M over a time period of 30 min and at a temperature of between 20 and 25° C.

It is preferred that the separation of the insoluble target protein or the insoluble target protein aggregate from the solubilized insoluble host cell parts in step c) is achieved by centrifugation. The centrifugation step allows the separation of the solid phase comprising the insoluble target protein or insoluble target protein aggregate from the liquid phase, e.g. aqueous solution (e.g. aqueous buffered solution), culture medium, fermentation medium, technical water or deionized water, which comprises the solubilized insoluble host cell parts (e.g. host cell proteins, host cell debris) and optionally the solubilized insoluble remnants (e.g. fermentation remnants), soluble host cell parts and/or other soluble impurities. After the centrifugation step, the insoluble target protein or the insoluble target protein aggregate is present as precipitate, while the supernatant contains the solubilized insoluble host cell parts and optionally the solubilized insoluble remnants (e.g. fermentation remnants), soluble host cell parts and/or other soluble impurities and can be discarded. Thus, it should be clear to the skilled person that during this separation step, the insoluble target protein is separated from the solubilized insoluble host cell parts and optionally from the soluble host cell parts which are present or which are still present in the liquid phase, e.g. aqueous solution or culture medium.

It is also preferred that the separation of the insoluble target protein or the insoluble target protein aggregate from the solubilized insoluble host cell parts in step c) is achieved by filtration. In this separation method, the insoluble target protein is concentrated by passing the liquid phase, e.g. aqueous solution (e.g. aqueous buffered solution), culture medium, fermentation medium, technical water or deionized water, which comprises the insoluble target protein, the solubilized insoluble host cell parts and optionally solubilized insoluble remnants (e.g. fermentation remnants), soluble host cell parts and/or other soluble impurities through a filter membrane which retains the insoluble target protein and which lets pass the solubilized insoluble host cell parts and optionally the solubilized insoluble remnants (e.g. fermentation remnants), soluble host cell parts and/or other soluble impurities. Thus, it should be clear to the skilled person that during this separation step, the insoluble target protein is separated from the solubilized insoluble host cell parts and optionally from the soluble host cell parts which are present or which are still present in the liquid phase, e.g. aqueous solution or culture medium, that is passed through the filter membrane. In preferred embodiments of the method of the present invention, the movement of the liquid phase, e.g. aqueous solution (e.g. buffered aqueous solution), the culture medium, the fermentation medium, the technical water or deionized water, comprising the insoluble target protein and the solubilized insoluble host cell parts is accelerated by gravitational force pressure, vacuum, and/or centrifugation.

It is further preferred that the separation of the insoluble target protein from the solubilized insoluble host cell parts in step c) is achieved by sedimentation. In this separation method, the insoluble target protein or insoluble target protein aggregate is settled out of the fluid phase, e.g. the aqueous solution (e.g. buffered aqueous solution), the culture medium, the fermentation medium, the technical water or deionized water, in which it is comprised and come to rest against a wall. This is due to the motion of the insoluble target protein or insoluble target protein aggregate through the fluid in response to the forces acting on it, e.g. gravity. The solubilized insoluble host cell parts and optionally the solubilized insoluble remnants (e.g. fermentation remnants), soluble host cell parts and/or other soluble impurities retain in solution, form the supernatant and can, thus, simply be discarded.

It is particularly preferred that the separation of the insoluble target protein from the solubilized insoluble host cell parts in step c) is achieved by a combination of centrifugation, sedimentation and/or filtration, e.g. centrifugation and filtration, sedimentation and filtration, sedimentation and centrifugation, or centrifugation, sedimentation and filtration.

Depending on different insoluble target proteins, the parameter for centrifugation, sedimentation or filtration may vary. The person skilled in the art is able to easily adapt the appropriate separation parameters, e.g. the acceleration-force/G-force and/or time using centrifugation for separation, filter size using filtration for separation, and/or sedimentation time using sedimentation for separation, in order to separate/isolate the solubilized insoluble host cell parts from the insoluble target protein.

Preferably, the centrifugation is performed at such an acceleration-force/G-force and/or over such a centrifugation time which is sufficient to allow the sedimentation of at least 80%, more preferably of at least 90%, and most preferably of at least 95%, or even of 100%, e.g. of at least 80, 81, 82, 83, 84, 85, 86, 87, 88, 89, 90, 91, 92, 93, 94, 95, 96, 97, 98, 99, 99.9%, or 100%, of the insoluble target protein or the insoluble target protein aggregate, while the solubilized insoluble host cell parts or most of the solubilized insoluble host cell parts remain in solution. In a preferred embodiment of the method of the present invention, the centrifugation takes place between 3000×g and 12000×g, e.g. at 3000, 3500, 4000, 4500, 5000, 5500, 6000, 6500, 7000, 7500, 8000, 8500, 9000, 9500, 10000, 10500, 11000, 11500, or 12000×g, and/or for 10 to 40 min, e.g. for 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 min. These centrifugation parameters allow the sedimentation of at least 80%, preferably of at least 90%, and more preferably of at least 95%, or even of 100%, e.g. of at least 80, 81, 82, 83, 84, 85, 86, 87, 88, 89, 90, 91, 92, 93, 94, 95, 96, 97, 98, 99, 99.9%, or 100%, of the insoluble target protein or the insoluble target protein aggregate, while the solubilized insoluble host cell parts or most of the solubilized insoluble host cell parts remain in solution.

The same applies for sedimentation or filtration. Preferably, the sedimentation is performed over such a sedimentation time which is sufficient to allow the sedimentation of at least 80%, more preferably of at least 90%, and most preferably of at least 95%, or even of 100%, e.g. of at least 80, 81, 82, 83, 84, 85, 86, 87, 88, 89, 90, 91, 92, 93, 94, 95, 96, 97, 98, 99, 99.9%, or 100%, of the insoluble target protein or the insoluble target protein aggregate, while the solubilized insoluble host cell parts or most of the solubilized insoluble host cell parts remain in solution and can easily be discarded. In a preferred embodiment of the method of the present invention, the sedimentation is performed over a time period of between 1 and 24 hours, preferably of between 3 to 15 hours, more preferably of between 5 to 10 hours, e.g. over 1, 2, 3, 4, 5, 6, 7, 8, 9, 10, 11, 12, 13, 14, 15, 16, 17, 18, 19, 20, 21, 22, 23, or 24 hours. The sedimentation time mentioned above allows the sedimentation of at least 80%, preferably of at least 90%, and more preferably of at least 95%, or even of 100%, e.g. of at least 80, 81, 82, 83, 84, 85, 86, 87, 88, 89, 90, 91, 92, 93, 94, 95, 96, 97, 98, 99, 99.9%, or 100%, of the insoluble target protein or the insoluble target protein aggregate, while the solubilized insoluble host cell parts or most of the solubilized insoluble host cell parts remain in solution.

Preferably, the filtration is performed which such a filter pore size which is sufficient to allow the retention of at least 80%, more preferably of at least 90%, and most preferably of at least 95%, or even of 100%, e.g. of at least 80, 81, 82, 83, 84, 85, 86, 87, 88, 89, 90, 91, 92, 93, 94, 95, 96, 97, 98, 99, 99.9%, or 100%, of the insoluble target protein or the insoluble target protein aggregate, while the solubilized insoluble host cell parts or most of the solubilized insoluble host cell parts can pass through the filter pores. Thus, in case that filtration is used as a separation method, the pore size of the filter may be slightly smaller than the insoluble target protein or the insoluble target protein aggregate. In a preferred embodiment of the method of the present invention, the filtration is performed with filters having a pore size of between 10 nm and 200 nm, preferably of between 20 nm and 180 nm, and more preferably of between 50 and 100 nm, e.g. of 10, 15, 20, 25, 30, 35, 40, 45, 50, 60, 70, 80, 90, 100, 110, 120, 130, 140, 150, 160, 170, 180, 190, or 200 nm. These filter pore size parameters allow the retention of at least 80%, preferably of at least 90%, and more preferably of at least 95%, or even of 100%, e.g. of at least 80, 81, 82, 83, 84, 85, 86, 87, 88, 89, 90, 91, 92, 93, 94, 95, 96, 97, 98, 99, 99.9%, or 100%, of the insoluble target protein or the insoluble target protein aggregate, while the solubilized insoluble host cell parts or most of the solubilized insoluble host cell parts can pass through the filter pores.

Preferably, to improve blending of already solubilized and/or incompletely solubilized insoluble host cell parts in the suspension and/or to improve the formation of smaller fragments from already solubilized and/or incompletely solubilized insoluble host cell parts, in order to facilitate the separation of the insoluble target protein or the insoluble target protein aggregate from the solubilized and/or incompletely solubilized insoluble host cell parts in step c), the method further comprises subsequent to step b) and prior to step c) a step b') of homogenization of said suspension, preferably with a homogenizer (e.g. according to the method as described in example 1), or cell lysis, preferably using suitable enzymes. Alternatively, homogenization of said suspension is preformed via a ballmill or sonification.

It is preferred that, in order to remove further impurities such as cell debris, fermentation remnants, base, denaturant, detergent and/or salts, the method of the present invention further comprises subsequent to step c) a step d) of washing the separated insoluble target protein or the insoluble target protein aggregate, preferably the centrifugate, sediment or retentate. It is more preferred that the method of the present invention further comprises subsequent to step c) a step d) of washing the separated insoluble target protein or the insoluble target protein aggregate, preferably the centrifugate, sediment or retentate, with an aqueous solution, an organic solution, and/or urea.

This further purification step may be required in cases where a culture medium comprising intact host cells comprising the insoluble target protein of interest is provided in step a) of the method of the present invention. This step may not be required in cases where a host cell sediment or a host cell pellet resuspended in water or in an aqueous solution is provided in step a) of the method of the present invention. In the latter cases, the host cells are already separated or mainly separated from the culture medium or fermentation medium and, thus, from all or almost all fermentation remnants and/or impurities.

Preferably, the aqueous solution is a buffered aqueous solution. Further, preferably, the organic solution contains ethanol (EtOH), methanol ($CH_3OH$), hexane ($C_6H_{14}$), diethyl ether ($C_4H_{10}O$) and/or isopropanol ($C_3H_8O$).

As mentioned above, in a more preferred embodiment of the method of the present invention, the separated insoluble target protein or the insoluble target protein aggregate, preferably the centrifugate, sediment or retentate, is subsequent to step c) washed in step d) with urea. The use of urea allows further removal of potentially remaining host cell proteins that have not been separated in step c).

The inventors of the present invention have surprisingly found that the subsequent washing step d) can enhance the purity of the isolated insoluble target protein about up to 5 to 20%, e.g. up to 5, 6, 7, 8, 9, 10, 11, 12, 13, 14, 15, 16, 17, 18, 19 or 20%. For example, an isolated insoluble target protein having after the separation step c) a purity of 80, 81, 82, 83, 84, 85, 86, 87, 88, 89, 90, 91, 92, 93, 94, or 95% without a subsequent washing step d), may have a purity of 85, 86, 87, 88, 89, 90, 91, 92, 93, 94, 95, 96, 97, 98, 99, or 100% after a subsequent washing step d).

Preferably, the method of the present invention is carried out at a temperature of between 4° C. and 60° C., more preferably of between 15° C. and 40° C., and most preferably of between 15° C. and 25° C., or of between 20° C. and 25° C., e.g. of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60° C.

Preferably, the method of the present invention is carried out at a pressure of between 10 kPa and 1000 kPa, preferably of between 50 kPa and 150 kPa, e.g. of 10, 20, 30, 40, 50, 60, 70, 80, 90, 100, 150, 200, 250, 300, 350, 400, 450, 500, 550, 600, 650, 700, 750, 800, 850, 900, 950, or 1000 kPa.

It is preferred that the method of isolating an insoluble target protein (e.g. a spider silk protein) from a culture medium, cell sediment or buffered solution of intact bacterial host cells comprises the steps of:
a) providing (i) a culture medium of intact bacterial host cells comprising an insoluble target protein (e.g. a spider silk protein) and insoluble bacterial host cell parts, (ii) a cell sediment of intact bacterial host cells comprising an insoluble target protein (e.g. a spider silk protein) and insoluble bacterial host cell parts, preferably having a residual moisture content of 20%, or (iii) a buffered solution wherein said cell sediment is resuspended,
b) adding NaOH at a final concentration of between 0.05 M to 0.15 M, preferably of 0.05 M, to said (i) culture medium, (ii) cell sediment or (iii) buffered solution, in order to disrupt said bacterial host cells and to solubilize said insoluble bacterial host cell parts, and
c) separating the insoluble target protein (e.g. a spider silk protein) from the solubilized insoluble bacterial host cell parts by centrifuging between 3000×g and 12000×g, i.e. the insoluble target protein is present as precipitate and the solubilized insoluble bacterial host cell parts are in the supernatant which can be discarded,
wherein in step b) the target protein remains insoluble, and wherein at least 80% or 85%, preferably 95%, of the insoluble bacterial host cell parts are solubilized.

It is also preferred that the method of isolating an insoluble target protein (e.g. a spider silk protein) from a culture medium, cell sediment or buffered solution of disrupted bacterial host cells comprises the steps of:
a) providing (i) a culture medium of disrupted bacterial host cells comprising an insoluble target protein (e.g. a spider silk protein) and insoluble bacterial host cell parts, (ii) a cell sediment of disrupted bacterial host cells comprising an insoluble target protein (e.g. a spider silk protein) and insoluble bacterial host cell parts, preferably having a residual moisture content of 15%, or (iii) a buffered solution wherein said cell sediment is resuspended,
b) adding NaOH at a final concentration of between 0.05 M to 0.15 M, preferably of 0.15 M, to said (i) culture medium, (ii) cell sediment or (iii) buffered solution in order to solubilize said insoluble bacterial host cell parts, and
c) separating the insoluble target protein (e.g. a spider silk protein) from the solubilized insoluble bacterial host cell parts by centrifuging between 3000×g and 12000×g, i.e. the insoluble target protein is present as precipitate and the solubilized insoluble bacterial host cell parts are in the supernatant which can be discarded,
wherein in step b) the target protein remains insoluble, and wherein at least 80% or 85%, preferably 95%, of the insoluble bacterial host cell parts are solubilized.

The terms "polypeptide" and "protein" are used interchangeably herein and mean any peptide-linked chain of amino acids, regardless of length or post-translational modification.

Any insoluble target protein, preferably insoluble target protein aggregate, as defined above, may be isolated with the method of the present invention. However, it is preferred that the insoluble target protein, preferably insoluble target protein aggregate, is selected from the group consisting of a silk protein, particularly a silk protein comprising at least two identical repetitive units (e.g. an arthropod silk protein such as a spider silk protein or an insect silk protein), collagen, resilin, and keratin. Preferably, the collagen is a mussel byssus protein or a human collagen. Preferably the keratin is human keratin.

In the context of the present invention, the term "silk protein", "collagen", "resilin", or "keratin" may refer to a protein such as a recombinant protein that is expressed in a host cell (e.g. microbial, insect, or plant host cell) such as a recombinant host cell or expression system (e.g. microbial, insect, or plant expression system) such as a recombinant expression system, i.e. separated from its natural milieu. Further, in the context of the present invention, the term "isolated silk protein", "isolated collagen", "isolated resilin", or "isolated keratin" may refer to a protein such as a recombinant protein that is expressed in a host cell (e.g. microbial, insect, or plant host cell) such as a recombinant host cell or expression system (e.g. microbial, insect, or plant expression system) such as a recombinant expression system, i.e. separated from its natural milieu, and which is isolated from said host cell or said expression system. The afore-mentioned terms "expression system" and "host cell" are used interchangeably herein.

A "silk protein", as used in the context of the present invention, further refers to a protein with an amino acid sequence which comprises or consists of at least 50%, 60%, 65%, 70%, 75%, 80%, 85%, 90%, preferably at least 95% and most preferably 100% of multiple copies of one identical repetitive unit (e.g. $A_2$, $Q_6$, or $C_{16}$, wherein the items 2, 6, or 16 represent the number of repetitive units) or multiple copies of two or more different repetitive units (e.g. $(AQ)_{24}$, or $(AQ)_{12}C_{16}$).

The terms "repetitive unit" and "repeat unit" can interchangeable be used in the context of the present invention.

In the context of the present invention, the term "silk protein" also refers to a silk protein that comprises or consists of at least two identical repetitive units which comprise or consists of identical copies of amino acid sequences of naturally-occurring silk polypeptides or of variations of amino acid sequences of naturally-occurring silk polypeptides or of combinations of both.

In the context of the present invention, a "repetitive unit" refers to a region which corresponds in amino acid sequence to a region that comprises or consists of at least one peptide motif (e.g. AAAAAA (SEQ ID NO: 13) or GPGQQ (SEQ ID NO: 4)) that repetitively occurs within a naturally occurring silk polypeptide (e.g. MaSpI, ADF-3, ADF-4, or Flag) (i.e. identical amino acid sequence) or to an amino acid sequence substantially similar thereto (i.e. variational amino acid sequence). In this regard "substantially similar" means a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, preferably over the whole length of the respective reference naturally occurring amino acid sequence. A "repetitive unit" having an amino acid sequence which is "substantially similar" to a corresponding amino acid sequence within a naturally occurring silk polypeptide (i.e. wild-type repetitive unit) is also similar with respect to its properties, e.g. a silk protein comprising the "substantially similar repetitive unit" is still insoluble and retains its insolubility and can, thus, still be separated from the solubilized insoluble host cell parts in step c) of the method of the present invention. Preferably, a silk protein comprising the "substantially similar repetitive unit" is insoluble in an aqueous solution, e.g. buffered aqueous solution, in a culture medium, in a fermentation medium, in technical water or in deionized water and stays insoluble to more than 80, 85, 90, 91, 92, 93, 94, 95, 96, 97, 98, 99, 99.9% or even to 100% in an aqueous solution, e.g. buffered aqueous solution, in a culture medium, in a fermentation medium, in technical water or deionized water comprising a base (e.g. NaOH, 0.005 to 1M) over a period of 10 to 90 minutes, e.g. over 10, 15, 20, 25, 30, 35, 40, 45, 50, 55, 60, 65, 70, 75, 80, 85, or 90 minutes and/or at a temperature between 4 and 60° C., e.g. at 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, or 60° C. In preferred embodiments of the present invention, a silk protein comprising the "substantially similar repetitive unit", which remains/stays insoluble, is separated/isolated from the solubilized insoluble host cell parts by filtration, preferably using a filter membrane having a pore size of 10 nm to 200 nm, and/or by centrifugation, preferably at 3000 to 12000×g and more preferably at 4000 to 8000×g, for 10 to 40 min, preferably 20 to 40 min.

A "repetitive unit" having an amino acid sequence which is "identical" to the amino acid sequence of a naturally occurring silk polypeptide, for example, can be a portion of a silk polypeptide corresponding to one or more peptide motifs of MaSpI (SEQ ID NO: 43) MaSpII (SEQ ID NO: 44), ADF-3 (SEQ ID NO: 1) and/or ADF-4 (SEQ ID NO: 2). A "repetitive unit" having an amino acid sequence which is "substantially similar" to the amino acid sequence of a naturally occurring silk polypeptide, for example, can be a portion of a silk polypeptide corresponding to one or more peptide motifs of MaSpI (SEQ ID NO: 43) MaSpII (SEQ ID NO: 44), ADF-3 (SEQ ID NO: 1) and/or ADF-4 (SEQ ID NO: 2), but having one or more amino acid substitution at specific amino acid positions.

The "repetitive unit" does not include the non-repetitive hydrophilic amino acid domain generally thought to be present at the amino and/or carboxyl terminus of naturally occurring silk polypeptides.

A "repetitive unit" according to the present invention further refers to an amino acid sequence with a length of 3 to 200 amino acids, or 5 to 150 amino acids, preferably with a length of 10 to 100 amino acids, or 15 to 80 amino acids and more preferably with a length of 18 to 60, or 20 to 40 amino acids. For example, the repetitive unit according to the present invention can have a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 amino acids. Most preferably, the repetitive unit according to the invention consists of 3, 4, 5, 6, 7, 8, 9, 10, 12, 15, 18, 20, 24, 27, 28, 30, 34, 35, or 39 amino acids.

The silk protein isolated with the method of the present invention preferably consists of between 6 to 1500 amino acids, or between 200 to 1300 amino acids and most preferably between 250 to 1200 amino acids, or between 500 to 1000 amino acids.

Preferably, the silk protein isolated with the method of the present invention comprises or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units. For example, the silk protein isolated with the method of the present invention can comprise or consists of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units. Most preferably, the silk polypeptide comprises 4, 8, 12, 16, 24, 32 or 48 repetitive units. As mentioned above, at least two of the repetitive units comprised in the silk polypeptide isolated with the method of the present invention are identical repetitive units. Thus, the silk polypeptide isolated with the method of the present invention may comprise multiple copies of one identical repetitive unit (e.g. $A_2$ or $C_{16}$, wherein the items 2 or 16 represent the number of repetitive units) or multiple copies of two or more different repetitive units (e.g. $(AQ)_{24}$ or $(QAQ)_8$). For example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 of the 80 repetitive units which may be comprised in the silk polypeptide isolated with the method of the present invention are identical repetitive units.

The silk polypeptide isolated with the method of the present invention can comprise or consist of an amino acid sequence of any silk polypeptide known to one skilled in the art. It is preferred that the silk polypeptide isolated with in the method of the present invention comprises or consists of an amino acid sequence of an arthropod silk polypeptide, preferably of a spider silk polypeptide, or an insect silk polypeptide. The silk polypeptide isolated with the method of the present invention can also comprise or consist of an amino acid sequence of a mussel silk polypeptide.

It is preferred that the spider silk polypeptide comprises or consists of an amino acid sequence of a major ampullate gland polypeptide, such as a dragline spider silk polypeptide, a minor ampullate gland polypeptide, a flagelliform polypeptide, an aggregate spider silk polypeptide, an aciniform spider silk polypeptide or a pyriform spider silk polypeptide. Most preferably, the spider silk polypeptide comprises or consists of an amino acid sequence of a dragline spider silk polypeptide or a flagelliform spider silk polypeptide. It is generally preferred to select the amino acid sequence of the dragline polypeptide or flagelliform polypeptide of a dragline polypeptide or flagelliform polypeptide of orb-web spiders of Araneidae or Araneoids.

It is preferred that the insect silk polypeptide comprises or consists of an amino acid sequence of a silk polypeptide of Lepidoptera. More preferably, the insect silk polypeptide comprises or consists of an amino acid sequence of a silk polypeptide of Bombycidae, most preferably of *Bombyx mori*.

Preferably, the above mentioned silk polypeptides are recombinantly produced, i.e. are recombinant silk polypeptides. For example, the silk polypeptides isolated with the method of the present invention are recombinant spider silk polypeptides such as dragline spider silk polypeptides or flagelliform spider silk polypeptides, recombinant insect silk polypeptides, or recombinant mussel silk polypeptides.

The repetitive unit of the silk polypeptide isolated with the method of the present invention can comprise or consist of an amino acid sequence of any region that comprises or consists of at least one peptide motif that repetitively occurs within a naturally occurring silk polypeptide known to one skilled in the art. Preferably, the repetitive unit of the silk polypeptide isolated with the method of the present invention comprises or consists of an amino acid sequence of a region that comprises or consists of at least one peptide motif that repetitively occurs within an arthropod silk polypeptide, more preferably within a spider silk polypeptide, or an insect silk polypeptide. The repetitive unit of the silk polypeptide isolated with the method of the present invention can also comprise or consist of an amino acid sequence of a region that comprises or consists of at least one peptide motif that repetitively occurs within a mussel silk polypeptide.

It is preferred that the spider silk repetitive unit comprises or consists of an amino acid sequence of a region that comprises or consists of at least one peptide motif that repetitively occurs within a naturally occurring major ampullate gland polypeptide, such as a dragline spider silk polypeptide, a minor ampullate gland polypeptide, a flagelliform polypeptide, an aggregate spider silk polypeptide, an aciniform spider silk polypeptide or a pyriform spider silk polypeptide. Most preferably, the repetitive unit comprises or consists of an amino acid sequence of a region that comprises or consists of at least one peptide motif that repetitively occurs within a naturally occurring dragline spider silk polypeptide or a flagelliform spider silk polypeptide.

It is preferred that the insect silk repetitive unit comprises or consists of an amino acid sequence of a region that comprises or consists of at least one peptide motif that repetitively occurs within a naturally occurring silk polypeptide of Lepidoptera. More preferably, the insect silk repetitive unit comprises or consists of an amino acid sequence of a region that comprises or consists of at least one peptide motif that repetitively occurs within a naturally occurring insect silk polypeptide of Bombycidae, most preferably of *Bombyx mori*.

The term "consensus sequence" as used in the context of the present invention refers to an amino acid sequence which contains amino acids which frequently occur in a certain position (e.g. "G") and wherein, other amino acids which are not further determined are replaced by the place holder "X".

Preferably, the silk protein isolated with the method of the present invention comprises, essentially consists of, or consists of at least two identical repetitive units each comprising at least one, preferably one, consensus sequence selected from the group consisting of:

i) GPGXX (SEQ ID NO: 3), wherein X is any amino acid, preferably in each case independently selected from A, S, G, Y, P, and Q;

ii) GGX, wherein X is any amino acid, preferably in each case independently selected from Y, P, R, S, A, T, N and Q, more preferably in each case independently selected from Y, P and Q; and iii) $A_x$, wherein x is an integer from 5 to 10 (SEQ ID NO: 45).

It is also preferred that the silk protein isolated with the method of the present invention comprises or consists of at least two identical repetitive units each comprising at least one, preferably one, amino acid sequence selected from the group consisting of: GGRPSDTYG (SEQ ID NO: 18) and GGRPSSSYG (SEQ ID NO: 19).

The iterated (peptide) motifs GPGXX (SEQ ID NO: 3) and GGX, i.e. glycine rich motifs, provide flexibility to the silk polypeptide and thus, to the thread formed from the silk protein containing said motifs. In detail, the iterated GPGXX (SEQ ID NO: 3) motif forms turn spiral structures, which imparts elasticity to the silk polypeptide. Major ampullate and flagelliform silks both have a GPGXX (SEQ ID NO: 3) motif. The iterated GGX motif is associated with a helical structure having three amino acids per turn and is found in most spider silks. The GGX motif may provide additional elastic properties to the silk. The iterated polyalanine $A_x$ (peptide) motif forms a crystalline β-sheet structure that provides strength to the silk polypeptide. (WO 03/057727). The GGRPSDTYG (SEQ ID NO: 18) and GGRPSSSYG (SEQ ID NO: 19) (peptide) motifs have been selected from Resilin (WO 2008/155304). Resilin is an elastomeric protein found in most arthropods (arthropoda). It is located in specialised regions of the cuticle, providing low stiffness and high strength (Elvin et al., Nature (473): 999-1002, 2005).

Thus, in a preferred embodiment of the present invention, the silk protein comprises or consists of repetitive units each comprising at least one (e.g. 1, 2, 3, 4, 5, 6, 7, 8, or 9), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGGG (SEQ ID NO: 10), GPGQG (SEQ ID NO: 40), and GPGGS (SEQ ID NO: 11). In another preferred embodiment of the present invention, the silk polypeptide comprises or consists of repetitive units each comprising at least one (e.g. 1, 2, 3, 4, 5, 8, 7, or 8), preferably one, amino acid sequence selected from the group consisting of GGY, GGP, GGA, GGR, GGS, GGT, GGN, and GGQ. In a further preferred embodiment of the present invention, the silk polypeptide comprises or consists of repetitive units each comprising at least one (e.g. 1, 2, 3, 4, 5, or 6), preferably one, amino acid sequence selected from the group consisting of AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), and AAAAAAAAAA (SEQ ID NO: 17).

In another preferred embodiment of the invention, the silk protein comprises or consists of repetitive units each comprising at least one (e.g. 1, 2, 3, 4, 5, 6, 7, 8, 9, 10, 11, 12, 13, 14, 15, 16, 17, 18, 19, 20, 21, 22, 23, 24, or 25), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGGG (SEQ ID NO: 10), GPGQG (SEQ ID NO: 40), GPGGS (SEQ ID NO: 11), GGY, GGP, GGA, GGR, GGS, GGT, GGN, GGQ, AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), AAAAAAAAAA (SEQ ID NO: 17), GGRPSDTYG (SEQ ID NO: 18) and GGRPSSSYG (SEQ ID NO: 19).

Most preferably, the silk protein isolated with the method of the present invention comprises, essentially consists of, or consists of repetitive units, which comprise or consist of
  (i) GPGAS (SEQ ID NO: 5), AAAAAA (SEQ ID NO: 13), GGY, and GPGSG (SEQ ID NO: 6) as amino acid sequence, preferably in this order,
  (ii) AAAAAAAA (SEQ ID NO: 15), GPGGY (SEQ ID NO: 7), GPGGY (SEQ ID NO: 7), and GPGGP (SEQ ID NO: 8) as amino acid sequence, preferably in this order,
  (iii) GPGQQ (SEQ ID NO: 4), GPGQQ (SEQ ID NO: 4), GPGQQ (SEQ ID NO: 4) and GPGQQ (SEQ ID NO: 4) as amino acid sequence,
  (iv) GPGGA (SEQ ID NO: 9), GGP, GPGGA (SEQ ID NO: 9), GGP, GPGGA (SEQ ID NO: 9), and GGP as amino acid sequence, preferably in this order,
  (v) AAAAAAAA (SEQ ID NO: 15), GPGQG (SEQ ID NO: 40), and GGR as amino acid sequence, preferably in this order,
  (vi) AAAAAAAA (SEQ ID NO: 15), GPGGG (SEQ ID NO: 10), GGR, GGN, and GGR as amino acid sequence, preferably in this order,
  (vii) GGA, GGA, GGA, GGS, GGA, and GGS as amino acid sequence, preferably in this order, and/or
  (viii) GPGGA (SEQ ID NO: 9), GPGGY (SEQ ID NO: 7), GPGGS (SEQ ID NO: 11), GPGGY (SEQ ID NO: 7), GPGGS (SEQ ID NO: 11), and GPGGY (SEQ ID NO: 7) as amino acid sequence, preferably in this order.

It should be noted that at least two of the repetitive units comprised in the silk polypeptides mentioned above are identical repetitive units.

Preferably, the silk polypeptide isolated with the method of the present invention comprises, essentially consists of, or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, each comprising at least one, preferably one, consensus sequence selected from the group consisting of:
  i) GPGXX (SEQ ID NO: 3), wherein X is any amino acid, preferably in each case independently selected from A, S, G, Y, P, and Q;
  ii) GGX, wherein X is any amino acid, preferably in each case independently selected from Y, P, R, S, A, T, N and Q, more preferably in each case independently selected from Y, P and Q; and
  iii) $A_x$, wherein x is an integer from 5 to 10.

As mentioned above, at least two of the repetitive units comprised in the silk polypeptide isolated with the method of the present invention are identical repetitive units.

It is also preferred that the silk protein isolated with the method of the present invention comprises or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, each comprising at least one, preferably one, amino acid sequence selected from the group consisting of: GGRPSDTYG (SEQ ID NO: 18) and GGRPSSSYG (SEQ ID NO: 19).

Thus, the silk protein isolated with in the method of the present invention preferably comprises or consists of between 2 to 80 repetitive units, between 3 to 80 repetitive units, or between 4 to 60 repetitive units, more preferably between 8 to 48 repetitive units, or between 10 to 40 repetitive units and most preferably between 16 to 32 repetitive units, each comprising at least one (e.g. 1, 2, 3, 4, 5, 6, 7, 8, 9, 10, 11, 12, 13, 14, 15, 16, 17, 18, 19, 20, 21, 22, 23, 24, or 25), preferably one, amino acid sequence selected from the group consisting of GPGAS (SEQ ID NO: 5), GPGSG (SEQ ID NO: 6), GPGGY (SEQ ID NO: 7), GPGGP (SEQ ID NO: 8), GPGGA (SEQ ID NO: 9), GPGQQ (SEQ ID NO: 4), GPGQG (SEQ ID NO: 40), GPGGG (SEQ ID NO: 10), GPGGS (SEQ ID NO: 11), GGY, GGP, GGA, GGR, GGS, GGT, GGN, GGQ, AAAAA (SEQ ID NO: 12), AAAAAA (SEQ ID NO: 13), AAAAAAA (SEQ ID NO: 14), AAAAAAAA (SEQ ID NO: 15), AAAAAAAAA (SEQ ID NO: 16), AAAAAAAAAA (SEQ ID NO: 17), GGRPSDTYG (SEQ ID NO: 18) and GGRPSSSYG (SEQ ID NO: 19).

Most preferably, the silk protein isolated with the method of the present invention comprises, essentially consists of, or consists of
  (i) repetitive units which comprise or consist of GPGAS (SEQ ID NO: 5), AAAAAA (SEQ ID NO: 13), GGY, and GPGSG (SEQ ID NO: 6) as amino acid sequence, preferably in this order,
  (ii) repetitive units which comprise or consist of AAAAAAAA (SEQ ID NO: 15), GPGGY (SEQ ID NO: 7), GPGGY (SEQ ID NO: 7), and GPGGP (SEQ ID NO: 8) as amino acid sequence, preferably in this order,
  (iii) repetitive units which comprise or consist of GPGQQ (SEQ ID NO: 4), GPGQQ (SEQ ID NO: 4), GPGQQ (SEQ ID NO: 4) and GPGQQ (SEQ ID NO: 4) as amino acid sequence,
  (iv) repetitive units which comprise or consist of GPGGA (SEQ ID NO: 9), GGP, GPGGA (SEQ ID NO: 9), GGP, GPGGA (SEQ ID NO: 9), and GGP as amino acid sequence, preferably in this order,
  (v) repetitive units which comprise or consist of AAAAAAAA (SEQ ID NO: 15), GPGQG (SEQ ID NO: 40), and GGR as amino acid sequence, preferably in this order,
  (vi) repetitive units which comprise or consist of AAAAAAAA (SEQ ID NO: 15), GPGGG (SEQ ID NO: 10), GGR, GGN, and GGR as amino acid sequence, preferably in this order,
  (vii) repetitive units which comprise or consist of GGA, GGA, GGA, GGS, GGA, and GGS as amino acid sequence, preferably in this order, and/or
  (viii) repetitive units which comprise or consist of GPGGA (SEQ ID NO: 9), GPGGY (SEQ ID NO: 7), GPGGS (SEQ ID NO: 11), GPGGY (SEQ ID NO: 7), GPGGS (SEQ ID NO: 11), and GPGGY (SEQ ID NO: 7) as amino acid sequence, preferably in this order.

It should be noted that at least two of the repetitive units comprised in the silk polypeptides mentioned above are identical repetitive units.

Preferably, the silk polypeptide isolated with the method of the present invention comprises, essentially consists of, or consists of
(i) (GPGXX)$_n$ as a repetitive unit, wherein X is any amino acid, preferably in each case independently selected from A, S, G, Y, P, and Q and n is 2, 3, 4, 5, 6, 7, 8, or 9 (SEQ ID NOS: 46-52);
ii) (GGX)$_n$ as a repetitive unit, wherein X is any amino acid, preferably in each case independently selected from Y, P, R, S, A, T, N and Q, more preferably in each case independently selected from Y, P and Q, and n is 2, 3, 4, 5, 6, 7, or 8 (SEQ ID NOS: 53-59); and/or
iii) (A$_x$)$_n$ as a repetitive unit, wherein x is an integer from 5 to 10 and n is 2, 3, 4, 5, 6, 7, 8, 9, or 10 (SEQ ID NOS: 60-68).

As mentioned above, at least two of the repetitive units comprised in the silk polypeptides isolated with the method of the present invention are identical repetitive units.

It is preferred that the repetitive units are independently selected from module A (SEQ ID NO: 20), module C (SEQ ID NO: 21), module Q (SEQ ID NO: 22), module K (SEQ ID NO: 23), module sp (SEQ ID NO: 24), module S (SEQ ID NO: 25), module R (SEQ ID NO: 26), module X (SEQ ID NO: 27), or module Y (SEQ ID NO: 28), or variants thereof (i.e. module A variants, module C variants, module Q variants, module K variants, module sp variants, module S variants, module R variants, module X variants or module Y variants). The modules A (SEQ ID NO: 20) and Q (SEQ ID NO: 22) are based on the amino acid sequence of ADF-3 of the spider *Araneus diadematus*. Module C (SEQ ID NO: 21) is based on the amino acid sequence of ADF-4 of the spider *Araneus diadematus*. The modules K (SEQ ID NO: 23), sp (SEQ ID NO: 24), X (SEQ ID NO: 27) and Y (SEQ ID NO: 28) are based on the amino acid sequence of the flagelliform protein FLAG of the spider *Nephila clavipes* (WO 2006/008163). The modules S (SEQ ID NO: 25) and R (SEQ ID NO: 26) are based on Resilin (Arthropoda) (WO 2008/155304).

Thus, in a preferred embodiment of the present invention, the repetitive units of the silk polypeptide consist of module A: GPYGPGASAAAAAAGGYGPGSGQQ (SEQ ID NO: 20), module C: GSSAAAAAAAASGPGGYGPENQGPSGPGGYGPGGP (SEQ ID NO: 21), module Q: GPGQQGPGQQGPGQQGPGQQ (SEQ ID NO: 22), module K: GPGGAGGPYGPGGAGGPYGPGGAGGPY (SEQ ID NO: 23), module sp: GGTTIIEDLDITIDGADGPITISEELTI (SEQ ID NO: 24), module S: PGSSAAAAAAAASGPGQGQGQGQGGRPSDTYG (SEQ ID NO: 25), module R: SAAAAAAAAGPGGGNGGRPSDTYGAPGGGNGGRPSSSYG (SEQ ID NO: 26), module X: GGAGGAGGAGGSGGAGGS (SEQ ID NO: 27), or module Y: GPGGAGPGGYGPGGSGPGGYGPGGSGPGGY (SEQ ID NO: 28), or variants thereof.

Preferably, the silk protein isolated with the method of the present invention comprises, essentially consist of, or consists of between 2 o 80 repetitive units, between 3 to 80 repetitive units, or between 4 to 60 repetitive units, more preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module A (SEQ ID NO: 20), module C (SEQ ID NO: 21), module Q (SEQ ID NO: 22), module K (SEQ ID NO: 23), module sp (SEQ ID NO: 24), module S (SEQ ID NO: 25), module R (SEQ ID NO: 26), module X (SEQ ID NO: 27) or module Y (SEQ ID NO: 28), or variants thereof (i.e. module A variants, module C variants, module Q variants, module K variants, module sp variants, module S variants, module R variants, module X variants or module Y variants). It should be noted that at least two of the repetitive units comprised in the silk polypeptide isolated with the method of the present invention are identical repetitive units (modules).

Thus, it is preferred that the silk polypeptide isolated with the method of the present invention comprises, essentially consists of, or consists of (i) repetitive unit(s) consisting of module A and/or repetitive unit(s) consisting of module A variants, (ii) repetitive unit(s) consisting of module C and/or repetitive unit(s) consisting of module C variants, (iii) repetitive unit(s) consisting of module Q and/or repetitive unit(s) consisting of module Q variants, (iv) (a) repetitive unit(s) consisting of module A and repetitive unit(s) consisting of module Q, (b) repetitive unit(s) consisting of module A and repetitive unit(s) consisting of module Q variants, (c) repetitive unit(s) consisting of module A variants and repetitive unit(s) consisting of module Q, (d) repetitive unit(s) consisting of module A variants and repetitive unit(s) consisting of module Q variants, (v) (a) repetitive unit(s) consisting of module A and repetitive unit(s) consisting of module C, (b) repetitive unit(s) consisting of module A and repetitive unit(s) consisting of module C variants, (c) repetitive unit(s) consisting of module A variants and repetitive unit(s) consisting of module C, (d) repetitive unit(s) consisting of module A variants and repetitive unit(s) consisting of module C variants, (vi) (a) repetitive unit(s) consisting of module C and repetitive unit(s) consisting of module Q, (b) repetitive unit(s) consisting of module C and repetitive unit(s) consisting of module Q variants, (c) repetitive unit(s) consisting of module C variants and repetitive unit(s) consisting of module Q, (d) repetitive unit(s) consisting of module C variants and repetitive unit(s) consisting of module Q variants, or (vii) (a) repetitive unit(s) consisting of module A, repetitive unit(s) consisting of module Q and repetitive unit(s) consisting of module C, (b) repetitive unit(s) consisting of module A, repetitive unit(s) consisting of module Q and repetitive unit(s) consisting of module C variants, (c) repetitive unit(s) consisting of module A, repetitive unit(s) consisting of module Q variants and repetitive unit(s) consisting of module C, (d) repetitive unit(s) consisting of module A variants, repetitive unit(s) consisting of module Q and repetitive unit(s) consisting of module C, (e) repetitive unit(s) consisting of module A, repetitive unit(s) consisting of module Q variants and repetitive unit(s) consisting of module C variants, (f) repetitive unit(s) consisting of module A variants, repetitive unit(s) consisting of module Q variants and repetitive unit(s) consisting of module C, (g) repetitive unit(s) consisting of module A variants, repetitive unit(s) consisting of module Q and repetitive unit(s) consisting of module C variants, (h) repetitive unit(s) consisting of module A variants, repetitive unit(s) consisting of module Q variants and repetitive unit(s) consisting of module C variants.

The modules A, C, Q, K, sp, S, R, X or Y or variants thereof (i.e. module A variants, module C variants, module Q variants, module K variants, module sp variants, module S variants, module R variants, module X variants or module Y variants) can also be combined with each other in any combination and in any number of each, i.e. module (repetitive unit) A can be combined with module (repetitive unit) Q (i.e.

combination AQ), module (repetitive unit) C can be combined with module (repetitive unit) Q (i.e. combination CQ), module (repetitive unit) Q can be combined with module (repetitive unit) A and with module (repetitive unit) Q (i.e. combination QAQ), module (repetitive unit) A can be combined with module (repetitive unit) A and with module (repetitive unit) Q (i.e. combination AAQ), etc., under the proviso that the silk polypeptide isolated with the method of the present invention comprises or consists of at least two repetitive units which are identical. For example, the silk polypeptide isolated with the method of the present invention can comprise or consist of $A_n$, $(AA)_n$, $(AQ)_n$, $(QA)_n$, $Q_n$, $(QQ)_n$, $(QAQ)_n$, $(AQA)_n$, $C_n$, $(CC)_n$, $(CCC)_n$, $(CQ)_n$, $(QC)_n$, $(QCQ)_n$, $(CQC)_n$, $(AA)_nQ_n$, $(QQ)_nA_n$, $(AAA)_nQ_n$, $(QQQ)_nA_n$, $(AQQ)_n$, $(QQA)_n$, $K_n$, $sp_n$, $S_n$, $R_n$, $X_n$, $Y_n$, $(Ksp)_n$, $(spK)_n$, $(XY)_n$, $(YX)_n$, $(XX)_n$, $(YY)_n$, $(XXX)_n$, $(YYY)_n$, $(AX)_n$, $(XA)_n$, $(CX)_n$, $(XC)_n$, $(QX)_n$, $(XQ)_n$, $(YQ)_n$, $(QY)_n$, $(SS)_n$, $(SR)_n$, $(RS)_n$, or $(RR)_n$, wherein n is at least 2, preferably 4, 8, 9, 10, 12, 16, 20, 24, or 32. In case that the silk polypeptide consists of $(AQ)_{12}$, it is noted that module (repetitive unit) A is 12 times present and module (repetitive unit) Q is also 12 times present in the silk polypeptide and that, thus, the silk polypeptide consists of 24 modules (repetitive units). The arrangement of the modules (repeat units) of a silk polypeptide consisting of $(AQ)_{12}$ is as follows: AQAQAQAQAQAQAQAQAQAQAQAQ. Further, in case that the silk polypeptide of the modules (repeat units) of a silk polypeptide consists of $(QAQ)_8$, it is noted that module (repeat unit) A is 8 times present and module (repetitive unit) Q is 16 times present in the silk polypeptide and that, thus, the silk polypeptide consists of 24 modules (repetitive units). The arrangement of the modules (repeat units) of a silk polypeptide consisting of $(QAQ)_8$ is as follows: QAQQAQQAQQAQQAQQAQQAQQAQ.

The silk polypeptide isolated with the method of the present invention can also comprise or consist of $(A^*Q)_n$, $(AQ^*)_n$, $(A^*Q^*)_n$, $(Q^*A)_n$, $(QA^*)_n$, $(Q^*A^*)_n$, $(QAQ^*)_n$, $(QA^*Q)_n$, $(Q^*AQ)_n$, $(QA^*Q^*)_n$, $(Q^*A^*Q)_n$, $(Q^*AQ^*)_n$, $(Q^*A^*Q^*)_n$, $(AQA^*)_n$, $(AQ^*A)_n$, $(A^*QA)_n$, $(AQ^*A^*)_n$, $(A^*Q^*A)_n$, $(A^*QA^*)_n$, $(A^*Q^*A^*)_n$, wherein n is at least 2, preferably 4, 8, 9, 10, 12, 16, 20, 24, or 32 and wherein indicates a module variant, i.e. module A or Q variant.

The terms "combined with each other" or "concatenated with each other" may mean in the context of the present invention that the modules (repetitive units) are directly combined or concatenated with each other or may mean in the context of the present invention that the modules (repetitive units) are combined or concatenated with each other via one or more spacer amino acids. In preferred embodiments, the modules (repetitive units) comprised in the silk polypeptide are directly combined or concatenated with each other. In other preferred embodiments, the modules (repetitive units) comprised in the silk polypeptide are combined or concatenated with each other via 1 to 25 or 1 to 20 spacer amino acids, more preferably via 1 to 15 or 1 to 10 spacer amino acids, and most preferably, via 1 to 5 spacer amino acids, i.e. via 1, 2, 3, 4, 5, 6, 7, 8, 9, 10, 11, 12, 13, 14, 15, 16, 17, 18, 19, 20, 21, 22, 23, 24, or 25 spacer amino acids. Said spacer amino acids may be any amino acids naturally occurring in proteins. Preferably, said spacer amino acid is not proline. Uncharged amino acids such as alanine or glycine are particularly preferred. It is preferred that said spacer amino acids are amino acids which do not change the property of the silk protein to be insoluble and to retain its insolubility, so that said silk protein can still be separated from the solubilized insoluble host cell parts in step c) of the method of the present invention. It is further preferred that said spacer amino acids are amino acids which do not cause steric hindrance, e.g. amino acids having a small size such as alanine or glycine. In more preferred embodiments, the silk polypeptide comprises modules which are directly combined with each other and modules which are combined with each other via 1 to 25 or 1 to 20 spacer amino acids, more preferably via 1 to 15 or 1 to 10 spacer amino acids, and most preferably, via 1 to 5 spacer amino acids, i.e. via 1, 2, 3, 4, 5, 6, 7, 8, 9, 10, 11, 12, 13, 14, 15, 16, 17, 18, 19, 20, 21, 22, 23, 24, or 25 spacer amino acids.

A module A, C, Q, K, sp, S, R, X or Y variant differs from the reference (wild-type) module A, C, Q, K, sp, S, R, X or Y from which it is derived by up to 1, 2, 3, 4, 5, 6, 7, 8, 9, 10, 11, 12, 13, 14, or 15 amino acid changes in the amino acid sequence (i.e. substitutions, additions, insertions, deletions, N-terminal truncations and/or C-terminal truncations). Such a module variant can alternatively or additionally be characterised by a certain degree of sequence identity to the reference (wild-type) module from which it is derived. Thus, a module A, C, Q, K, sp, S, R, X or Y variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference (wild-type) module A, C, Q, K, sp, S, R, X or Y. Preferably, the sequence identity is over a continuous stretch of at least 10, 15, 18, 20, 24, 27, 28, 30, 34, 35, or more amino acids, preferably over the whole length of the respective reference (wild-type) module A, C, Q, K, sp, S, R, X or Y.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference (wild-type) module A, C, Q, K, sp, S, R, X or Y. It is further particularly preferred that the sequence identity is at least 80% over a continuous stretch of at least 10, 15, 18, 20, 24, 28, or 30 amino acids, is at least 85% over a continuous stretch of at least 10, 15, 18, 20, 24, 28, or 30 amino acids, is at least 90% over a continuous stretch of at least 10, 15, 18, 20, 24, 28, or 30 amino acids, is at least 95% over a continuous stretch of at least 10, 15, 18, 20, 24, 28, or 30 amino acids, is at least 98% over a continuous stretch of at least 10, 15, 18, 20, 24, 28, or 30 amino acids, or is at least 99% over a continuous stretch of at least 10, 15, 18, 20, 24, 28, or 30 amino acids of the respective reference (wild-type) module A, C, Q, K, sp, S, R, X or Y.

A fragment (or deletion variant) of module A, C, Q, K, sp, S, R, X or Y has preferably a deletion of up to 1, 2, 3, 4, 5, 6, 7, 8, 9, 10, 11, 12, 13, 14, or 15 amino acids at its N-terminus and/or at its C-terminus. The deletion can also be internally.

Additionally, the module A, C, Q, K, sp, S, R, X or Y variant or fragment is only regarded as a module A, C, Q, K, sp, S, R, X or Y variant or fragment within the context of the present invention, if the modifications with respect to the amino acid sequence on which the variant or fragment is based do not change the property of a silk protein to be insoluble and to retain its insolubility, so that said silk protein can still be separated from the solubilized insoluble host cell parts in step c) of the method of the present invention. Preferably, a silk protein comprising the module A, C, Q, K, sp, S, R, X or Y variant or fragment is insoluble in an aqueous solution, e.g. buffered aqueous solution, in a culture medium, in a fermentation medium, in technical water or in deionized water and stays insoluble to more than 80, 85, 90, 91, 92, 93, 94, 95, 96, 97, 98, 99, 99.9% or even to 100% in an aqueous solution, e.g.

buffered aqueous solution, in a culture medium, in a fermentation medium, in technical water or deionized water comprising a base (e.g. NaOH, 0.005 to 1M) over a period of 10 to 90 minutes, e.g. over 10, 15, 20, 25, 30, 35, 40, 45, 50, 55, 60, 65, 70, 75, 80, 85, or 90 minutes and/or at a temperature between 4 and 60° C., e.g. at 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, or 60° C. In preferred embodiments of the present invention, a silk protein comprising the module A, C, Q, K, sp, S, R, X or Y variant or fragment, which remains/stays insoluble, is separated/isolated from the solubilized insoluble host cell parts by filtration, preferably using a filter membrane having a pore size of 10 nm to 200 nm, and/or by centrifugation, preferably at 3000 to 12000×g and more preferably at 4000 to 8000×g, for 10 to 40 min, preferably 20 to 40 min.

Thus, in a preferred embodiment of the present invention the repetitive units are independently selected from module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34). The modules $A^C$ (SEQ ID NO: 29), $A^K$ (SEQ ID NO: 30), $C^C$ (SEQ ID NO: 31), $C^{K1}$ (SEQ ID NO: 32), $C^{K1}$ (SEQ ID NO: 33) and $C^{KC}$ (SEQ ID NO: 34) are variants of the module A which is based on the amino acid sequence of ADF-3 of the spider *Araneus diadematus* and of module C which is based on the amino acid sequence of ADF-4 of the spider *Araneus diadematus* (WO 2007/025719). In module $A^C$ (SEQ ID NO: 29) the amino acid S (serine) at position 21 has been replaced by the amino acid C (cysteine), in module $A^K$ (SEQ ID NO: 30) the amino acid S at position 21 has been replaced by the amino acid K (lysine), in module $C^C$ (SEQ ID NO: 31) the amino acid S at position 25 has been replaced by the amino acid 25 by C, in module $C^{K1}$ (SEQ ID NO: 32) the amino acid S at position 25 has been replaced by the amino acid K, in module $C^{K2}$ (SEQ ID NO: 33) the amino acid E (glutamate) at position 20 has been replaced by the amino acid K, and in module $C^{KC}$ (SEQ ID NO: 34) the amino acid E at position 20 has been replaced by the amino acid K and the amino acid S at position 25 has been replaced by the amino acid C (WO 2007/025719).

Preferably, the repetitive units in the silk polypeptide isolated with the method of the present invention consists of module $A^C$: GPYGPGASAAAAAAGGYGPGCGQQ (SEQ ID NO: 29), module $A^K$: GPYGPGASAAAAAAGGYGPGKGQQ (SEQ ID NO: 30), module $C^C$: GSSAAAAAAAASGPGGYGPENQGPCGPGGYGPGGP (SEQ ID NO: 31), module $C^{K1}$: GSSAAAAAAAASGPGGYGPENQGPKGPGGYGPGGP (SEQ ID NO: 32), module $C^{K2}$: GSSAAAAAAAASGPGGYGPKNQGPSGPGGYGPGGP (SEQ ID NO: 33), or module $C^{KC}$: GSSAAAAAAAASGPGGYGPKNQGPCGPGGYGPGGP (SEQ ID NO: 34).

It is also preferred that the silk polypeptide isolated with the method of the present invention comprises, essentially consists of, or consists of between 2 to 80 repetitive units, between 3 to 80 repetitive units, or between 4 to 60 repetitive units, preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34). For example, the silk polypeptide isolated with the method of the present invention can comprises or consists of the modules $C^C_4$, $C^C_8$, $C^C_{16}$, $C^C_{32}$, $A^C_5$, $A^C_8$, or $A^C_{10}$. It should be noted that at least two of the repetitive units comprised in the silk polypeptide isolated with the method of the present invention are identical repetitive units (modules).

For example, the silk polypeptide can comprises or consists of the modules $C^C_4$, $C^C_8$, $C^C_{16}$, $C^C_{32}$, $A^C_5$, $A^C_8$, or $A^C_{10}$.

The modules $A^K$, $C^C C^{K2}$ and $C^{KC}$ can also be combined with each other, i.e. module (repetitive unit) $A^K$ can be combined with module (repetitive unit) $C^C$ (i.e. combination $A^K C^C$), module (repetitive unit) $C^{K1}$ can be combined with module (repetitive unit) $C^{K2}$ and with module (repetitive unit) $C^{KC}$ (i.e. combination $C^{K1} C^{K2} C^{KC}$), etc., under the proviso that the silk polypeptide isolated with the method of the present invention comprises or consists of at least two repetitive units which are identical. Thus, the silk polypeptide isolated with the method of the present invention can also comprise or consist of the modules $(A^K)_n$, $(C^C)_n$, $(C^{K1})_n$, $(C^{K2})_n$, $(C^{KC})_n$, $(A^K A^C)_n$, $(C^C C^C)_n$, $(C^{K1} C^{K2})_n$, $(C^{K2} C^{K1})_n$, $(C^{K1} C^{K2} C^{K1})_n$, $(C^{K2} C^{K1} C^{K2})_n$, $(C^{K1} C^{K2} C^{KC})_n$, $(C^{KC} C^{K2} C^{KC})_n$, or $(C^{KC} C^{K2} C^{K1})_n$, wherein n is at least 2, preferably 4, 5, 6, 7, 8, 10, 12, 16, or 20. The term "combined with each other" is defined above.

It is further preferred that the silk polypeptide isolated with the method of the present invention comprises, essentially consists of, or consists of between 2 to 80 repetitive units, between 3 to 80 repetitive units or between 4 to 60 repetitive units, preferably between 8 to 48 repetitive units, or between 10 to 40 repetitive units and most preferably between 16 to 32 repetitive units, i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 repetitive units, which are independently selected from module A (SEQ ID NO: 20) or variants thereof, module C (SEQ ID NO: 21) or variants thereof, module Q (SEQ ID NO: 22) or variants thereof, module K (SEQ ID NO: 23) or variants thereof, module sp (SEQ ID NO: 24) or variants thereof, module S (SEQ ID NO: 25) or variants thereof, module R (SEQ ID NO: 26) or variants thereof, module X (SEQ ID NO: 27) or variants thereof, module Y (SEQ ID NO: 28) or variants thereof, module $A^C$ (SEQ ID NO: 29), module $A^K$ (SEQ ID NO: 30), module $C^C$ (SEQ ID NO: 31), module $C^{K1}$ (SEQ ID NO: 32), module $C^{K2}$ (SEQ ID NO: 33) or module $C^{KC}$ (SEQ ID NO: 34). Again, it should be noted that at least two of the repetitive units comprised in the silk polypeptide isolated with the method of the present invention are identical repetitive units (modules).

The modules $A_K$, $C_C$, $C^{K1}$, $C^{K2}$ and $C^{KC}$ can also be combined with the modules A, C, Q, K, sp, S, R, X or Y, i.e. module (repetitive unit) $A^K$ can be combined with module (repetitive unit) C (i.e. combination $A^K C$), or module (repetitive unit) $C^C$ can be combined with module (repetitive unit) C (i.e. combination $C^C C$), etc., under the proviso that the silk polypeptide isolated with the method of the present invention comprises or consists of at least two repetitive units which are identical. Thus, the silk polypeptide isolated with the method of the present invention can also comprise or consist of the modules $(AQA^K)_n$, $(QA^K)_n$, $(QA^K Q)_n$, $(A^K QA)_n$, $(A^K QA^K)_n$, $(CC^C)_n$, $(CC^C C)_n$, $(C^C C^C C)_n$, $(CC^C C^C)_n$, $(C^C Q)_n$, $(QC^C)_n$, $(QC^C Q)_n$, $(C^C QC)_n$, $(CQC^C)_n$, $(C^C QC^C)_n$, $(CC^{K1})_n$, $(CC^{K1} C)_n$, $(C^{K1} CC)_n$, $(CC^{K1} C)_n$, $(C^{KC} C^{KC} C)_n$, $(CC^{KC} C^{KC})_n$, $(C^{KC} Q)_n$, $(QC^{KC} Q)_n$, $(QC^{KC} Q)_n$, $(A^K C^{K1} Q)_n$, $(QC^{K2} A^K)_n$, or ($C^{K1}C^{K2}C)_n$, wherein n is at least 2, preferably 4, 5, 6, 7, 8, 10, 12, 16, or 20. The term "combined with each other" is defined above.

For example, the silk polypeptide isolated with the method of the present invention comprises or consists of the modules $C_{16}C^C$, $C^CC_{16}$, $C_8C^CC_8$, $C_8C^C_8$, $C^C_8C_8$, $C_4C^C_8C_4$, $C^C_4C_8C^C_4$, $C^C(AQ)_{24}$, or $(AQ)_{24}C^C$.

The silk polypeptide isolated with the method of the present invention can further comprise at least one non-repetitive (NR) unit, i.e. 1, 2, 3, 4, 5, 6, or more NR units, preferably one NR unit. In the context of the present invention, the term "non-repetitive (NR) unit" refers to a region of amino acids present in a naturally occurring silk polypeptide that displays no obvious repetition pattern (non-repetitive unit or NR unit). Preferably, the amino acid sequence of the non-repetitive unit corresponds to a non-repetitive amino acid sequence of naturally occurring dragline polypeptides, preferably of ADF-3 (SEQ ID NO: 1) or ADF-4 (SEQ ID NO: 2), or to an amino acid sequence substantially similar thereto.

It is particularly preferred that the amino acid sequence of the non-repetitive unit corresponds to a non-repetitive carboxy terminal amino acid sequence of naturally occurring dragline polypeptides, preferably of ADF-3 (SEQ ID NO: 1) or ADF-4 (SEQ ID NO: 2), or to an amino acid sequence substantially similar thereto. More preferably, the amino acid sequence of the non-repetitive unit corresponds to a non-repetitive carboxy terminal amino acid sequence of ADF-3 (SEQ ID NO: 1) which comprises amino acids 513 through 636, or of ADF-4 (SEQ ID NO: 2) which comprises amino acids 302 through 410, or to an amino acid sequence substantially similar thereto.

In this regard "substantially similar" means a degree of amino acid identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9%, preferably over 20, 30, 40, 50, 60, 70, 80 or more amino acids, more preferably over the whole length of the respective reference non-repetitive (carboxy terminal) amino acid sequence of naturally occurring dragline polypeptides, preferably of ADF-3 (SEQ ID NO: 1) or ADF-4 (SEQ ID NO: 2).

A "non-repetitive unit" having an amino acid sequence which is "substantially similar" to a corresponding non-repetitive (carboxy terminal) amino acid sequence within a naturally occurring dragline polypeptide (i.e. wild-type non-repetitive (carboxy terminal) unit), preferably within ADF-3 (SEQ ID NO: 1) or ADF-4 (SEQ ID NO: 2), is also similar with respect to its properties, e.g. a silk protein comprising the "substantially similar non-repetitive unit" is still insoluble and retains its insolubility and can, thus, still be separated from the solubilized insoluble host cell parts in step c) of the method of the present invention. Preferably, a silk protein comprising the "substantially similar non-repetitive unit" is insoluble in an aqueous solution, e.g. buffered aqueous solution, in a culture medium, in a fermentation medium, in technical water or in deionized water and stays insoluble to more than 80, 85, 90, 91, 92, 93, 94, 95, 96, 97, 98, 99, 99.9% or even to 100% in an aqueous solution, e.g. buffered aqueous solution, in a culture medium, in a fermentation medium, in technical water or deionized water comprising a base (e.g. NaOH, 0.005 to 1M) over a period of 10 to 90 minutes, e.g. over 10, 15, 20, 25, 30, 35, 40, 45, 50, 55, 60, 65, 70, 75, 80, 85, or 90 minutes and/or at a temperature between 4 and 60° C., e.g. at 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, or 60° C. In preferred embodiments of the present invention, a silk protein comprising the "substantially similar non-repetitive unit", which remains/stays insoluble, is separated/isolated from the solubilized insoluble host cell parts by filtration, preferably using a filter membrane having a pore size of 10 nm to 200 nm, and/or by centrifugation, preferably at 3000 to 12000×g and more preferably at 4000 to 8000×g, for 10 to 40 min, preferably 20 to 40 min.

Most preferably, the non-repetitive (NR) unit is NR3 (SEQ ID NO: 41) or variants thereof, or NR4 (SEQ ID NO: 42) or variants thereof. The NR3 (SEQ ID NO: 41) unit is based on the amino acid sequence of ADF-3 of the spider *Araneus diadematus* and the NR4 (SEQ ID NO: 42) unit is based on the amino acid sequence of ADF-4 of the spider *Araneus diadematus* (WO 2006/008163).

A NR3 or NR4 unit variant differs from the reference NR3 (SEQ ID NO: 41) or NR4 (SEQ ID NO: 42) unit from which it is derived by up to 1, 2, 3, 4, 5, 6, 7, 8, 9, 10, 11, 12, 13, 14, 15, 16, 17, 18, 19, 20, 25, or 30 amino acid changes in the amino acid sequence (i.e. exchanges, insertions, deletions, N-terminal truncations and/or C-terminal truncations). Such a NR3 or NR4 unit variant can alternatively or additionally be characterized by a certain degree of sequence identity to the reference NR3 or NR4 unit from which it is derived. Thus, a NR3 or NR4 unit variant has a sequence identity of at least 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference NR3 or NR4 unit. Preferably, the sequence identity is over a continuous stretch of at least 10, 20, 30, 40, 50, 60, 70, 80, 90, or more amino acids, preferably over the whole length of the respective reference NR3 or NR4 unit.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference NR3 or NR4 unit. It is further particularly preferred that the sequence identity is at least 80% over a continuous stretch of at least 20, 30, 40, 50, 60, 70, or 80 amino acids, is at least 85% over a continuous stretch of at least 20, 30, 40, 50, 60, 70, or 80 amino acids, is at least 90% over a continuous stretch of at least 20, 30, 40, 50, 60, 70, or 80 amino acids, is at least 95% over a continuous stretch of at least 20, 30, 40, 50, 60, 70, or 80 amino acids, is at least 98% over a continuous stretch of at least 20, 30, 40, 50, 60, 70, or 80 amino acids, or is at least 99% over a continuous stretch of at least 20, 30, 40, 50, 60, 70, or 80 amino acids of the respective reference NR3 or NR4 unit.

A fragment (or deletion variant) of a NR3 or NR4 unit has preferably a deletion of up to 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, or 60 amino acids at its N-terminus and/or at its C-terminus. The deletion can also be internally.

Additionally, the NR3 or NR4 unit variant or fragment is only regarded as a NR3 or NR4 unit variant or fragment within the context of the present invention, if the modifications with respect to the amino acid sequence on which the variant or fragment is based do not change the property of a silk protein to be insoluble and to retain its insolubility, so that said silk protein can still be separated from the solubilized insoluble host cell parts in step c) of the method of the present invention. Preferably, a silk protein comprising the NR3 or NR4 unit variant or fragment is insoluble in an aqueous solution, e.g. buffered aqueous solution, in a culture medium, in a fermentation medium, in technical water or in deionized water and stays insoluble to more than 80, 85, 90, 91, 92, 93, 94, 95, 96, 97, 98, 99, 99.9% or even to 100% in an aqueous solution, e.g. buffered aqueous solution, in a culture medium, in a fermentation medium, in technical water or deionized water comprising a base (e.g. NaOH, 0.005 to 1M) over a period of 10 to 90 minutes, e.g. over 10, 15, 20, 25, 30, 35, 40, 45, 50, 55, 60, 65, 70, 75, 80, 85, or 90 minutes and/or at a temperature between 4 and 60° C., e.g. at 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, or 60° C. In preferred embodiments of the present invention, a silk protein comprising the NR3 or NR4 unit variant or fragment, which remains/stays insoluble, is separated/isolated from the solubilized insoluble host cell parts by filtration, preferably using a filter membrane having a pore size of 10 nm to 200 nm, and/or by centrifugation, preferably at 3000 to 12000×g and more preferably at 4000 to 8000×g, for 10 to 40 min, preferably 20 to 40 min.

Preferably, the silk protein isolated with the method of the present invention is selected from the group consisting of ADF-3 (SEQ ID NO: 1) or variants thereof, ADF-4 (SEQ ID NO: 2) or variants thereof, MaSpI (SEQ ID NO: 43) or variants thereof, MaSpII (SEQ ID NO: 44) or variants thereof, $(C)_m$, $(C)_m NR_z$, $NR_z(C)_m$, $NR_z(C)_m NR_z$, $(AQ)_n$, $(AQ)_n NR_z$, $NR_z(AQ)_n$, $NR_z(AQ)_n NR_z$, $(QAQ)_o$, $NR_z(QAQ)_o$, $(QAQ)_o NR_z$, $Y_p$, $X_p$, and $K_p$, wherein m is an integer of 2 to 64 (i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, or 68), n is an integer of 6 to 24 (i.e. 6, 7, 8, 9, 10, 11, 12, 13, 14, 15, 16, 17, 18, 19, 20, 21, 22, 23, or 24), o is an integer of 8 to 16 (i.e. 8, 9, 10, 11, 12, 13, 14, 15, or 16), p is an integer of 8 to 16 (i.e. 8, 9, 10, 11, 12, 13, 14, 15, or 16) and z is an integer of 1 to 3 (i.e. 1, 2, or 3) and NR stands for a non-repetitive unit. The above mentioned formulas are defined by one of the following: In the formula (i) $(C)_m$, a "m" number of C modules, namely 2 to 64 C modules, represented by the amino acid sequence according to SEQ ID NO: 21, are combined with each other, (ii) $(C)_m NR_z$, a "m" number of C modules, namely 2 to 64 C modules, represented by the amino acid sequence according to SEQ ID NO: 21, are combined with each other, wherein said C modules are further combined with a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, (iii) $NR_z(C)_m$, a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, is present (z=1) or are combined with each other (z=2 or 3), wherein said non-repetitive (NR) unit(s) is (are) further combined with a "m" number of C modules, namely 2 to 64 C modules, represented by the amino acid sequence according to SEQ ID NO: 21, (iv) $NR_z(C)_m NR_z$, a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, is present (z=1) or are combined with each other (z=2 or 3), wherein said non-repetitive (NR) unit(s) is (are) further combined with a "m" number of C modules, namely 2 to 64 C modules, represented by the amino acid sequence according to SEQ ID NO: 21, and wherein said C modules are further combined with a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, (v) $(AQ)_n$, a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22, are combined with each other, (vi) $(AQ)_n NR_z$, a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22, are combined with each other, and wherein said A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, (vii) $NR_z(AQ)_n$, a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, is present (z=1) or are combined with each other (z=2 or 3), wherein said non-repetitive (NR) unit(s) is (are) further combined with a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22, (viii) $NR_z(AQ)_n NR_z$, a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, is present (z=1) or are combined with each other (z=2 or 3), wherein said non-repetitive (NR) unit(s) is (are) further combined with a "n" number of A and Q module combinations, namely 6 to 24 A and Q module combinations, wherein module A is represented by the amino acid sequence according to SEQ ID NO: 20 and module Q is represented by the amino acid sequence according to SEQ ID NO: 22, and wherein said A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, (ix) $(QAQ)_o$, a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20, are combined with each other, (x) $(QAQ)_o NR_z$, a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20, are combined with each other, and wherein said Q, A and Q module combinations are further combined with a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, (xi) $NR_z(QAQ)_o$, a "z" number of non-repetitive (NR) units, namely 1 to 3 non-repetitive (NR) units, e.g. the non-repetitive (NR) units NR3 represented by the amino acid sequence according to SEQ ID NO: 41 or NR4 represented by the amino acid sequence according to SEQ ID NO: 42, is present (z=1) or are combined with each other (z=2 or 3), wherein said non-repetitive (NR) unit(s) is (are) further combined with a "o" number of Q, A and Q module combinations, namely 8 to 16 Q, A and Q module combinations, wherein module Q is represented by an amino acid sequence according to SEQ ID NO: 22 and module A is represented by the amino acid sequence according to SEQ ID NO: 20, (xii) $Y_p$, a "p" number of Y modules, namely 8 to 16 Y modules, represented by the amino acid sequence according to SEQ ID NO: 28, are combined with each other, (xiii) $X_P$, a "p" number of X modules, namely 8 to 16× modules, represented by the amino acid sequence according to SEQ ID NO: 27, are combined with each other, and (xiv) $K_p$, a "p" number of K modules, namely 8 to 16 K modules, represented by the amino acid sequence according to SEQ ID NO: 23, are combined with each other.

More preferably, (i) z in $(C)_m NR_z$ or $NR_z(C)_m$ is 1 and m is an integer of 2 to 64 (i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64), z in $(C)_m NR_z$ or $NR_z(C)_m$ is 2 and m is an integer of 2 to 64 (i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64), or z in $(C)_m NR_z$ or $NR_z(C)_m$ is 3 and m is an integer of 2 to 64 (i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64), (ii) z in $(AQ)_n NR_z$ or $NR_z(AQ)_n$ is 1 and n is an integer of 6 to 24 (i.e. 6, 7, 8, 9, 10, 11, 12, 13, 14, 15, 16, 17, 18, 19, 20, 21, 22, 23, or 24), z in $(AQ)_n NR_z$ or $NR_z(AQ)_n$ is 2 and n is an integer of 6 to 24 (i.e. 6, 7, 8, 9, 10, 11, 12, 13, 14, 15, 16, 17, 18, 19, 20, 21, 22, 23, or 24), or z in $(AQ)_n NR_z$ or $NR_z(AQ)_n$ is 3 and n is an integer of 6 to 24 (i.e. 6, 7, 8, 9, 10, 11, 12, 13, 14, 15, 16, 17, 18, 19, 20, 21, 22, 23, or 24), (iii) z in $NR_z(QAQ)_o$ or $(QAQ)_o NR_z$ is 1 and o is an integer of 8 to 16 (i.e. 8, 9, 10, 11, 12, 13, 14, 15, or 16), z in $NR_z(QAQ)_o$ or $(QAQ)_o NR_z$ is 2 and o is an integer of 8 to 16 (i.e. 8, 9, 10, 11, 12, 13, 14, 15, or 16), or z in $NR_z(QAQ)_o$ or $(QAQ)_o NR_z$ is 3 and o is an integer of 8 to 16 (i.e. 8, 9, 10, 11, 12, 13, 14, 15, or 16), (iv) z in $NR_z(C)_m NR_z$ is 1 and m is an integer of 2 to 64 (i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64), z in $NR_z(C)_m NR_z$ is 2 and m is an integer of 2 to 64 (i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64), or z in $NR_z(C)_m NR_z$ is 3 and m is an integer of 2 to 64 (i.e. 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64), or (v) z in $NR_z(AQ)_n NR_z$ is 1 and n is an integer of 6 to 24 (i.e. 6, 7, 8, 9, 10, 11, 12, 13, 14, 15, 16, 17, 18, 19, 20, 21, 22, 23, or 24), z in $NR_z(AQ)_n NR_z$ is 2 and n is an integer of 6 to 24 (i.e. 6, 7, 8, 9, 10, 11, 12, 13, 14, 15, 16, 17, 18, 19, 20, 21, 22, 23, or 24), or z in $NR_z(AQ)_n NR_z$ is 3 and n is an integer of 6 to 24 (i.e. 6, 7, 8, 9, 10, 11, 12, 13, 14, 15, 16, 17, 18, 19, 20, 21, 22, 23, or 24), wherein NR stands for a non-repetitive unit, preferably NR3 or NR4.

Most preferably, the silk protein isolated with the method of the present invention is $C_{16}NR4$, $C_{32}NR4$, $(AQ)_{12}NR3$, $(AQ)_{24}NR3$, $(AQ)_{12}$, $(AQ)_{24}$, $C_{16}$, $C_{32}$, $NR4C_{16}NR4$, $NR4C_{32}NR4$, $NR3C_{16}NR3$, $NR3C_{32}NR3$, $NR4(AQ)_{12}NR4$, $NR4(AQ)_{24}NR4$, $NR3(AQ)_{12}NR3$, $NR3(AQ)_{24}NR3$, $(QAQ)_8$ or $(QAQ)_{16}$.

An ADF-3, ADF-4, MaSp I or MaSp II variant differs from the reference (wild-type) ADF-3 (SEQ ID NO: 1), ADF-4 (SEQ ID NO: 2), MaSp I (SEQ ID NO: 43) or MaSp II (SEQ ID NO: 44) polypeptide from which it is derived by up to 150 (up to 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, or 150) amino acid changes in the amino acid sequence (i.e. substitutions, insertions, deletions, N-terminal truncations and/or C-terminal truncations). Such a variant can alternatively or additionally be characterised by a certain degree of sequence identity to the reference (wild-type) polypeptide from which it is derived. Thus, an ADF-3, ADF-4, MaSp I or MaSp II variant has a sequence identity of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 99.9% to the respective reference (wild-type) ADF-3, ADF-4, MaSp I or MaSp II polypeptide. Preferably, the sequence identity is over a continuous stretch of at least 20, 25, 30, 35, 40, 50, 60, 70, 80, 90, 100, 120, 150, 180, 200, 250, 300, 350, 400, or more amino acids, preferably over the whole length of the respective reference (wild-type) ADF-3, ADF-4, MaSp I or MaSp II polypeptide.

It is particularly preferred that the sequence identity is at least 80% over the whole length, is at least 85% over the whole length, is at least 90% over the whole length, is at least 95% over the whole length, is at least 98% over the whole length, or is at least 99% over the whole length of the respective reference (wild-type) ADF-3, ADF-4, MaSp I or MaSp II polypeptide. It is further particularly preferred that the sequence identity is at least 80% over a continuous stretch of at least 20, 30, 50, 100, 150, 200, 250, or 300 amino acids, is at least 85% over a continuous stretch of at least 20, 30, 50, 100, 150, 200, 250, or 300 amino acids, is at least 90% over a continuous stretch of at least 20, 30, 50, 100, 150, 200, 250, or 300 amino acids, is at least 95% over a continuous stretch of at least 20, 30, 50, 100, 150, 200, 250, or 300 amino acids, is at least 98% over a continuous stretch of at least 20, 30, 50, 100, 150, 200, 250, or 300 amino acids, or is at least 99% over a continuous stretch of at least 20, 30, 50, 100, 150, 200, 250, or 300 amino acids of the respective reference (wild-type) ADF-3, ADF-4, MaSp I or MaSp II polypeptide.

A fragment (or deletion variant) of the ADF-3 (SEQ ID NO: 1) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 120, 150, 170, 200, 220, 250, 270, 300, 320, 350, 370, 400, 420, 450, 470, 500, 520, 550, 570, 600, or 610 amino acids at its N-terminus and/or at its C-terminus. The deletion can also be internally.

A fragment (or deletion variant) of the ADF-4 (SEQ ID NO: 2) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 120, 150, 170, 200, 220, 250, 270, 300, 320, 330, 340, 350, 360, 370, 380, or 390 amino acids at its N-terminus and/or at its C-terminus. The deletion can also be internally.

A fragment (or deletion variant) of the MaSp I (SEQ ID NO: 43) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 620, 640, 660, 670, 680, or 690 amino acids at its N-terminus and/or at its C-terminus. The deletion can also be internally.

A fragment (or deletion variant) of the MaSp II (SEQ ID NO: 44) polypeptide has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 520, 540, 560, or 570 amino acids at its N-terminus and/or at its C-terminus. The deletion can also be internally.

Additionally, the ADF-3, ADF-4, MaSp I or MaSp II variant or fragment is only regarded as an ADF-3, ADF-4, MaSp I or MaSp II variant or fragment within the context of the present invention, if the modifications with respect to the amino acid sequence on which the variant or fragment is based do not change the property of the silk protein to be insoluble and to retain its insolubility, so that said silk protein can still be separated from the solubilized insoluble host cell parts in step c) of the method of the present invention. Preferably, the ADF-3, ADF-4, MaSp I or MaSp II variant or fragment is still insoluble in an aqueous solution, e.g. buffered aqueous solution, in a culture medium, in a fermentation medium, in technical water or in deionized water and stays insoluble to more than 80, 85, 90, 91, 92, 93, 94, 95, 96, 97, 98, 99, 99.9% or even to 100% in an aqueous solution, e.g. buffered aqueous solution, in a culture medium, in a fermentation medium, in technical water or deionized water comprising a base (e.g. NaOH, 0.005 to 1M) over a period of 10 to 90 minutes, e.g. over 10, 15, 20, 25, 30, 35, 40, 45, 50, 55, 60, 65, 70, 75, 80, 85, or 90 minutes and/or at a temperature between 4 and 60° C., e.g. at 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, or 60° C. In preferred embodiments of the present invention, the ADF-3, ADF-4, MaSp I or MaSp II variant or fragment, which remains/stays insoluble, is separated/isolated from the solubilized insoluble host cell parts by filtration, preferably using a filter membrane having a pore size of 10 nm to 200 nm, and/or by centrifugation, preferably at 3000 to 12000×g and more preferably at 4000 to 8000×g, for 10 to 40 min, preferably 20 to 40 min.

In another embodiment the silk protein further comprises an amino terminal and/or a carboxy terminal TAG selected from the group consisting of
(i) $TAG^{CYS1}$ consisting of the amino acid sequence GCGGGGGGSGGGG (SEQ ID NO: 35),
(ii) $TAG^{CYS2}$ consisting of the amino acid sequence GCGGGGGG (SEQ ID NO: 36),
(iii) $TAG^{CYS3}$ consisting of the amino acid sequence GCGGSGGGGSGGGG (SEQ ID NO: 37),
(iv) $TAG^{LYS1}$ consisting of the amino acid sequence GKGGGGGGSGGGG (SEQ ID NO: 38), and
(v) $TAG^{LYS2}$ consisting of the amino acid sequence GKGGGGGG (SEQ ID NO: 39).

These TAGs contain cysteine and/or lysine and can be used to covalently link substances to said silk protein after its isolation. Preferably, the covalently linked/coupled substance is selected from the group consisting of a polypeptide, a lipid, a dye, a conjugated metal, activated carbon, and an agent.

Most preferably, the silk polypeptide isolated with the method of the present invention comprises or consists of $TAG^{CYS1}C_{16}$, $C_{16}TAG^{CYS1}$, $TAG^{CYS1}C_{16}$, $C_{16}TAG^{CYS1}C_{16}TAG^{CYS2}$, $TAG^{CYS2}C_{16}TAG^{CYS2}C_{16}TAG^{CYS2}$, $TAG^{CYS3}C_{16}$, $C_{16}TAG^{CYS3}$, $TAG^{CYS3}C_{16}TAG^{CYS3}$, $TAG^{LYS1}C_{16}$, $C_{16}TAG^{LYS1}$, $TAG^{LYS1}C_{16}TAG^{LYS1}$, $TAG^{LYS2}C_{16}$, $C_{16}TAG^{LYS2}$, or $TAG^{LYS2}C_{16}TAG^{LYS2}$.

In a second aspect, the invention relates to an insoluble target protein obtainable by the method of the first aspect.

In a further aspect, the invention provides a method of isolating an insoluble target protein from a protein solution comprising the steps of:
a) providing a protein solution comprising the insoluble target protein,
b) adding an aqueous solution of at least one base to said solution in an amount which is sufficient to disrupt said host cells and/or to solubilize said insoluble host cell parts, and
c) separating the insoluble target protein from the solubilized insoluble host cell parts, wherein in step b) the target protein remains insoluble and at least 80% of the insoluble host cell parts are solubilized.

Preferably the protein solution is milk from a transgenic animal, e.g. goat, sheep or cattle, which expresses the insoluble target protein. As to the definitions, the selection of the base added in step b), the reagents used, the process conditions and parameters, and the target protein isolable, it is referred to the explanations made above regarding the first aspect of the invention.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be encompassed by the present invention.

The following figures and examples are merely illustrative of the present invention and should not be construed to limit the scope of the invention as indicated by the appended claims in any way.

BRIEF DESCRIPTION OF THE TABLES AND FIGURES

FIG. 1: Visualization of phase separation. The cell remnants are completely dissolved, whereas the $C_{16}$ target protein remains insoluble in pellet fraction. The addition of different agents affects the result of the phase separation of the $C_{16}$ target protein pellet. FIG. 1 shows the one-step-purification as described in example 2. Cell debris was incubated for 45 min with A: 0.05 M NaOH; B: 0.05 M NaOH and 4.8 M Urea, C, 0.05 M NaOH and 0.1% Tween 20, D: 4.8 M Urea, E: 2 M guanidine hydrochloride, F: 0.1% Tween 20. After incubation and a following centrifugation step, the sediments of A, B and C show a white pellet which almost entirely consists of $C_{16}$ target protein in high purity. In samples D, E, and F, no sharp phase separation was observed.

Figure 2:
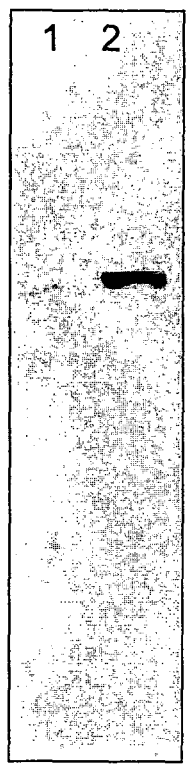

FIG. 2: Immunoblot analysis (Western Blot) of the recombinant spider silk protein $C_{16}$ purified according to example 2. Lane 2, loaded with $C_{16}$, shows a single protein signal ($C_{16}$ positive control in Lane 1). No protein degradations could be observed. Specific detection of the target protein is mediated via conjugated T7-tag peptide according to the enclosed protocol of SERVAGel™ TG10 (43210). In detail: Lane 1: 0.5 µg of positive control $C_{16}$ (purification according to Huemmerich et. al., *Biochemistry* 2004, 43, 13604-13612); Lane 2: 5 µg of $C_{16}$ (purification according to example 2). Antibody: T7-Tag® Antibody HRP Conjugate, Cat. Nr: 69048-3, Novagen; PVDF-membrane: Roti® Fluoro-PVDF, PVM020C-099, Roth; Immunoblot (Western blot) was performed according to enclosed protocol of SERVAGel™ TG10 (43210). Blocking solution: 5% milk powder in 1×PBS-Buffer, incubation 30 min; detection was realized with Lumi-light$^{Plus}$-Solution, 12015196001, Roche, according to enclosed protocol.

Figure 3:
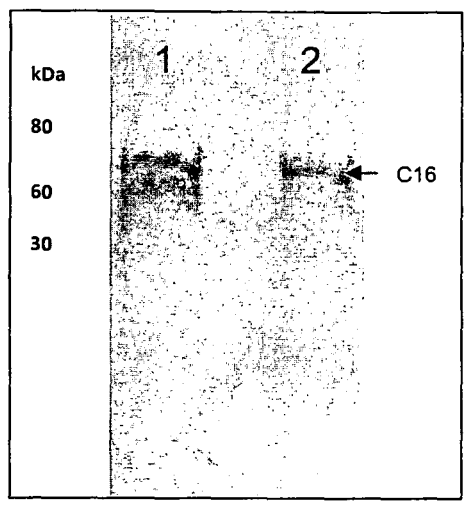
Figure 4:
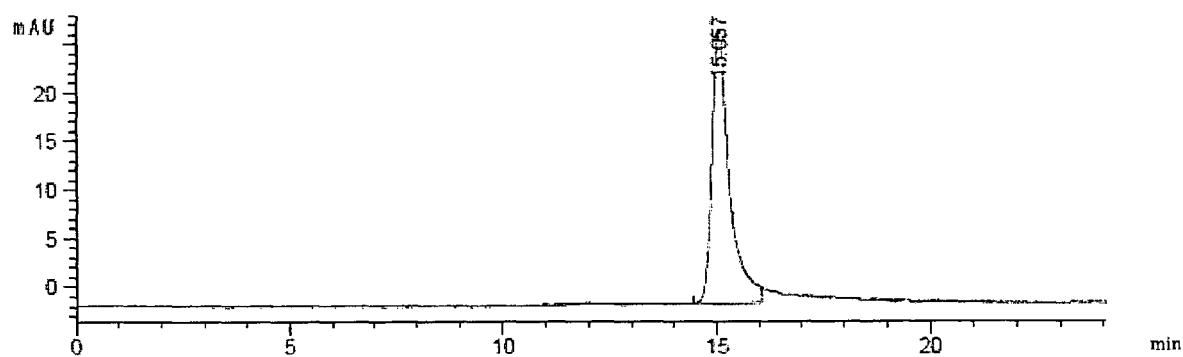

FIG. 3: SDS-Page analysis (silver stained) of a recombinant spider silk protein $C_{16}$ purified according to process described in example 2 (lane 2), loaded with 10 µg of $C_{16}$ protein, shows a single protein signal ($C_{16}$ protein positive control in lane 1). According to FIG. 1 no contaminations could be observed. Lane 1: positive control 10 µg of $C_{16}$ (purification according to Huemmerich et. al., Biochemistry 2004, 43, 13604-13612); Lane 2: 10 µg of $C_{16}$ (purification as described in example 2. SDS-Page was performed with SERVAGel™ TG10 (43210) according to enclosed protocol. The staining was realized with SERVA Silverstain Kit (35076) according to enclosed protocol FIG. 4: HPLC analysis of a recombinant spider silk protein $C_{16}$ purified according to example 2. The Chromatogram shows a single sharp peak at 15.057 min (identified as target protein $C_{16}$, detected at a wavelength of 280 nm). No contaminations could be observed. Column parameters: TSK-Gel® HPLC Column G3000 SWXL, Tosoh Bioscience, Nr. 08541, bore diameter: 7.8 mm, length: 30.0 cm. The flow rate was constant at 0.5 ml/min.

Figure 5:
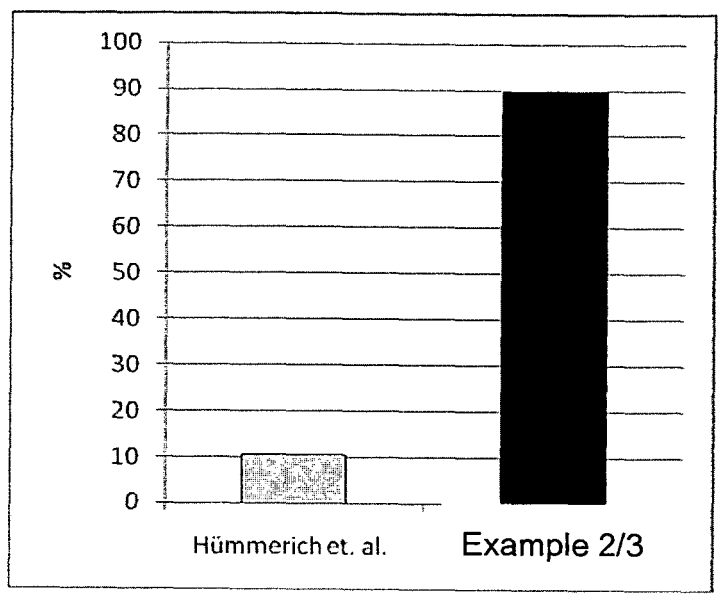

FIG. 5: The purification method by Huemmerich et al., Biochemistry 2004, 43, 13604-13612 and purification method according to example 2 were compared regarding the amount of purified $C_{16}$ protein (target protein). It could be shown that the yield of target protein $C_{16}$ is significant higher (approx. nine times) when purified according to the inventive method, see example 2 (89%), compared to the method by Huemmerich et al., Biochemistry 2004, 43, 13604-13612 (10.4%). FIG. 5 shows the yield of target $C_{16}$ protein purified according to example 2. Both purification methods (Huemmerich et. al., Biochemistry 2004, 43, 13604-13612) and the purification method as described in example 2 were compared regarding the amount of purified $C_{16}$ protein.

Figure 6:
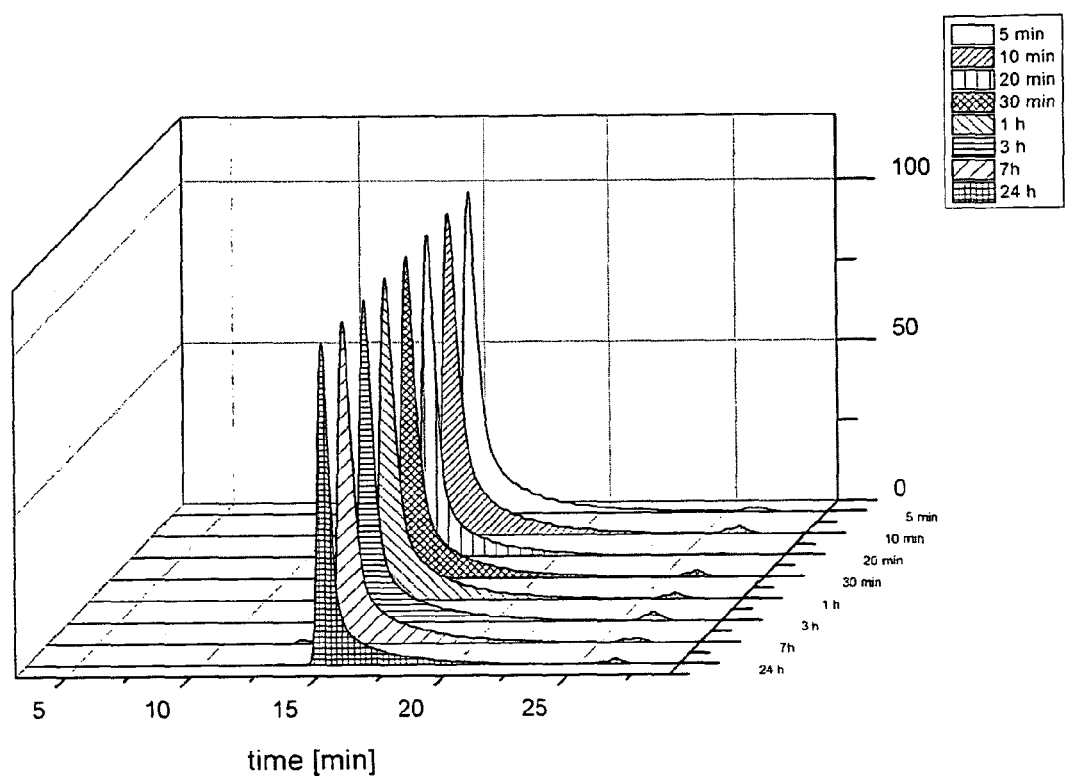

FIG. 6: Stability assay of purified recombinant spider silk protein $C_{16}$ treated with 0.05 M sodium hydroxide as described in example 2. No significant protein degradation could be observed after incubation with 0.05 M for a time period of between 5 min to 24 hours. Identification of target protein is mediated via fluorescence detector in HPLC runs (Excitation wavelength: 275 nm—Emission wavelength: 305 nm; Gradient: isocratic, Eluent: 100 mM Tris/HCl pH 7.5). Samples were taken at different time points of incubation at 5 min, 10 min, 20 min, 30 min, 1 h, 3 h, 7 h and 24 h. The data of each chromatogram were standardized to 100% for a better detection of minor differences.

EXAMPLES

In order to separate target proteins, the inventors exemplarily designed the synthetic silk polypeptide $C_{16}$ which is derived from the dragline silk protein ADF-4 from the European garden cross spider *Araneus diadematus*. The protein was chosen based on previous observations that ADF-3 and/or ADF-4 as well as their variants display efficient assembly behavior.

Example I

Preparation of a Suspension of Microbial Cells

The microbial cells were lysed/disrupted two times using a homogenizer [APV Gaulin GmbH, LAB60-15 REFI] at a pressure of 900 bar at room temperature. The resulting cell debris solution was centrifuged at 9000×g for 30 min, 20° C. The supernatant was discarded and the cell debris sediment was used for the one-step-purification.

Example II

Isolation of $C_{16}$

The wet weight of the cell debris sediment from the preparation of microbial cell solution (example 1) was determined to adjust the required dilution volume. The ratio of cell debris sediment (wet weight) and 0.05 M NaOH was 1:3 (w/w). In this example the cell debris sediment was measured to be 5 gram. The weight of sample additives was therefore calculated to be 15 gram. The additives in this experiment were A: 0.05 M NaOH; B: 0.05 M NaOH and 4.8 M Urea, C, 0.05 M NaOH and 0.1% Tween 20, D: 4.8 M Urea, E: 2 M guanidine hydrochloride or F: 0.1% Tween 20. All samples were incubated for 45 min at 20° C. under well mixing. After incubation the samples were centrifuged at 8000×g for 30 min, 20° C. (see FIG. 1). The sediments of A, B and C showed a white pellet which almost entirely consists of $C_{16}$ target protein in high purity. In samples D, E, and F, no sharp phase separation was observed.

Following this step the aggregated $C_{16}$ protein (target protein) was present in the pellet fraction, whereas the supernatant has been discarded. Two additional washing steps with $H_2O$ (centrifugation at 8000×g, 30 min, 20° C.) were performed to increase the purity of the $C_{16}$ target protein. The $C_{16}$ target protein thus obtained was analyzed in SDS-Page analysis (silver stain) [The staining was carried out with SERVA Silverstain Kit (35076) according to the enclosed protocol.] (see FIG. 3), Immunoblot analysis (Western Blot) [The Immunoblot analysis (Western Blot) was performed according to the enclosed protocol of SERVAGel™ TG10 (43210). Blocking solution: 5% milk powder in 1×PBS-Buffer, incubation 30 min; detection was realized with Lumi-light$^{Plus}$-Solution, 12015196001, Roche, according to enclosed protocol.] (see FIG. 2) and HPLC analysis [Column parameters: TSK-Gel® HPLC Column G3000 SWXL, Tosoh Bioscience, Nr. 08541, bore diameter: 7.8 mm, length: 30.0 cm. The flow rate was constant at 0.5 ml/min.] (see FIG. 4).

Example III

Isolation of $C_{16}$ Compared to Standard Process

The wet weight of the cell debris sediment from the preparation of microbial cells was determined to adjust the required dilution volume. The ratio of cell debris sediment (wet weight) and 0.05 M NaOH was one to three (w/w). In this experiment the cell debris sediment was measured to be one kilogram. The weight of 0.05M NaOH was therefore calculated to 3 kg (total weight: 4 kg). The sample was incubated for 45 min at 20° C. under mixing. After incubation the sample were centrifuged at 8000×g for 30 min, 20° C. Following this step the $C_{16}$ target protein was present in the pellet fraction, whereas the supernatant has been discarded. Two additional washing steps with $H_2O$ (centrifugation at 8000×g, 30 min, 20° C.) increased the purity of $C_{16}$ target protein. In this example the amount of purified C16 target protein was compared to the purification method as described by Huemmerich et al., Biochemistry 2004, 43, 13604-13612. In contrast to the inventive method, the purification according to Huemmerich et al., was carried out with the supernatant after cell disruption out from the preparation of microbial cells.

TABLE 1

| Purification method | Yield [g C16/kg microbial cell solution] |
|---|---|
| Huemmerich et al., Biochemistry 2004, 43, 13604-13612 | 0.20 |
| Experiment [-Ib-] | 1.72 |

Regarding the amount of purified C16 target protein, it could be shown that the yield of target protein C16 was significant higher (approx. nine times) when purified as described in example 2 (see Table 1, FIG. 5).

Example IV

Protein Stability of C16

A microbial cell solution containing the target protein $C_{16}$ was treated with 0.05 M NaOH. As described in example 1 and 2 the microbial cells were lysed two times using a homogenizer [APV Gaulin GmbH, LAB60-15 RBFI] at a pressure of 900 bar at room temperature. The resulting cell debris solution was centrifuged at 9000×g for 30 min, 20° C. The supernatant was discarded and the cell debris sediment was used for the one-step-purification. The wet weight of the cell debris sediment from the preparation of microbial cell solution (example 1) was determined to adjust the required dilution volume. The ratio of cell debris sediment (wet weight) and 0.05 M NaOH was 1:3 (w/w).

Samples were taken at different time points of incubation at 5 min, 10 min, 20 min, 30 min, 1 h, 3 h, 7 h and 24 h. The data of each chromatogram were standardized to 100% for a better detection of minor differences. As shown in FIG. 6 no significant protein degradation takes place after incubation with 0.05 M NaOH for a time period between 5 min to 24 hours. Instrument parameters: TSK-Gel® HPLC Column G3000 SWXL, bore diameter: 7.8 mm, length: 30.0 cm. Flow rate: 0.5 ml/min, Fluorescence detection: Excitation wavelength: 275 nm—Emission wavelength: 305 nm; Gradient: isocratic, Eluent: 100 mM Tris/HCl pH 7.5.

The invention claimed is:

1. A method of purifying an insoluble target protein from a suspension of intact or disrupted host cells comprising the steps of:
    a) providing a suspension of intact or disrupted host cells comprising an insoluble target protein and insoluble host cell parts,
    b) adding an aqueous solution of at least one base to said suspension in an amount which is sufficient to disrupt said host cells and/or to solubilize said insoluble host cell parts, and
    c) purifying the insoluble target protein from the solubilized insoluble host cell parts,
    wherein the purified insoluble target protein remains insoluble throughout the entire purification process, and wherein the purified insoluble target protein has a purity of at least 80%.

2. The method of claim 1, wherein the host cells are bacterial, yeast, plant or insect host cells.

3. The method of claim 1, wherein the purified insoluble target protein has a purity of at least 90%.

4. The method of claim 1, wherein the base is a metal hydroxide and/or ammonia.

5. The method of claim 4, wherein the metal hydroxide is selected from the group consisting of sodium hydroxide (NaOH), potassium hydroxide (KOH), and calcium hydroxide (Ca(OH)$_2$), or is a combination thereof.

6. The method of claim 1, wherein the final concentration of the base in step (b) ranges from 0.005 M to 1 M.

7. The method of claim 1, wherein the method further comprises the addition of at least one reagent (i) prior to step b), (ii) in step b) and/or (iii) subsequent to step b).

8. The method of claim 7, wherein the reagent is selected from the group consisting of a denaturing agent, a kosmotropic agent, and a detergent, or is a combination thereof.

9. The method of claim 1, wherein step c) is achieved by centrifugation, sedimentation and/or filtration.

10. The method of claim 1, wherein the method further comprises subsequent to step b) and prior to step c) a step b') of homogenization of said suspension.

11. The method of claim 1, wherein the method further comprises subsequent to step c) a step d) of washing the purified insoluble target protein with an aqueous solution, an organic solution and/or urea.

12. The method of claim 1, wherein at least 90% of the target protein remains insoluble after the addition of an aqueous solution comprising at least one base in step b) over a time period of between 10 and 40 min and at a temperature of between 15° C. and 25° C.

13. The method of claim 1, wherein the insoluble target protein forms a protein aggregate which comprises at least 85% of said target protein.

14. The method of claim 1, wherein the insoluble target protein is a silk protein comprising at least two identical repetitive units.

15. The method of claim 14, wherein the silk protein comprises at least two identical repetitive units each comprising at least one consensus sequence selected from the group consisting of:
   i) GPGXX (SEQ ID NO: 3), wherein X is in each case independently selected from the A, S, G, Y, P, and Q;
   ii) GGX, wherein X is in each case independently selected from Y, P, R, S, A, T, N and Q; and
   iii) Ax, wherein x is an integer from 5 to 10.

16. The method of claim 15, wherein the repetitive units are independently selected from module A (SEQ ID NO: 20), module C (SEQ ID NO: 21), module Q (SEQ ID NO: 22), module K (SEQ ID NO: 23), module sp (SEQ ID NO: 24), module S (SEQ ID NO: 25), module R (SEQ ID NO: 26), module X (SEQ ID NO: 27) or module Y (SEQ ID NO: 28), or variants thereof.

17. The method of claim 14, wherein the silk protein further comprises at least one non-repetitive (NR) unit.

18. The method of claim 1, wherein steps a) to c) are carried out at a temperature of between 4° C. and 60° C.

19. The method of claims 1, wherein steps a) to c) are carried out at a pressure of between 10 kPa and 1000 kPa.

* * * * *